(12) United States Patent
Kalle et al.

(10) Patent No.: US 8,735,353 B2
(45) Date of Patent: May 27, 2014

(54) POLYPEPTIDES AND USES THEREOF

(75) Inventors: Martina Kalle, Lund (SE); Gopinath Kasetty, Lund (SE); Nils Martin Malmsten, Taby (SE); Praveen Papareddy, Lund (SE); Artur Schmidtchen, Lund (SE); Bjorn Ulrik Walse, Lund (SE)

(73) Assignee: XMedic AB, Lund (SE)

( * ) Notice: Subject to any disclaimer, the term of this patent is extended or adjusted under 35 U.S.C. 154(b) by 0 days.

(21) Appl. No.: 13/497,622

(22) PCT Filed: Sep. 22, 2010

(86) PCT No.: PCT/GB2010/001778
§ 371 (c)(1),
(2), (4) Date: Aug. 21, 2012

(87) PCT Pub. No.: WO2011/036442
PCT Pub. Date: Mar. 31, 2011

(65) Prior Publication Data
US 2013/0052258 A1    Feb. 28, 2013

(30) Foreign Application Priority Data

Sep. 22, 2009   (GB) .................................. 0916576.2

(51) Int. Cl.
| *A61K 38/16* | (2006.01) |
| *A61K 38/36* | (2006.01) |
| *C07K 14/00* | (2006.01) |
| *A61P 7/02* | (2006.01) |
| *A61P 29/00* | (2006.01) |

(52) U.S. Cl.
CPC ................. *A61K 38/16* (2013.01); *A61K 38/36* (2013.01); *C07K 14/00* (2013.01)
USPC ....... 514/13.7; 514/12.2; 514/21.3; 514/21.4; 530/324; 530/325; 530/326

(58) Field of Classification Search
CPC ... A61K 38/16; A61K 38/36; A61K 38/4833; C12N 9/6429; C12Y 304/21005; C07K 14/00
See application file for complete search history.

(56) References Cited

U.S. PATENT DOCUMENTS

| 4,235,871 | A | 11/1980 | Papahadjopoulos et al. |
| 5,643,872 | A | 7/1997 | Ali et al. |
| 5,851,451 | A | 12/1998 | Takechi et al. |
| 6,008,058 | A | 12/1999 | Spatola et al. |
| 8,076,286 | B2 | 12/2011 | Schmidtchen et al. |
| 2004/0209819 | A1 | 10/2004 | Carney |
| 2007/0282095 | A1* | 12/2007 | Hosokawa et al. ........... 530/381 |

FOREIGN PATENT DOCUMENTS

| EP | 0 213 303 A2 | 3/1987 |
| WO | WO-03/059973 A2 | 7/2003 |
| WO | WO-2005/007197 A2 | 1/2005 |
| WO | WO-2005/007197 A3 | 1/2005 |
| WO | WO-2007/091959 A1 | 8/2007 |
| WO | WO 2007091959 A1 * | 8/2007 | ............... C07K 7/06 |
| WO | WO-2008/036387 A2 | 3/2008 |

OTHER PUBLICATIONS

Rudinger, Peptide Hormones, Ja Parsons, Ed., 1976, pp. 1-7.*
Sigma, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Definition of derivative, from http://cancerweb.ncl.ac.uk/cgi-bin/omd?query=derivative, pp. 1-5, accessed Jul. 7, 2005.*
Definition of fragment, from http://www.merriam-webster.com/dictionary/fragment, pp. 1-3, accessed May 1, 2013.*
Sriskandan et al, The immunology of sepsis, J Pathol, 2008, 214, pp. 211-223.*
Aortic Aneurysms-Merck Manual, pp. 1-7, accessed May 1, 2013.*
Acute Abdominal Pain-Merck Manual, pp. 1-7, accessed May 1, 2013.*
Acute Renal Failure-Merck Manual, pp. 1-9, accessed May 1, 2013.*
Peripheral Neuropathy-Merck Manual, pp. 1-7, accessed May 1, 2013.*
Sepsis and Septic Shock-Merck Manual, pp. 1-5, accessed May 1, 2013.*
Agadir. "An Algorithm to Predict the Helical Content of Peptides," located at <http://agadir.crg.es/>, last visited on Jan. 24, 2013.
Amara, U. et al. (2008, e-pub. Jul. 22, 2009). "Interaction Between the Coagulation and Complement System," *Adv. Exp. Med. Biol.* 632:71-79.
Andersson, E. et al. (2004). "Antimicrobial Activities of Heparin-Binding Peptides," *Eur. J. Biochem.* 271:1219-1226.
Blondelle, S.E. et al. (2000). "Combinatorial Libraries: A Tool to Design Antimicrobial and Antifungal Peptide Analogues Having Lytic Specificities for Structure-Activity Relationship Studies," *Biopolymers* 55:74-87.

(Continued)

*Primary Examiner* — Julie Ha
*Assistant Examiner* — Li Ni Komatsu
(74) *Attorney, Agent, or Firm* — Morrison & Foerster LLP

(57) ABSTRACT

The present invention provides polypeptides comprising or consisting of an amino acid sequence from thrombin, or a fragment, variant, fusion or derivative thereof, or a fusion of said fragment, variant or derivative thereof, for use in the treatment or prevention of inflammation and/or excessive coagulation of the blood. Related aspects of the invention provide isolated polypeptides comprising or consisting of an amino acid sequence of any one of SEQ ID NOs: 1 to 7, or a fragment, variant, fusion or derivative thereof, or a fusion of said fragment, variant or derivative thereof, which exhibit an anti-inflammatory activity, together with isolated nucleic acid molecules, vectors and host cells for making the same. Additionally provided are pharmaceutical compositions comprising a polypeptide of the invention, as well as methods of use of the same in the treatment and/or prevention of inflammation and/or excessive coagulation.

7 Claims, 33 Drawing Sheets

(56) References Cited

OTHER PUBLICATIONS

Bode, W. (2006). "The Structure of Thrombin: A Janus-Headed Proteinase," *Seminars in Thrombosis Hemostasis*, vol. 32 Supp 1:16-31.

Bowen, S. et al. (1999). "Relationship Between Molecular Mass and Duration of Activity of Polyethylene Glycol Conjugated Granulocyte Colony-Stimulating Factor Mutein," *Exp Hematol*. 27(3):425-432.

Brogden, K.A. (Mar. 2005, e-pub. Feb. 10, 2005). "Antimicrobial Peptides: Pore Formers or Metabolic Inhibitors in Bacteria?" *Nat Rev Microbiol* 3:238-250.

Brower, M.S. et al. (Mar. 1987). "Human Neutrophil Elastase Alters Human α- Thrombin Function: Limited Proteolysis Near the γ-Cleavage Site Results in Decreased Fibrinogen Clotting and Platelet-Stimulatory Activity," *Blood* 69(3):813-819.

Carlemalm, E. et al. (Oct. 1985). "Low Temperature Embedding With Lowicryl Resins: Two New Formulations and Some Applications," *J Microsc* 140(Part 1):55-63.

Chapman, A.P. (2002). "PEGylated Antibodies and Antibody Fragments for Improved Therapy: A Review," *Advanced Drug Delivery Reviews* 54(4):531-545.

Chapman, A.P. et al. (Aug. 1999). "Therapeutic Antibody Fragments With Prolonged In Vivo Half-Lives," *Nature Biotechnology* 17(8):780-783.

Cole, A.M. et al. (2001). "Cutting Edge: IFN-Inducible ELR- CXC Chemokines Display Defensin-Like Antimicrobial Activity," *J Immunol* 167:623-627.

Davie, E.W. et al. (2006). "An Overview of the Structure and Function of Thrombin," *Seminars in Thrombosis Hemostasis*, vol. 32 (Supp 1):3-15.

EBI Accession No. UNIPROT: Q86WA1, last updated Oct. 31, 2006, located at <http://www.ncbi.nlm.nih.gov/protein/Q86WA1>, last visited on Jan. 23, 2013, one page.

EBI Accession No. UNIPROT: Q8TD58, last updated Oct. 31, 2006, located at <http://www.ncbi.nlm.nih.gov/protein/Q8TD58>, last visited on Jan. 23, 2013, one page.

Elsbach, P. (Jun. 2003). "What Is the Real Role of Antimicrobial Polypeptides That Can Mediate Several Other Inflammatory Responses?" *J. Clin. Invest*. 111(11):1643-1645.

Expasy. "FindPept Tool," located at <www.expasy.org/tools/findpept.html>, last visited on Jan. 24, 2013.

Fernandez-Lopez, S. et al. (Jul. 26, 2001). "Antibacterial Agents Based on the Cyclic D,L-α-Peptide Architecture," *Nature* 412:452-455.

French, G.L. (2005). "Clinical Impact and Relevance of Antibiotic Resistance," *Advanced Drug Delivery Reviews* 57:1514-1527.

Frick, I.M. et al. (2006, e-pub. Nov. 9, 2006). "The Contact System—A Novel Branch of Innate Immunity Generating Antibacterial Peptides," *The Embo Journal* 25(23):5569-5578.

Ganz, T. (Sep. 2003). "Defensins: Antimicrobial Peptides of Innate Immunity," *Nat Rev Immunol* 3:710-720.

Glenn, K.C. et al. (1988). "Synthetic Peptides Bind to High-Affinity Thrombin Receptors and Modulate Thrombin Mitogenesis," *Peptide Research* 1(2):65-73.

Greenfield, N. et al. (Oct. 1969). "Computed Circular Dichroism Spectra for the Evaluation of Protein Conformation," *Biochemistry* 8(10):4108-4116.

Griffen, M. et al. (1993). "Enzyme Immobilisation," Chapter 4 in *Technological Application of Biocatalysts* (BIOTOL SERIES), Butterworth-Heinemann: Linacre House, Jordan Hill, Oxford, pp. 75-118.

Hancock, R.E.W. et al. (Dec. 2006, e-pub. Dec. 11, 2006). "Antimicrobial and Host-Defense Peptides As New Anti-Infective Therapeutic Strategies," *Nature Biotechnology* 24(12):1551-1557.

Harder, J. et al. (2007). "Human Antimicrobial Proteins—Effectors of Innate Immunity," *J. Endotoxin. Res*. 13(6):317-338.

Hilpert, K. et al. (Aug. 2005, e-pub. Jul. 24, 2005). "High-Throughput Generation of Small Antibacterial Peptides With Improved Activity," *Nature Biotechnology* 23(8):1008-1012.

Huang, H.W. (2006, e-pub. Feb. 28, 2006). "Molecular Mechanism of Antimicrobial Peptides: The Origin of Cooperativity," *Biochim Biophys Acta* 1758:1292-1302.

Hubbell, J.A. (Jun. 1995). "Biomaterials in Tissue Engineering," *Biotechnology* 13:565-576.

International Preliminary Report on Patentability mailed on Mar. 27, 2012, for PCT Patent Application No. PCT/GB2010/001778, filed on Sep. 22, 2010, 8 pages.

International Search Report mailed on May 13, 2011, for PCT Patent Application No. PCT/GB2010/001778, filed on Sep. 22, 2010, 5 pages.

Kowalska, K. et al. (2002). "Direct Antimicrobial Properties of Substance P," *Life Sciences* 71:747-750.

Lehrer, R.I. et al. (2002). "Cathelicidins: A family of Endogenous Antimicrobial Peptides," Curr Opin Hematol 9:18-22.

Lehrer, R.I. et al. (1991). "Ultrasensitive Assays for Endogenous Antimicrobial Polypeptides," *J Immunol Methods* 137:167-173.

Liu, C.Y. et al. (Oct. 25, 1979). "The Binding of Thrombin by Fibrin," *J. Biol. Chem*. 254(20):10421-10425.

Lundqvist, K. et al. (2004, e-pub, May 5, 2004). "Heparin Binding Protein is Increased in Chronic Leg Ulcer Fluid and Released From Granulocytes by Secreted Products of *Pseudomonas Aeruginosa*," *Thromb. Haemost*. 92:281-287.

Luo, P. et al. (2002). "Origin of the Different Strengths of the (i,i+4) and (i,i+3) Leucine Pair Interactions in Helices," *Biophys Chem* 96:103-108.

Malmsten, M. et al. (Feb. 2007). "Antimicrobial Peptides Derived From Growth Factors," *Growth Factors* 25(1):60-70.

Marr, A.K. et al. (2006, e-pub. Aug. 4, 2006). "Antibacterial Peptides for Therapeutic Use: Obstacles and Realistic Outlook," *Curr Opin Pharmacol* 6:468-472.

Meziere, C. et al. (1997). "In Vivo T Helper Cell Response to Retro-Inverso Peptidomimetics," *J. Immunol*. 159:3230-3237.

Mor, A. et al. (1994). "Structure, Synthesis, and Activity of Dermaseptin b, A Novel Vertebrate Defensive Peptide From Frog Skin: Relationship With Adenoregulin," *Biochemistry* 33(21):6642-6650.

Mullins, E.S. et al. (Jan. 15, 2009, e-pub. Oct. 16, 2008). "Genetic Elimination of Prothrombin in Adult Mice Is Not Compatible With Survival and Results in Spontaneous Hemorrhagic Events in Both Heart and Brain," *Blood* 113(3):696-704.

Murakami, M. et al. (2004). "Postsecretory Processing Generates Multiple Cathelicidins for Enhanced Topical Antimicrobial Defense," *J. Immunol*. 172:3070-3077.

Nizet, V. (2006). "Antimicrobial Peptide Resistance Mechanisms of Human Bacterial Pathogens," *Curr. Issues Mol. Biol*. 8:11-26.

Nordahl, E.A. et al. (Oct. 14, 2005). "Domain 5 of High Molecular Weight Kininogen is Antibacterial," *J. Biol. Chem*. 280(41):34832-34839.

Nordahl, E.A. et al. (Nov. 30, 2004). "Activation of the Complement System Generates Antibacterial Peptides," *PNAS* 101(48):16879-16884.

Oppenheim, J.J. et al. (2005, e-pub. Jun. 13, 2005). "Alarmins: Chemotactic Activators of Immune Responses," *Curr. Opin. Immunol*. 17:359-365.

Oren, Z. et al. (1999). "Structure and Organization of the Human Antimicrobial Peptide LL-37 in Phospholipid Membranes: Relevance to the Molecular Basis for Its Non-Cell-Selective Activity," *Biochem. J*. 341:501-513.

Page, M.J. et al. (2008, e-pub. Feb. 9, 2008). "Serine Peptidases: Classification, Structure and Function," *Cell. Mol. Life Sci*. 65 (7-8):1220-36.

Papareddy, P. et al. (Apr. 2010). "Proteolysis of Human Thrombin Generates Novel Host Defense Peptides," *PLoS Pathogens* 6(4):1-15.

Pappareddy, P. et al. (Apr. 2010). "Proteolysis of Human Thrombin Generates Novel Host Defense Peptides," *PLoS Pathogens* 6(4):e1000857, 15 pages.

Pasupuleti, M. et al. (2009, e-pub. Apr. 5, 2009). "Tryptophan End-Tagging of Antimicrobial Peptides for Increased Potency Against *Pseudomonas aeruginosa*," *Biochim Biophys Acta* 1790:800-808.

Pasupuleti, M. et al. (Apr. 17, 2009, e-pub. Apr. 19, 2009). "End-Tagging of Ultra-Short Antimicrobial Peptides by W/F Stretches to Facilitate Bacterial Killing," *PLoS One* 4(4):e5285, nine pages.

(56) References Cited

OTHER PUBLICATIONS

Pasupuleti, M. et al. (Jan. 26, 2007). "Preservation of Antimicrobial Properties of Complement Peptide C3a, From Invertebrates to Humans," *J. Biol. Chem.* 282(4):2520-2528.
Pasupuleti, M. et al. (2008, e-pub. Aug. 9, 2008). "Rational Design of Antimicrobial C3a Analogues With Enhanced Effects Against *Staphylococci* Using an Integrated Structure and Function-Based Approach," *Biochemistry* 47(35):9057-9070.
Pollock, J.S. et al. (Dec. 1991). "Purification and Characterization of Particulate Endothelium-Derived Relaxing Factor Synthase From Cultured and Native Bovine Aortic Endothelial Cells," *PNAS* 88:10480-10484.
Rich, D.H. (Oct. 1986). *Proteinase Inhibitors*, Barrett and Selveson eds., Elsevier, pp. xi-xxii, (Table of Contents Only).
Rydengard, V. et al. (2006). "Zinc Potentiates the Antibacterial Effects of Histidine-Rich Peptides Against *Enterococcus faecalis*," *The Febs Journal* 273:2399-2406.
Rydengard, V. et al. (Aug. 1, 2008). "Histidine-Rich Glycoprotein Protects From Systemic *Candida* Infection," *PLoS Pathogens* 4(8):e1000116, 12 pages.
Sajjan, U.S. et al. (Dec. 2001). "P-113D, An Antimicrobial Peptide Active Against *Pseudomonas aeruginosa*, Retains Activity in the Presence of Sputum From Cystic Fibrosis Patients," *Antimicrob Agents Chemother* 45(12):3437-3444.
Sambrook, J. et al. (2001). *Molecular Cloning, A Laboratory Manual*, 3rd Edition, vol. 1-3, Cold Spring Harbor Laboratory Press: Cold Spring Harbor, New York, 2275 pages.
Sato, H. (2002). "Enzymatic Procedure for Site-Specific Pegylation of Proteins," *Adv Drug Deliv Rev.* 54(4):487-504.
Schmidtchen, A. (2000). "Degradation of Antiproteinases, Complement and Fibronectin in Chronic Leg Ulcers," *Acta Derm Venereol* 80:179-184.
Schmidtchen, A. (2003). "Elastase-Producing *Pseudomonas aeruginosa* Degrade Plasma Proteins and Extracellular Products of Human Skin and Fibroblasts, and Inhibit Fibroblast Growth," *Microbial Pathogenesis* 34:47-55.
Schmidtchen, A. et al. (Jun. 26, 2009). "Boosting Antimicrobial Peptides by Hydrophobic Oligopeptide End Tags," *J. Biol. Chem.* 284(26):17584-17594.
Sjögren, H. (2005, e-pub. Jan. 29, 2005). "Comparison of the Helix-Coil Transition of a Titrating Polypeptide in Aqueous Solutions and at the Air-Water Interface," *Biophys Chem* 116:11-21.
Sower, L.E. et al. (1999). "Thrombin Peptide, TP508, Induces Differential Gene Expression in Fibroblasts Through a Nonproteolytic Activation Pathway," *Experimental Cell Research* 247 (2):422-431.
Strömstedt, A.A. et al. (Feb. 2009). "Evaluation of Strategies for Improvin Proteolytic Resistance of Antimicrobial Peptides by Using Variants of EFK17, an Internal Segment of LL-37," *Antimicrobial Agents Chemother* 53(2):593-602.
Strukova, S.M. (2001). "Thrombin as a Regulator of Inflammation and Reparative Processes in Tissues," *Biochemistry* 66 (1):8-18.
Swiss-Prot Accession No. P00734, last updated Jan. 9, 2013, located at <http://www.ncbi.nlm.nih.gov/protein/P00734>, last visited on Jan. 23, 2013, twenty pages.
Taboureau, O. et al. (2006). "Design of Novispirin Antimicrobial Peptides by Quantitative Structure-Activity Relationship," *Chem. Biol. Drug Des.* 68:48-57.
Thompson, J.D. et al. (1994). "CLUSTAL W: Improving the Sensitivity of Progressive Multiple Sequence Alignment Through Sequence Weighting, Position-Specific Gap Penalties and Weight Matrix Choice," *Nucleic Acid Research* 22(22):4673-4680.
Thorsett, E.D. et al. (Feb. 28, 1983). "Dipeptide Mimics. Conformationally Restricted Inhibitors of Angiotensin-Converting Enzyme," *Biochem. Biophys. Res. Comm.* 111(1):166-171.
Tossi, A. et al. (2000). "Amphipathic, α-Helical Antimicrobial Peptides," *Biopolymers* 55:4-30.
Tossi, A. et al. "Peptide Sequence Analysis Tool," located at <http://www.bbcm.univ.trieste.it/~tossi/HydroCalc/HydroMCalc.html>, last visited on Jan. 24, 2013, three pages.
Veber, D.F. et al. (Jun. 1978). "Conformationally Restricted Bicyclic Analogs of Somatostatin," *PNAS* 75(6):2636-2640.
Veronese, F.M. et al. (2002). "Introduction and Overview of Peptide and Protein Pegylation," *Adv. Drug Deliv.Rev.* 54 (4):453-456.
Veronese, F.M. et al. (Nov. 2005). "PEGylation, Successful Approach to Drug Delivery," *DDT* 10(21):1451-1458.
Wang, Y.S. et al. (2002). "Structural and Biological Characterization of Pegylated Recombinant Interferon Alpha-2b and Its Therapeutic Implications," *Adv. Drug Deliv. Rev.* 54(4):547-570.
Wiegand, I. et al. (2008, e-pub. Jan. 17, 2008). "Agar and Broth Dilution Methods to Determine the Minimal Inhibitory Concentration (MIC) of Antimicrobial Substances," *Nature Protocols* 3(2):163-175.
Written Opinion of the International Searching Authority mailed on May 13, 2011, for PCT Patent Application No. PCT/GB2010/001778, filed on Sep. 22, 2010, 7 pages.
Yount, N.Y. et al. (2006, e-pub. May 30, 2006). "Advances in Antimicrobial Peptide Immunobiology," *Biopolymers* 84:435-458.
Yount, N.Y. et al. (May 11, 2004). "Multidimensional Signatures in Antimicrobial Peptides," *PNAS* 101(19):7363-7368.
Zanetti, M. (Jan. 2004). "Cathelicidins, Multifunctional Peptides of the Innate Immunity," *J. Leukoc. Biol.* 75:39-48.
Zasloff, M. (Jan. 24, 2002). "Antimicrobial Peptides of Multicellular Organisms," *Nature* 415:389-395.
Zelezetsky, I. et al. (2006, e-pub. Apr. 18, 2006). "Alpha-Helical Antimicrobial Peptides-Using a Sequence Template to Guide Structure-Activity Relationship Studies," *Biochim. Biophys. Acta* 1758:1436-1449.
Delvaeye, M. et al. (Sep. 17, 2009, e-pub. Jul. 7, 2009). "Coagulation and Innate Immune Responses: Can We View Them Separately?" *Blood* 114(12):2367-2374.

\* cited by examiner

POLYPEPTIDES AND USES THEREOF

CROSS-REFERENCE TO RELATED APPLICATIONS

This application is a National Phase application under 35 U.S.C. §371 of International Application No. PCT/GB2010/001778 filed Sep. 22, 2010 and claims the benefit of Great Britain Application No. 0916576.2 filed Sep. 22, 2009, the disclosures of which are incorporated herein by reference in their entirety.

FIELD OF THE INVENTION

The present invention relates to novel polypeptides derived from thrombin (i.e. factor II) and their use in the treatment and prevention of inflammation. In particular, the invention provides polypeptides comprising or consisting of an amino acid sequence of SEQ ID NOs: 1 to 7, or a fragment, variant, fusion or derivative thereof, or a fusion of said fragment, variant or derivative thereof, for use medicine, e.g. in the treatment or prevention of inflammation and/or excessive coagulation of the blood.

INTRODUCTION

The innate immune system, largely based on antimicrobial peptides, provides a first line of defence against invading microbes (Lehrer, R. I. & Ganz, T. *Curr Opin Hematol* 9, 18-22 (2002); Harder, J., Glaser, R. & Schröder, J. M. *J Endotoxin Res* 13, 317-338 (2007); Zasloff, M. *Nature* 415, 389-395 (2002); Tossi, A., Sandri, L. & Giangaspero, *Biopolymers* 55, 4-30 (2000); Yount, N. Y., Bayer, A. S., Xiong, Y. Q. & Yeaman, M. R. *Biopolymers* (2006)). During recent years it has become increasingly evident that many cationic and amphipathic antimicrobial peptides, such as defensins and cathelicidins, are multifunctional, also mediating immunomodulatory roles and angiogenesis (Zanetti, M. *J Leukoc Biol* 75, 39-48 (2004); Elsbach, P. *J Clin Invest* 111, 1643-1645 (2003); Ganz, T. *Nat Rev Immunol* 3, 710-720 (2003)), thus motivating the recent and broader definition host defence peptides (HDP) for these members of the innate immune system. The family of HDPs has recently been shown to encompass various bioactive peptides with antimicrobial activities, including proinflammatory and chemotactic chemokines (Cole, A. M. et al. *J Immunol* 167, 623-627 (2001)), neuropeptides (Brogden, K. A. *Nat Rev Microbial* 3, 238-250 (2005)), peptide hormones (Kowalska, K., Carr, D. B. & Lipkowski, A. W. *Life Sci* 71, 747-750 (2002); Mor, A., Amiche, M. & Nicolas, P. Structure, *Biochemistry* 33, 6642-6650 (1994)), growth factors (Malmsten, M. et al. *Growth Factors* 25, 60-70 (2007)), the anaphylatoxin peptide C3a (Nordahl, E. A. et al. *Proc Natl Acad Sci USA* 101, 16879-16884 (2004); Pasupuleti, M. et al. Preservation of antimicrobial properties of complement peptide C3a, from invertebrates to humans. *J Biol Chem* 282, 2520-2528 (2007)), and kininogen-derived peptides (Frick, I. M. et al. *Embo J* 25, 5569-5578 (2006); Nordahl, E. A., Rydengard, V., Morgelin, M. & Schmidtchen, A. *J Biol Chem* 280, 34832-34839 (2005); Rydengard, V., Andersson Nordahl, E. & Schmidtchen, A. *Febs J* 273, 2399-2406 (2006)). Thus, fundamental and evolutionary conserved biological cascades, involving complement activation (Nordahl, E. A. et al. *Proc Natl Acad Sci USA* 101, 16879-16884 (2004)), kininogen degradation (Nordahl, E. A., Rydengard, V., Morgelin, M. & Schmidtchen, A. *J Biol Chem* 280, 34832-34839 (2005)) and contact activation (Frick, I. M. et al. *Embo J* 25, 5569-5578 (2006)), appear (in addition to their primary functions) to be characterized by a rudimentary generation of HDPs with a direct effect on bacteria.

The coagulation cascade also represents a fundamental system activated in response to injury and infection (Davie, E. W. & Kulman, J. D. *Semin Thromb Hemost* 32 Suppl 1, 3-15 (2006); Bode, W. The structure of thrombin: a janus-headed proteinase. *Semin Thromb Hemost* 32 Suppl 1, 16-31 (2006)). Through a series of cascade-like proteinase activation steps, thrombin is formed, leading to fibrinogen degradation and clot formation (Bode, W. *Semin Thromb Hemost* 32 Suppl 1, 16-31 (2006)). In addition, thrombin has other physiologic functions in hemostasis; i.e., mediating clot stabilization by activation of TAFI and activation of transglutaminase (FXIII), providing anticoagulant and antifibrinolytic activities in complex with thrombomodulin, and causing platelet aggregation due to PAR cleavage (Davie, E. W. & Kulman, J. D. *Semin Thromb Hemost* 32 Suppl 1, 3-15 (2006); Bode, W. *Semin Thromb Hemost* 32 Suppl 1, 16-31 (2006)). Moreover, thrombin elicits numerous cellular responses, including increased CAM expression and growth factor and cytokine release by endothelial cells, as well as growth stimulation of both smooth muscle and fibroblast cells (Bode, W. *Semin Thromb Hemost* 32 Suppl 1, 16-31 (2006)).

The antimicrobial activity of thrombin-derived peptides is described in WO 2007/091959. However, these thrombin-derived peptides have no known anti-inflammatory role.

The present invention seeks to provide new polypeptide agents for use in medicine, for example in the treatment or prevention of inflammation and/or excessive coagulation of the blood.

SUMMARY OF THE INVENTION

A first aspect of the invention provides a polypeptide comprising or consisting of an amino acid sequence from the C-terminal region of thrombin (i.e. factor II), or a fragment, variant, fusion or derivative thereof, or a fusion of said fragment, variant or derivative thereof, for use in the treatment or prevention of inflammation and/or excessive/unwanted coagulation of the blood, wherein the fragment, variant, fusion or derivative exhibits an anti-inflammatory activity and/or an anticoagulant activity.

The invention derives from the unexpected discovery by the inventors that S1 serine peptidase enzymes, such as thrombin, comprise "cryptic peptides" within their C-terminal region, which exhibit anti-inflammatory and anti-coagulant activity. It is believed that such peptides may be 'released' by cleavage of the parent peptidase holoprotein in response to wounding and other physiological challenges. Thus, the polypeptides of the invention constitute a novel and previously undisclosed class of HDPs, which have therapeutic potential against disorders and conditions associated with inflammation and coagulation.

By "S1 serine peptidase" we mean a class of enzymes that catalyse the hydrolysis of peptide bonds in proteins (EC 3.4.21.x). The peptidases of family S1 belong to the chymotrypsin family and contain the catalytic triad residues His, Asp and Ser in the active site. All of the characterised peptidases of the chymotrypsin family are endopeptidases. There are three main activity types: trypsin-like where there is cleavage of amide substrates following Arg or Lys at P1 of the substrate peptide, chymotrypsin-like where cleavage occurs following one of the hydrophobic amino acids at P1, and elastase-like with cleavage following an Ala at position P1. Substrate specificity in family S1 is dependent only on what is in the P1 position. The majority of the peptidases of this family enter the secretory pathway and have an N-terminal signal peptide. They are synthesized as precursors with an N-terminal extension that is cleaved to form the active enzyme. Activation does not always require the propeptide to be removed; in the blood coagulation factors cleavage may be sufficient, with the propeptide remaining bound by disulfide bridges as the heavy chain.

The S1 serine peptidases all share the same structural motif where the proteins are folded into two domains, each containing an open-ended beta barrel at right angles to each other (FIG. 2e). This crossing pattern of the beta strands in the barrel has been described as a "Greek Key". Thrombin, which is expressed by the liver and secreted in plasma cleaves bonds after Arg and Lys and converts fibrinogen to fibrin and activates factors V, VII, VIII, XIII, and, in complex with thrombomodulin, protein C. The carboxy terminus of all these proteins ends with an alpha helix (FIG. 2e).

S1 serine peptidases are described in Page & Cera, 2008, *Cell Mol Life Sci.* 65 (7-8):1220-36.

By "C-terminal region" we mean that the one hundred amino acids adjacent the C-terminus of the parent S1 serine peptidase. Thus, in a hypothetical S1 serine peptidase of 600 amino acids in length, wherein the amino acid sequence is specified in the conventional N-terminus to C-terminus direction, the C-terminal region corresponds to amino acid residues 501 to 600.

Thus, the polypeptides of the invention comprise or consist of a sequence of amino acids from within this C-terminal region of thrombin, and preferably at least 18 contiguous amino acids from within this region.

By "anti-inflammatory activity" we mean an ability to reduce or prevent one or more biological processes associated with inflammatory events. Such anti-inflammatory activity of polypeptides may be determined using methods well known in the art, for example by measuring LPS-induced release of pro-inflammatory cytokines from macrophages (e.g. TNFα, IL-6, MCP-1, IFN-γ), or in animal models of LPS-shock or bacterial infection (see Examples below), as well as release of the anti-inflammatory cytokine IL-10. Other relevant assays comprise effects of lipoteichoic acid, zymosan, DNA, RNA, flagellin or peptidoglycan in the above systems as well as determination of regulation at the transcriptional level (e.g. Gene-array, qPCR etc). Furthermore, dendritic cell activation or activation of thrombocytes, epithelial or mesechymal cells, mast cells, and neutrophils may also be used as a measure of anti-inflammatory activity.

By "anti-coagulant activity" we mean an ability to increase the prothrombin time (PT), the thrombin clotting time (TCT) and/or the activated partial thromboplastin time (aPTT). Alternatively, peripheral blood mononuclear cells (PB-MNC)s can be stimulated by *E. coli* LPS with or without the peptide and tissue factor and clot formation followed after addition of human plasma, or clotting times for whole blood can be measured.

It will be appreciated by persons skilled in the art that the thrombin may be from a human or non-human source. For example, the thrombin may be derived (directly or indirectly) from a non-human mammal, such as an ape (e.g. chimpanzee, bonobo, gorilla, gibbon and orangutan), monkey (e.g. madaque, baboon and colobus), rodent (e.g. mouse, rat) or ungulates (e.g. pig, horse and cow).

In one preferred embodiment, the thrombin is human thrombin (for example, see Swiss-Prot Accession No. P00734).

It will be appreciated by persons skilled in the art that the invention encompasses polypeptides comprising or consisting of an amino acid sequence from the C-terminal region of thrombin, as well as fragments, variants, fusions and derivatives of such amino acid sequence which retain an anti-inflammatory and/or anti-coagulant activity. Preferably, however, the polypeptide is not a naturally occurring protein (although it will, of course, be appreciated that the polypeptide may constitute an incomplete portion or fragment of a naturally occurring protein).

In one embodiment, the polypeptide comprises or consists of an amino acid sequence from the C-terminal region of thrombin.

In another embodiment, the polypeptide comprises an alpha helix domain. By "alpha helix domain" we mean an amino acid sequence which may adopt an alpha helix configuration under physiological conditions, and having an amphipathic character. It will be appreciated by persons skilled in the art that the alpha helix domain may adopt a helix configuration when in the parent holoprotein (under physiological conditions), but may not necessarily do so in the peptide of the invention.

For example, the amino acids in an alpha helix may be arranged in a right-handed helical structure where each amino acid corresponds to a 100° turn in the helix (i.e., the helix has 3.6 residues per turn), and a translation of 1.5 Å (=0.15 nm) along the helical axis. The pitch of the helix (the vertical distance between two points on the helix) is 5.4 Å (=0.54 nm) which is the product of 1.5 and 3.6. Most importantly, the N—H group of an amino acid forms a hydrogen bond with the C=O group of the amino acid four residues earlier; this repeated i+4 to i hydrogen bonding defines an alpha-helix. Residues in α-helices typically adopt backbone ($\phi$, $\psi$) dihedral angles around (−60°, −45°). More generally, they adopt dihedral angles such that the $\psi$ dihedral angle of one residue and the $\phi$ dihedral angle of the next residue sum to roughly −105°. Consequently, alpha-helical dihedral angles generally fall on a diagonal stripe on the Ramachandran plot (of slope −1), ranging from (−90°, −15° to (−35°, −70°).

In a further embodiment, the polypeptide comprises a heparin-binding domain. By "heparin-binding domain" we mean an amino acid sequence within the polypeptide which is capable of binding heparin under physiological conditions. The sequences often comprise XBBXB and XBBBXXB (where B=basic residue and X=hydropathic or uncharged residue), or clusters of basic amino acids (XBX, XBBX, XBBBX). Spacing of such clusters with non-basic residues (BXB, BXXB) may also occur. Additionally, a distance of approximately 20 Å between basic amino acids constitutes a prerequisite for heparin-binding.

However, in an alternative embodiment, the polypeptide does not comprise a heparin-binding domain.

One preferred embodiment of the first aspect of the invention provides polypeptides comprising or consisting of an amino acid sequence of SEQ ID NO:1

[SEQ ID NO: 1]
$X_1$-K-Y-G-F-Y-$X_2$-H-$X_3$-$X_4$-R-$X_5$-$X_6$-$X_7$-W-$X_8$-$X_9$-K-$X_{10}$ wherein
$X_1$, $X_2$, $X_3$, $X_4$, $X_5$, $X_6$, $X_7$ and $X_9$ independently represent any amino acid;
$X_8$ represents I or M
$X_{10}$ represents a sequence of any amino acids having a length of between 4 and 11 amino acids.

Advantageously, the polypeptide comprises, or consists of the amino acid sequence of SEQ ID NO: 2, or a fragment, variant, fusion or derivative of said sequence, or a fusion of said fragment, variant or derivative thereof:

"GKY25":

[SEQ ID NO: 2]

GKYGFYTHVFRLKKWIQKVIDQFGE

Thus, the polypeptide may comprise or consist of the amino acid sequence of SEQ ID NO: 2.

It will be appreciated by persons skilled in the art that the term 'amino acid', as used herein, includes the standard twenty genetically-encoded amino acids and their corresponding stereoisomers in the 'D' form (as compared to the natural form), omega-amino acids other naturally-occurring amino acids, unconventional amino acids (e.g., α,α-disubstituted amino acids, N-alkyl amino acids, etc.) and chemically derivatised amino acids (see below).

When an amino acid is being specifically enumerated, such as 'alanine' or 'Ala' or 'A', the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

In one embodiment, the polypeptides of the invention comprise or consist of L-amino acids.

Where the polypeptide comprises an amino acid sequence according to a reference sequence (for example, SEQ ID NO: 2), it may comprise additional amino acids at its N- and/or C-terminus beyond those of the reference sequence, for example, the polypeptide may comprise additional amino acids at its N-terminus. Likewise, where the polypeptide comprises a fragment, variant or derivative of an amino acid sequence according to a reference sequence, it may comprise additional amino acids at its N- and/or C-terminus.

In a further embodiment the polypeptide comprises or consists of a fragment of the amino acid sequence according to a reference sequence (for example, SEQ ID NO: 1 or 2). Thus, the polypeptide may comprise or consist of at least 5 contiguous amino acid of the reference sequence, for example at least 6, 7, 8, 9, 10, 11, 12, 13, 14, 15, 16, 17, 18, 19, 20, 21, 22, 23 or 24 contiguous amino acid of SEQ ID NO: 1 or 2. For example, the polypeptide may comprise or consist of at least 20 contiguous amino acids from SEQ ID NO: 1 or 2.

In one embodiment the polypeptide fragment commences at an amino acid residue selected from amino acid residues 1, 2, 3, 4, 5, 6, 7, 8, 9, 10, 11, 12, 13, 14, 15, 16, 17, 18, 19 and 20 of SEQ ID NO:2. Alternatively/additionally, the polypeptide fragment may terminate at an amino acid residue selected from amino acid residues 5, 6, 7, 8, 9, 10, 11, 12, 13, 14, 15, 16, 17, 18, 19, 20, 21, 22, 23, 24 and 25 of SEQ ID NO:2.

Exemplary polypeptide fragments of SEQ ID NO: 2 having anti-inflammatory and/or anti-microbial and/or anti-coagulant activity are described in the Examples below (e.g. see FIGS. 24, 25, 26 and 28 and related text).

Preferred polypeptide fragments of SEQ ID NO: 2 include the following:
(a) Polypeptides comprising or consisting of at least 11 contiguous amino acids from the N-terminus of SEQ ID NO: 1 or 2, for example at least 12, 13, 14, 15, 16, 17, 18, 19, 20, 21, 22, 23 or 24 contiguous amino acids therefrom;
(b) Polypeptides comprising or consisting of at least 13 contiguous amino acids from the C-terminus of SEQ ID NO: 1 or 2, for example at least 14, 15, 16, 17, 18, 19, 20, 21, 22, 23 or 24 contiguous amino acids therefrom; and
(c) Polypeptides comprising or consisting of at least amino acids 11 to 18 of SEQ ID NO: for 2, for example at least amino acids 10 to 19, 9 to 20, 8 to 21, 7 to 22, 6 to 23 or 5 to 24 therefrom.

Particularly preferred polypeptide fragments of SEQ ID NO: 2 include the following:

"GKY20":

[SEQ ID NO: 3]

GKYGFYTHVFRLKKWIQKVI;

"KYG201":

[SEQ ID NO: 4]

KYGFYTHVFRLKKWIQKVID;

"HVF18":

[SEQ ID NO: 5]

HVFRLKKWIQKVIDQFGE;

"VFR17":

[SEQ ID NO: 6]

VFRLKKWIQKVIDQFGE;
and

"FYT20":

[SEQ ID NO: 7]

FYTHVFRLKKWIQKVIDQFG.

It will be appreciated by persons skilled in the art that the polypeptide of the invention may comprise or consist of a variant of the amino acid sequence according to a reference sequence (for example, SEQ ID NOS: 1 to 7), or fragment of said variant. Such a variant may be a non-naturally occurring.

By 'variants' of the polypeptide we include insertions, deletions and substitutions, either conservative or non-conservative. For example, conservative substitution refers to the substitution of an amino acid within the same general class (e.g. an acidic amino acid, a basic amino acid, a non-polar amino acid, a polar amino acid or an aromatic amino acid) by another amino acid within the same class. Thus, the meaning of a conservative amino acid substitution and non-conservative amino acid substitution is well known in the art. In particular we include variants of the polypeptide which exhibit an anti-inflammatory activity.

In a further embodiment the variant has an amino acid sequence which has at least 50% identity with the amino acid sequence according to a reference sequence (for example, SEQ ID NOS: 1 to 7) or a fragment thereof, for example at least 55%, 60%, 65%, 70%, 75%, 80%, 85%, 90%, 95%, 96%, 97%, 98% or at least 99% identity.

Exemplary variants of fragments of the amino acid sequence of SEQ ID NO:2 are shown in FIG. 26.

The percent sequence identity between two polypeptides may be determined using suitable computer programs, for example the GAP program of the University of Wisconsin Genetic Computing Group and it will be appreciated that percent identity is calculated in relation to polypeptides whose sequences have been aligned optimally.

The alignment may alternatively be carried out using the Clustal W program (as described in Thompson et al., 1994, Nuc. Acid Res. 22:4673-4680, which is incorporated herein by reference).

The parameters used may be as follows:
Fast pairwise alignment parameters: K-tuple (word) size; 1, window size; 5, gap penalty; 3, number of top diagonals; 5. Scoring method: x percent.
Multiple alignment parameters: gap open penalty; 10, gap extension penalty; 0.05.
Scoring matrix: BLOSUM.

Alternatively, the BESTFIT program may be used to determine local sequence alignments.

In one embodiment, amino acids from the above reference sequences may be mutated in order to reduce proteolytic degradation of the polypeptide, for example by I,F to W modifications (see Strömstedt et al, *Antimicrobial Agents Chemother* 2009, 53, 593).

Variants may be made using the methods of protein engineering and site-directed mutagenesis well known in the art using the recombinant polynucleotides (see example, see *Molecular Cloning: a Laboratory Manual,* 3rd edition, Sambrook & Russell, 2000, Cold Spring Harbor Laboratory Press, which is incorporated herein by reference).

In one embodiment, the polypeptide comprises or consists of an amino acid which is a species homologue of any one of SEQ ID NOS: 2 to 7. By "species homologue" we include that the polypeptide corresponds to the same amino acid sequence within a thrombin protein from a non-human species, i.e. which polypeptide exhibits the maximum sequence identity with of any one of SEQ ID NOS: 2 to 7 (for example, as measured by a GAP or BLAST sequence comparison). Typically, the species homologue polypeptide will be the same length as the human reference sequence (i.e. SEQ ID NOS: 2 to 7).

In a still further embodiment, the polypeptide comprises or consists of a fusion protein.

By 'fusion' of a polypeptide we include an amino acid sequence corresponding to a reference sequence (for example, SEQ ID NOS: 1 to 7, or a fragment or variant thereof) fused to any other polypeptide. For example, the said polypeptide may be fused to a polypeptide such as glutathione-S-transferase (GST) or protein A in order to facilitate purification of said polypeptide. Examples of such fusions are well known to those skilled in the art. Similarly, the said polypeptide may be fused to an oligo-histidine tag such as His6 or to an epitope recognised by an antibody such as the well-known Myc tag epitope. In addition, fusions comprising a hydrophobic oligopeptide end-tag may be used. Fusions to any variant or derivative of said polypeptide are also included in the scope of the invention. It will be appreciated that fusions (or variants or derivatives thereof) which retain desirable properties, such as an anti-inflammatory activity, are preferred.

The fusion may comprise a further portion which confers a desirable feature on the said polypeptide of the invention; for example, the portion may be useful in detecting or isolating the polypeptide, or promoting cellular uptake of the polypeptide. The portion may be, for example, a biotin moiety, a streptavidin moiety, a radioactive moiety, a fluorescent moiety, for example a small fluorophore or a green fluorescent protein (GFP) fluorophore, as well known to those skilled in the art. The moiety may be an immunogenic tag, for example a Myc tag, as known to those skilled in the art or may be a lipophilic molecule or polypeptide domain that is capable of promoting cellular uptake of the polypeptide, as known to those skilled in the art.

It will be appreciated by persons skilled in the art that the polypeptide of the invention may comprise one or more amino acids that are modified or derivatised, for example by PEGylation, amidation, esterification, acylation, acetylation and/or alkylation.

As appreciated in the art, pegylated proteins may exhibit a decreased renal clearance and proteolysis, reduced toxicity, reduced immunogenicity and an increased solubility [Veronese, F. M. and J. M. Harris, Adv Drug Deliv Rev, 2002. 54 (4): p. 453-6., Chapman, A. P., Adv Drug Deliv Rev, 2002. 54 (4): p. 531-45.]. Pegylation has been employed for several protein-based drugs including the first pegylated molecules asparaginase and adenosine deaminase [Veronese, F. M. and J. M. Harris, Adv Drug Deliv Rev, 2002. 54 (4): p. 453-6., Veronese, F. M. and G. Pasut, Drug Discov Today, 2005. 10 (21): p. 1451-8.].

In order to obtain a successfully pegylated protein, with a maximally increased half-life and retained biological activity, several parameters that may affect the outcome are of importance and should be taken into consideration. The PEG molecules may differ, and PEG variants that have been used for pegylation of proteins include PEG and monomethoxy-PEG. In addition, they can be either linear or branched [Wang, Y. S., et al., Adv Drug Deliv Rev, 2002. 54 (4): p. 547-70]. The size of the PEG molecules used may vary and PEG moieties ranging in size between 1 and 40 kDa have been linked to proteins [Wang, Y. S., et al., Adv Drug Deliv Rev, 2002. 54 (4): p. 547-70., Sato, H., Adv Drug Deliv Rev, 2002. 54 (4): p. 487-504, Bowen, S., et al., Exp Hematol, 1999. 27 (3): p. 425-32, Chapman, A. P., et al., Nat Biotechnol, 1999. 17 (8): p. 780-3]. In addition, the number of PEG moieties attached to the protein may vary, and examples of between one and six PEG units being attached to proteins have been reported [Wang, Y. S., et al., Adv Drug Deliv Rev, 2002. 54 (4): p. 547-70., Bowen, S., et al., Exp Hematol, 1999. 27 (3): p. 425-32]. Furthermore, the presence or absence of a linker between PEG as well as various reactive groups for conjugation have been utilised. Thus, PEG may be linked to N-terminal amino groups, or to amino acid residues with reactive amino or hydroxyl groups (Lys, His, Ser, Thr and Tyr) directly or by using γ-amino butyric acid as a linker. In addition, PEG may be coupled to carboxyl (Asp, Glu, C-terminal) or sulfhydryl (Cys) groups. Finally, Gln residues may, be specifically pegylated using the enzyme transglutaminase and alkylamine derivatives' of PEG has been described [Sato, H., Adv Drug Deliv Rev, 2002. 54 (4): p. 487-504].

It has been shown that increasing the extent of pegylation results in an increased in vivo half-life. However, it will be appreciated by persons skilled in the art that the pegylation process will need to be optimised for a particular protein on an individual basis.

PEG may be coupled at naturally occurring disulphide bonds as described in WO 2005/007197. Disulfide bonds can be stabilised through the addition of a chemical bridge which does not compromise the tertiary structure of the protein. This allows the conjugating thiol selectivity of the two sulphurs comprising a disulfide bond to be utilised to create a bridge for the site-specific attachment of PEG. Thereby, the need to engineer residues into a peptide for attachment of to target molecules is circumvented.

A variety of alternative block copolymers may also be covalently conjugated as described in WO 2003/059973. Therapeutic polymeric conjugates can exhibit improved thermal properties, crystallisation, adhesion, swelling, coating, pH dependent conformation and biodistribution. Furthermore, they can achieve prolonged circulation, release of the bioactive in the proteolytic and acidic environment of the secondary lysosome after cellular uptake of the conjugate by pinocytosis and more favourable physicochemical properties due to the characteristics of large molecules (e.g. increased drug solubility in biological fluids). Block copolymers, comprising hydrophilic and hydrophobic blocks, form polymeric micelles in solution. Upon micelle disassociation, the individual block copolymer molecules are safely excreted.

Chemical derivatives of one or more amino acids may also be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

It will be further appreciated by persons skilled in the art that peptidomimetic compounds may also be useful. Thus, by 'polypeptide' we include peptidomimetic compounds which have an anti-inflammatory activity. The term 'peptidomimetic' refers to a compound that mimics the conformation and desirable features of a particular peptide as a therapeutic agent.

For example, the polypeptides of the invention include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al., (1997) *J. Immunol.* 159, 3230-3237, which is incorporated herein by reference. This approach involves making pseudopeptides containing changes involving the backbone, and not the orientation of side chains. Retro-inverse peptides, which contain NH—CO bonds instead of CO—NH peptide bonds, are much more resistant to proteolysis. Alternatively, the polypeptide of the invention may be a peptidomimetic compound wherein one or more of the amino acid residues are linked by a -y($CH_2NH$)— bond in place of the conventional amide linkage.

In a further alternative, the peptide bond may be dispensed with altogether provided that an appropriate linker moiety which retains the spacing between the carbon atoms of the amino acid residues is used; it may be advantageous for the linker moiety to have substantially the same charge distribution and substantially the same planarity as a peptide bond.

It will be appreciated that the polypeptide may conveniently be blocked at its N- or C-terminal region so as to help reduce susceptibility to exoproteolytic digestion.

A variety of uncoded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber et al., 1978, *Proc. Natl. Acad. Sci. USA* 75:2636 and Thursell et al., 1983, *Biochem. Biophys. Res. Comm.* 111:166, which are incorporated herein by reference.

A common theme among many of the synthetic strategies has been the introduction of some cyclic moiety into a peptide-based framework. The cyclic moiety restricts the conformational space of the peptide structure and this frequently results in an increased specificity of the peptide for a particular biological receptor. An added advantage of this strategy is that the introduction of a cyclic moiety into a peptide may also result in the peptide having a diminished sensitivity to cellular peptidases.

Thus, exemplary polypeptides of the invention comprise terminal cysteine amino acids. Such a polypeptide may exist in a heterodetic cyclic form by disulphide bond formation of the mercaptide groups in the terminal cysteine amino acids or in a homodetic form by amide peptide bond formation between the terminal amino acids. As indicated above, cyclising small peptides through disulphide or amide bonds between the N- and C-terminal region cysteines may circumvent problems of specificity and half-life sometime observed with linear peptides, by decreasing proteolysis and also increasing the rigidity of the structure, which may yield higher specificity compounds. Polypeptides cyclised by disulphide bonds have free amino and carboxy-termini which still may be susceptible to proteolytic degradation, while peptides cyclised by formation of an amide bond between the N-terminal amine and C-terminal carboxyl and hence no longer contain free amino or carboxy termini. Thus, the peptides of the present invention can be linked either by a C—N linkage or a disulphide linkage.

The present invention is not limited in any way by the method of cyclisation of peptides, but encompasses peptides whose cyclic structure may be achieved by any suitable method of synthesis. Thus, heterodetic linkages may include, but are not limited to formation via disulphide, alkylene or sulphide bridges. Methods of synthesis of cyclic homodetic peptides and cyclic heterodetic peptides, including disulphide, sulphide and alkylene bridges, are disclosed in U.S. Pat. No. 5,643,872, which is incorporated herein by reference. Other examples of cyclisation methods includes cyclization through click chemistry, epoxides, aldehyde-amine reactions, as well as and the methods disclosed in U.S. Pat. No. 6,008,058, which is incorporated herein by reference.

A further approach to the synthesis of cyclic stabilised peptidomimetic compounds is ring-closing metathesis (RCM). This method involves steps of synthesising a peptide precursor and contacting it with an RCM catalyst to yield a conformationally restricted peptide. Suitable peptide precursors may contain two or more unsaturated C—C bonds. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

Another approach, disclosed by D. H. Rich in *Protease Inhibitors*, Barrett and Selveson, eds., Elsevier (1986), which is incorporated herein by reference, has been to design peptide mimics through the application of the transition state analogue concept in enzyme inhibitor design. For example, it is known that the secondary alcohol of staline mimics the tetrahedral transition state of the scissile amide bond of the pepsin substrate.

In summary, terminal modifications are useful, as is well known, to reduce susceptibility by proteinase digestion and therefore to prolong the half-life of the peptides in solutions, particularly in biological fluids where proteases may be present. Polypeptide cyclisation is also a useful modification because of the stable structures formed by cyclisation and in view of the biological activities observed for cyclic peptides.

Thus, in one embodiment the polypeptide of the first aspect of the invention is linear. However, in an alternative embodiment, the polypeptide is cyclic.

It will be appreciated by persons skilled in the art that the polypeptides of the invention may be of various lengths.

Typically, however, the polypeptide is between 10 and 200 amino acids in length, for example between 15 and 150, 15 and 100, 15 and 50, 15 and 30, 15 and 25, or 18 and 25 amine acids in length. For example, the polypeptide may be at least 18 amino acids in length.

As stated at the outset, anti-inflammatory activity is a feature common to the polypeptides of the invention. In one embodiment, the polypeptides are capable of inhibiting the release of one or more pro-inflammatory cytokines from human monocyte-derived macrophages, including macrophage inhibitory factor, TNF-alpha, HMGB1, C5a, IL-17, IL-8, MCP-1, IFN-gamma, 11-6, IL-1b, IL-12. Antiinflammatory IL-10 may be transiently lowered, unaffected or increased.

Other markers may also be affected: these include tissue factor on monocytes and endothelial cells, procalcitonin, CRP, reactive oxygens species, bradykinin, nitric oxide, PGE1, platelet activating factor, arachidonic acid metabolites, MAP kinase activation In particular, the polypeptide may exhibit anti-inflammatory activity in one or more of the following models:
  (i) in vitro macrophage models using LPS, LTA, zymosan, flaggelin, dust mites, triacyl lipopeptides, glycolipids, human, viral or bacterial DNA or RNA, host derived glycosaminoglycan fragments, or bacterial peptidoglycan as stimulants;
  (ii) in vivo mouse models of endotoxin shock; and/or
  (iii) in vivo infection models, either in combination with antimicrobial therapy or used alone.

In a further embodiment of the invention, the polypeptide exhibits anticoagulant activity.

In a still further embodiment of the invention, the polypeptide exhibits Toll-like receptor (TLR) blocking activity. Such receptor blocking activity can be measured using methods well known in the art, for example by analysis of suitable down-stream effectors, such as iNOS activity, nuclear factor kappa B and cytokines.

By virtue of possessing an anti-inflammatory activity, the polypeptides of the first aspect of the invention are intended for use in the treatment or prevention of inflammation.

By "treatment or prevention of inflammation" we mean that the polypeptide of the invention is capable of preventing or inhibiting (at least in part) one or more symptom, signal or effect constituting or associated with inflammation.

It will be appreciated by persons skilled in the art that inhibition of inflammation may be in whole or in part. In a preferred embodiment, the polypeptide is capable of inhibiting one or more markers of inflammation by 20% or more compared to cells or individuals which have not been exposed to the polypeptide, for example by at least 30%, 40%, 50%, 60%, 70%, 80%, 90% or more.

In one embodiment, the polypeptides of the invention are capable of treating or preventing inflammation selectively.

By 'selectively' we mean that the polypeptide inhibits or prevents inflammation to a greater extent than it modulates other biological functions. For example, the polypeptide or fragment, variant, fusion or derivative thereof may inhibit or prevent inflammation only.

However, in a further embodiment, the polypeptide also (or alternatively) inhibits or prevents coagulation of the blood. As above, it will be appreciated by persons skilled in the art that inhibition of coagulation may be in whole or in part. In a preferred embodiment, the polypeptide is capable of inhibiting one or more measures and or markers of coagulation by 20% or more compared to cells or individuals which have not been exposed to the polypeptide, for example by at least 30%, 40%, 50%, 60%, 70%, 80%, 90% or more.

In one embodiment, the polypeptides are for use in the treatment or prevention of inflammation associated with (i.e. caused by or merely co-presenting with) an infection.

In preferred but non-limiting embodiments of the invention, the polypeptides are for use in the treatment or prevention of a disease, condition or indication selected from the following:
  i) Acute systemic inflammatory disease, with or without an infective component, such as systemic inflammatory response syndrome (SIRS), ARDS, sepsis, severe sepsis, and septic shock. Other generalized or localized invasive infective and inflammatory disease, including erysipelas, meningitis, arthritis, toxic shock syndrome, diverticulitis, appendicitis, pancreatitis, cholecystitis, colitis, cellulitis, burn wound infections, pneumonia, urinary tract infections, postoperative infections, and peritonitis.
  ii) Chronic inflammatory and or infective diseases, including cystic fibrosis, COPD and other pulmonary diseases, gastrointestinal disease including chronic skin and stomach ulcerations, other epithelial inflammatory and or infective disease such as atopic dermatitis, oral ulcerations (aphtous ulcers), genital ulcerations and inflammatory changes, parodontitis, eye inflammations including conjunctivitis and keratitis, external otitis, mediaotitis, genitourinary inflammations.
  iii) Postoperative inflammation. Inflammatory and coagulative disorders including thrombosis, DIC, postoperative coagulation disorders, and coagulative disorders related to contact with foreign material, including extracorporeal circulation, and use of biomaterials. Furthermore, vasculitis related inflammatory disease, as well as allergy, including allergic rhinitis and asthma.
  iv) Excessive contact activation and/or coagulation in relation to, but not limited to, stroke.
  v) Excessive inflammation in combination with antimicrobial treatment. The antimicrobial agents used may be administered by various routes; intravenous (iv), intraarterial, intravitreal, subcutaneous (sc), intramuscular (im), intraperitoneal (ip), intravesical, intratechal, epidural, enteral (including oral, rectal, gastric, and other enteral routes), or topically, (including dermal, nasal application, application in the eye or ear, eg by drops, and pulmonary inhalation). Examples of agents are penicillins, cephalosporins, carbacephems, cephamycins, carbapenems, monobactams, aminoglycosides, glycopeptides, quinolones, tetracyclines, macrolides, and fluoroquinolones. Antiseptic agents include iodine, silver, copper, clorhexidine, polyhexanide and other biguanides, chitosan, acetic acid, and hydrogen peroxide.

For example, the polypeptides may be for use in the treatment or prevention of an acute inflammation, sepsis, acute respiratory distress syndrome (ARDS), chronic obstructive pulmonary disease (COPD), cystic fibrosis, wounds, asthma, allergic and other types of rhinitis, cutaneous and systemic vasculitis, thrombosis and/or disseminated intravascular coagulation (DIC).

In one embodiment, the polypeptide exhibits both anti-inflammatory and anti-coagulant activity and may be used in the concomitant treatment or prevention of inflammation and coagulation. Such polypeptides may be particularly suited to the treatment and prevention of conditions where the combined inhibition of both inflammatory and coagulant processes is desirable, such as sepsis, chronic obstructive pulmonary disorder (COPD), thrombosis, DIC and acute respiratory distress syndrome (ARDS). Furthermore, other diseases associated with excessive inflammation and coagulation changes may benefit from treatment by the polypeptides, such as cystic fibrosis, asthma, allergic and other types of rhinitis, cutaneous and systemic vasculitis.

In a further embodiment, the polypeptides of the invention are for use in combination with one or more additional therapeutic agent. For example, the polypeptides of the invention may be administered in combination with antibiotic agents, anti-inflammatory agents, immunosuppressive agents and/or antiseptic agents, as well as vasoactive agents and/or receptor-blockers or receptor agonists. Exemplary antibiotic agents include anti-bacterial agents, anti-fungicides, anti-viral agents and anti-parasitic agents.

Thus, the peptides of the invention may serve as adjuvants (for blocking inflammation) to complement antibiotic, antiseptic and/or antifungal treatments of internal and external infections (such as erysipelas, lung infections including fungal infections, sepsis, COPD, wounds, and other epithelial infections). Likewise, the peptides of the invention may serve as adjuvants to antiseptic treatments, for example silver/PHMB treatment of wounds to quench LPS effects.

In one embodiment, the polypeptides of the invention are for use in combination with a steroid, for example a glucocorticoid (such as dexamethasone).

A second, related aspect of the invention provides an isolated polypeptide comprising or consisting of an amino acid sequence of SEQ ID NO: 1 or a fragment, variant, fusion or derivative thereof, or a fusion of said fragment, variant or derivative thereof, which exhibits an anti-inflammatory and/or anti-coagulant activity, with the proviso that the polypeptide is not a naturally occurring protein (e.g. holoprotein).

By "naturally occurring protein" in this context we mean that the polypeptide is synthesized de novo. However, fragments of such naturally occurring holoproteins generated in vivo are not excluded.

It will be appreciated by persons skilled in the art that terms such as fragment, variant, fusion or derivative should be construed as discussed above in relation to the first aspect of the invention.

In one embodiment, the polypeptide comprises or consists of an amino acid sequence selected from the group consisting of SEQ ID NOS: 1 to 7, or a fragment, variant, fusion or derivative of said sequence, or a fusion of said fragment, variant or derivative thereof (as described above in relation to the first aspect of the invention).

For example, the polypeptide may comprise or consist of an amino acid sequence selected from the group consisting of SEQ ID NOS: 1 to 7.

In a particularly preferred embodiment, the polypeptide comprises or consists of an amino acid sequence of SEQ ID NO:2, or a fragment, variant, fusion or derivative thereof which retains an anti-inflammatory activity of SEQ ID NO:2. For example, the polypeptide may comprise or consist of an amino acid sequence of SEQ ID NO:2.

It will be appreciated by persons skilled in the art that the optional features discussed above in relation to the polypeptides of the first aspect of the invention are also of relevance to the related polypeptides of the second aspect of the invention.

For example, in one preferred embodiment the polypeptide is capable of inhibiting the release of one or more pro-inflammatory cytokines from human monocyte-derived macrophages (such as IL-6, IFN-gamma, TNF-alpha, IL-12, IL-1 and/or IL-18), as well as promoting the transient release of anti-inflammatory IL-10.

In another preferred embodiment, the polypeptide exhibits anticoagulant activity.

The present invention also includes pharmaceutically acceptable acid or base addition salts of the above described polypeptides. The acids which are used to prepare the pharmaceutically acceptable acid addition salts of the aforementioned base compounds useful in this invention are those which form non-toxic acid addition salts, i.e. salts containing pharmacologically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maleate, fumarate, gluconate, saccharate, benzoate, methanesulphonate, ethanesulphonate, benzenesulphonate, p-toluenesulphonate and pamoate [i.e. 1,1'-methylene-bis-(2-hydroxy-3 naphthoate)] salts, among others.

Pharmaceutically acceptable base addition salts may also be used to produce pharmaceutically acceptable salt forms of the polypeptides. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others.

It will be appreciated that the polypeptides of the invention may be lyophilised for storage and reconstituted in a suitable carrier prior to use, e.g. through freeze drying, spray drying, spray cooling, or through use of particle formation (precipitation) from supercritical carbon dioxide. Any suitable lyophilisation method (e.g. freeze drying, spray drying, cake drying) and/or reconstitution techniques can be employed. It will be appreciated by those skilled in the art that lyophilisation and reconstitution can lead to varying degrees of activity loss and that use levels may have to be adjusted upward to compensate. Preferably, the lyophilised (freeze dried) polypeptide loses no more than about 1% of its activity (prior to lyophilisation) when rehydrated, or no more than about 5%, 10%, 20%, 25%, 30%, 35%, 40%, 45%, or no more than about 50% of its activity (prior to lyophilisation) when rehydrated.

Methods for the production of polypeptides of the invention are well known in the art.

Conveniently, the polypeptide is or comprises a recombinant polypeptide. Suitable methods for the production of such recombinant polypeptides are well known in the art, such as expression in prokaryotic or eukaryotic hosts cells (for example, see Sambrook & Russell, 2000, *Molecular Cloning, A Laboratory Manual*, Third Edition, Cold Spring Harbor, N.Y., the relevant disclosures in which document are hereby incorporated by reference).

Polypeptides of the invention can also be produced using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT transcription-translation system (Promega). This system has the advantage of producing suitable mRNA transcript from an encoding DNA polynucleotide in the same reaction as the translation.

It will be appreciated by persons skilled in the art that polypeptides of the invention may alternatively be synthesised artificially, for example using well known liquid-phase or solid phase synthesis techniques (such as t-Boc or Fmoc solid-phase peptide synthesis).

Thus, included within the scope of the present invention are the following:
(a) a third aspect of the invention provides an isolated nucleic acid molecule which encodes a polypeptide according to the second aspect of the invention;
(b) a fourth aspect of the invention provides a vector (such as an expression vector) comprising a nucleic acid molecule according to the third aspect of the invention;
(c) a fifth aspect of the invention provides a host cell comprising a nucleic acid molecule according to the third aspect of the invention or a vector according to the fourth aspect of the invention; and
(d) a sixth aspect of the invention provides a method of making a polypeptide according to the second aspect of the invention comprising culturing a population of host cells according to the fifth aspect of the invention under conditions in which said polypeptide is expressed, and isolating the polypeptide therefrom.

A seventh aspect of the invention provides a pharmaceutical composition comprising a polypeptide according to the first aspect of the invention together with a pharmaceutically acceptable excipient, diluent or carrier.

As used herein, 'pharmaceutical composition' means a therapeutically effective formulation for use in the treatment or prevention of disorders and conditions associated with inflammation.

As used herein, 'pharmaceutical composition' means a therapeutically effective formulation for use in the treatment or prevention of disorders and conditions associated with inflammation.

Additional compounds may also be included in the pharmaceutical compositions, such as other peptides, low molecular weight immunomodulating agents and antimicrobial agents. Other examples include chelating agents such as EDTA, citrate, EGTA or glutathione.

The pharmaceutical compositions may be prepared in a manner known in the art that is sufficiently storage stable and suitable for administration to humans and animals. The pharmaceutical compositions may be lyophilised, e.g. through freeze drying, spray drying, spray cooling, or through use of particle formation from supercritical particle formation.

By "pharmaceutically acceptable" we mean a non-toxic material that does not decrease the effectiveness of the biological activity of the active ingredients, i.e. the anti-inflammatory polypeptide(s). Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the peptide in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the peptide. The adjuvant may be one or more of colloidal silver, or zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition. The adjuvant may also be cationic polymers such as PHMB, cationic cellulose ethers, cationic cellulose esters, deacetylated hyaluronic acid, chitosan, cationic dendrimers, cationic synthetic polymers such as poly (vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, sucrose, mannitol, and cyclodextrines, which are added to the composition, e.g., for facilitating lyophilisation. Examples of polymers are starch, cellulose ethers, cellulose, carboxymethylcellulose, hydroxypropylmethyl cellulose, hydroxyethyl cellulose, ethylhydroxyethyl cellulose, ethyl cellulose, methyl cellulose, propyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, poly(lactic acid), poly(glycholic acid) or copolymers thereof with various composition, and polyvinylpyrrolidone, all of different molecular weight, which are added to the composition, e.g. for viscosity control, for achieving bioadhesion, or for protecting the active ingredient (applies to A-C as well) from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The pharmaceutical composition may also contain one or more mono- or di-saccharides such as xylitol, sorbitol, mannitol, lactitiol, isomalt, maititol or xylosides, and/or monoacylglycerols, such as monolaurin. The characteristics of the carrier are dependent on the route of administration. One route of administration is topical administration. For example, for topical administrations, a preferred carrier is an emulsified cream comprising the active peptide, but other common carriers such as certain petrolatum/mineral-based and vegetable-based ointments can be used, as well as polymer gels, liquid crystalline phases and microemulsions.

It will be appreciated that the pharmaceutical compositions may comprise one or more polypeptides of the invention, for example one, two, three or four different peptides. By using a combination of different peptides the anti-inflammatory effect may be increased.

As discussed above, the polypeptide may be provided as a salt, for example an acid adduct with inorganic acids, such as hydrochloric acid, sulfuric acid, nitric acid, hydrobromic acid, phosphoric acid, perchloric acid, thiocyanic acid, boric acid etc. or with organic acid such as formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, sulfanilic acid etc. Inorganic salts such as monovalent sodium, potassium or divalent zinc, magnesium, copper calcium, all with a corresponding anion, may be added to improve the biological activity of the antimicrobial composition.

The pharmaceutical compositions of the invention may also be in the form of a liposome, in which the polypeptide is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, to lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations is can be found in for example U.S. Pat. No. 4,235,871.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly (carprolactone) (PCL), and polyanhydrides have been widely used as biodegradable polymers in the production of microsheperes. Preparations of such microspheres can be found in U.S. Pat. No. 5,851,451 and in EP 213 303.

The pharmaceutical compositions of the invention may also be formulated with micellar systems formed by surfactants and block copolymers, preferably those containing poly (ethylene oxide) moieties for prolonging bloodstream circulation time.

The pharmaceutical compositions of the invention may also be in the form of polymer gels, where polymers such as starch, cellulose ethers, cellulose, carboxymethylcellulose, hydroxypropylmethyl cellulose, hydroxyethyl cellulose, ethylhydroxyethyl cellulose, ethyl cellulose, methyl cellulose, propyl cellulose, alginates, chitosan, carageenans, hyaluronic acid and derivatives thereof, polyacrylic acid, polyvinyl imidazole, polysulphonate, polyethylenglycol/polyethylene oxide, polyethylene-oxide/polypropylene oxide copolymers, polyvinylalcohol/polyvinylacetate of different degree of hydrolysis, and polyvinylpyrrolidone are used for thickening of the solution containing the peptide. The polymers may also comprise gelatin or collagen.

Alternatively, the polypeptides of the invention may be dissolved in saline, water, polyethylene glycol, propylene glycol, ethanol or oils (such as safflower oil, corn oil, peanut oil, cottonseed oil or sesame oil), tragacanth gum, and/or various buffers.

The pharmaceutical composition may also include ions and a defined pH for potentiation of action of anti-inflammatory polypeptides.

The compositions of the invention may be subjected to conventional pharmaceutical operations such as sterilisation and/or may contain conventional adjuvants such as preservatives, stabilisers, wetting agents, emulsifiers, buffers, fillers, etc., e.g., as disclosed elsewhere herein.

It will be appreciated by persons skilled in the art that the pharmaceutical compositions of the invention may be administered locally or systemically. Routes of administration include topical, ocular, nasal, pulmonary, buccal, parenteral (intravenous, subcutaneous, and intramuscular), oral, vaginal and rectal. Also administration from implants is possible. Suitable preparation forms are, for example granules, powders, tablets, coated tablets, (micro) capsules, suppositories, syrups, emulsions, microemulsions, defined as optically isotropic thermodynamically stable systems consisting of water, oil and surfactant, liquid crystalline phases, defined as systems characterised by long-range order but short-range disorder (examples include lamellar, hexagonal and cubic phases, either water- or oil continuous), or their dispersed counterparts, gels, ointments, dispersions, suspensions, creams, aerosols, droplets or injectable solution in ampule form and also preparations with protracted release of active compounds, in whose preparation excipients, diluents, adjuvants or carriers are customarily used as described above. The pharmaceutical composition may also be provided in bandages, plasters or in sutures or the like.

In preferred embodiments, the pharmaceutical composition is suitable for parenteral administration or topical administration.

In alternative preferred embodiments, the pharmaceutical composition is suitable for pulmonary administration or nasal administration.

For example, the pharmaceutical compositions of the invention can be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3, 3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a polypeptide of the invention and a suitable powder base such as lactose or starch.

Aerosol or dry powder formulations are preferably arranged so that each metered dose or 'puff' contains at least 0.1 mg of a polypeptide of the invention for delivery to the patient. It will be appreciated that the overall daily dose with an aerosol will vary from patient to patient, and may be administered in a single dose or, more usually, in divided doses throughout the day.

The pharmaceutical compositions will be administered to a patient in a pharmaceutically effective dose. By "pharmaceutically effective dose" is meant a dose that is sufficient to produce the desired effects in relation to the condition for which it is administered. The exact dose is dependent on the, activity of the compound, manner of administration, nature and severity of the disorder, age and body weight of the patient different doses may be needed. The administration of the dose can be carried out both by single administration in the form of an individual dose unit or else several smaller dose units and also by multiple administrations of subdivided doses at specific intervals.

The pharmaceutical compositions of the invention may be administered alone or in combination with other therapeutic agents, such as additional antibiotic, anti-inflammatory, immunosuppressive, vasoactive and/or antiseptic agents (such as anti-bacterial agents, anti-fungicides, anti-viral agents, and anti-parasitic agents). Examples of suitable antibiotic agents include penicillins, cephalosporins, carbacephems, cephamycins, carbapenems, monobactams, aminoglycosides, glycopeptides, quinolones, tetracyclines, macrolides, and fluoroquinolones. Antiseptic agents include iodine, silver, copper, clorhexidine, polyhexanide and other biguanides, chitosan, acetic acid, and hydrogen peroxide.

Likewise, the pharmaceutical compositions may also contain additional anti-inflammatory drugs, such as steroids and macrolactam derivatives.

In one embodiment, the pharmaceutical compositions of the invention are administered in combination with a steroid, for example a glucocorticoid (such as dexamethasone).

It will be appreciated by persons skilled in the art that the additional therapeutic agents may be incorporated as part of the same pharmaceutical composition or may be administered separately.

In one embodiment of the seventh aspect of the invention, the pharmaceutical composition is associated with a device or material to be used in medicine (either externally or internally). By 'associated with' we include a device or material which is coated, impregnated, covalently bound to or otherwise admixed with a pharmaceutical composition of the invention (or polypeptide thereof).

For example, the composition may be coated to a surface of a device that comes into contact with the human body or component thereof (e.g. blood), such as a device used in by-pass surgery, extracorporeal circulation, wound care and/or dialysis. Thus, the composition may be coated, painted, sprayed or otherwise applied to or admixed with a suture, prosthesis, implant, wound dressing, catheter, lens, skin graft, skin substitute, fibrin glue or bandage, etc. In so doing, the composition may impart improved anti-inflammatory and/or anti-coagulant properties to the device or material.

Preferably, the device or material is coated with the pharmaceutical composition of the invention (or the polypeptide component thereof). By 'coated' we mean that the pharmaceutical composition is applied to the surface of the device or material. Thus, the device or material may be painted or sprayed with a solution comprising a pharmaceutical composition of the invention (or polypeptide thereof). Alternatively, the device or material may be dipped in a reservoir of a solution comprising a polypeptide of the invention.

Advantageously, the device or material is impregnated with a pharmaceutical composition of the invention (or polypeptide thereof). By 'impregnated' we mean that the pharmaceutical composition is incorporated or otherwise mixed with the device or material such that it is distributed throughout.

For example, the device or material may be incubated overnight at 4° C. in a solution comprising a polypeptide of the invention. Alternatively, a pharmaceutical composition of the invention (or polypeptide thereof) may be immobilised on the device or material surface by evaporation, through use of supercritical carbon dioxide or by incubation at room temperature.

In an alternative embodiment, a polypeptide of the invention is covalently linked to the device or material, e.g. at the external surface of the device or material. Thus, a covalent bond is formed between an appropriate functional group on the polypeptide and a functional group on the device or material. For example, methods for covalent bonding of polypeptides to polymer supports include covalent linking via a diazonium intermediate, by formation of peptide links, by alkylation of phenolic, amine and sulphydryl groups on the binding protein, by using a poly functional intermediate e.g. glutardialdehyde, and other miscellaneous methods e.g. using silylated glass or quartz where the reaction of trialkoxysilanes permits derivatisation of the glass surface with many different functional groups. For details, see Enzyme immobilisation by Griffin, M., Hammonds, E. J. and Leach, C. K (1993) In *Technological Applications of Biocatalysts* (BIOTOL SERIES), pp. 75-118, Butterworth-Heinemann. See also the review article entitled 'Biomaterials in Tissue Engineering' by Hubbell, J. A. (1995) *Science* 13:565-576.

In a preferred embodiment, the device or material comprise or consists of a polymer. The polymer may be selected from the group consisting of polyesters (e.g. polylactic acid, polyglycolic acid or poly lactic acid-glycolic acid copolymers of various compositions), polyorthoesters, polyacetals, polyureas, polycarbonates, polyurethanes, polyamides) and polysaccharide materials (e.g. cross-linked alginates, hyaluronic acid, carageenans, gelatines, starch, cellulose derivatives).

Alternatively, or in addition, the device or material may comprise or consists of metals (e.g. titanium, stainless steel, gold, titanium), metal oxides (silicon oxide, titanium oxide) and/or ceramics (apatite, hydroxyapatite).

Such materials may be in the form of macroscopic solids/monoliths, as chemically or physicochemically cross-linked gels, as porous materials, or as particles.

Thus, the present invention additionally provides devices and materials to be used in medicine, to which have been applied a polypeptide of the invention or pharmaceutical composition comprising the same.

Such devices and materials may be made using methods well known in the art.

An eighth aspect of the invention provides polypeptide according to the second aspect of the invention or a pharmaceutical composition according to the seventh aspect of the invention for use in medicine, for example in the treatment or prevention of inflammation and/or excessive coagulation.

In preferred embodiments, the polypeptide according to the second aspect of the invention or the pharmaceutical composition according to the seventh aspect of the invention are for use in the treatment and/prevention of a disease, condition or indication selected from the following:

i) Acute systemic inflammatory disease, with or without an infective component, such as systemic inflammatory response syndrome (SIRS), ARDS, sepsis, severe sepsis, and septic shock. Other generalized or localized invasive infective and inflammatory disease, including erysipelas, meningitis, arthritis, toxic shock syndrome, diverticulitis, appendicitis, pancreatitis, cholecystitis, colitis, cellulitis, burn wound infections, pneumonia, urinary tract infections, postoperative infections, and peritonitis.

ii) Chronic inflammatory and or infective diseases, including cystic fibrosis, COPD and other pulmonary diseases, gastrointestinal disease including chronic skin and stomach ulcerations, other epithelial inflammatory and or infective disease such as atopic dermatitis, oral ulcerations (aphtous ulcers), genital ulcerations and inflammatory changes, parodontitis, eye inflammations including conjunctivitis and keratitis, external otitis, mediaotitis, genitourinary inflammations.

iii) Postoperative inflammation. Inflammatory and coagulative disorders including thrombosis, DIC, postoperative coagulation disorders, and coagulative disorders related to contact with foreign material, including extracorporeal circulation, and use of biomaterials. Furthermore, vasculitis related inflammatory disease, as well as allergy, including allergic rhinitis and asthma.

iv) Excessive contact activation and/or coagulation in relation to, but not limited to, stroke.

v) Excessive inflammation in combination with antimicrobial treatment. The antimicrobial agents used may be administered by various routes; intravenous (iv), intraarterial, intravitreal, subcutaneous (sc), intramuscular (im), intraperitoneal (ip), intravesical, intratechal, epidural, enteral (including oral, rectal, gastric, and other enteral routes), or topically, (including dermal, nasal application, application in the eye or ear, eg by drops, and pulmonary inhalation). Examples of agents are penicillins, cephalosporins, carbacephems, cephamycins, carbapenems, monobactams, aminoglycosides, glycopeptides, quinolones, tetracyclines, macrolides, and fluoroquinolones. Antiseptic agents include iodine, silver, copper, clorhexidine, polyhexanide and other biguanides, chitosan, acetic acid, and hydrogen peroxide.

For example, the polypeptides may be for use in the treatment or prevention of an acute inflammation, sepsis, acute respiratory distress syndrome (ARDS), chronic obstructive pulmonary disease (COPD), cystic fibrosis, wounds, asthma, allergic and other types of rhinitis, cutaneous and systemic vasculitis, thrombosis and/or disseminated intravascular coagulation (DIC).

In particularly preferred embodiments, a polypeptide comprising or consisting of the amino acid sequence of SEQ ID NO: 1, 2, 3, 4, 5, 6 or 7, or a fragment, variant, fusion or derivative of said sequence, or a fusion of said fragment, variant or derivative thereof which retains the anti-inflammatory and/or anti-coagulant activity thereof, is for use in the treatment or prevention of bacterial sepsis (e.g. P. aeruginosa sepsis) and/or endotoxin-mediated shock. Optionally, the polypeptide may be used in combination with a conventional antibiotic agent (such as those discussed above).

A related ninth aspect of the invention provides the use of a polypeptide according to the second aspect of the invention or a pharmaceutical composition according to the seventh aspect of the invention in the preparation of a medicament for the treatment or prevention of inflammation and/or excessive coagulation (as described above).

A tenth aspect of the invention provides a method for treating or preventing inflammation and/or coagulation in a patient, the method comprising administering to the patient a therapeutically-effective amount of a polypeptide according to the second aspect of the invention or a pharmaceutical composition according to the seventh aspect of the invention (as described above). In preferred but non-limiting embodiments, the method is for the treatment or prevention of disease, condition or indication as listed above, for example an acute inflammation, sepsis, acute respiratory distress syndrome (ARDS), chronic obstructive pulmonary disease (COPD), cystic fibrosis, asthma, allergic and other types of rhinitis, cutaneous and systemic vasculitis, thrombosis and/or disseminated intravascular coagulation (DIC).

Persons skilled in the art will further appreciate that the uses and methods of the present invention have utility in both the medical and veterinary fields. Thus, the polypeptide medicaments may be used in the treatment of both human and non-human animals (such as horses, dogs and cats). Advantageously, however, the patient is human.

Preferred aspects of the invention are described in the following non-limiting examples, with reference to the following figures:

(A) Degradation of the proteins was performed at 37° C. for the indicated time periods. RDA was performed in low-salt conditions with E. coli as test organism. Each 4 mm-diameter well was loaded with 6 µl of the solution (corresponding to 3.6 µg protein). The bar diagrams indicate the diameter of the zones of clearance obtained (in mm). The inset visualizes the results obtained with prothrombin. C, buffer; NE, neutrophil elastase only. LL-37 (100 µM) was included for comparison. (B) Intact prothrombin (PT) and thrombin (T), and cleavage products from the different incubations with neutrophil elastase (NE, indicated above) were analyzed by SDS-PAGE (16.5% Tris-Tricine gel). The gels are overloaded (12 µg) in order to visualize generation of fragments of low molecular masses. Rightmost two lanes show PT and T proteins at 2 µg.

Figure 2:
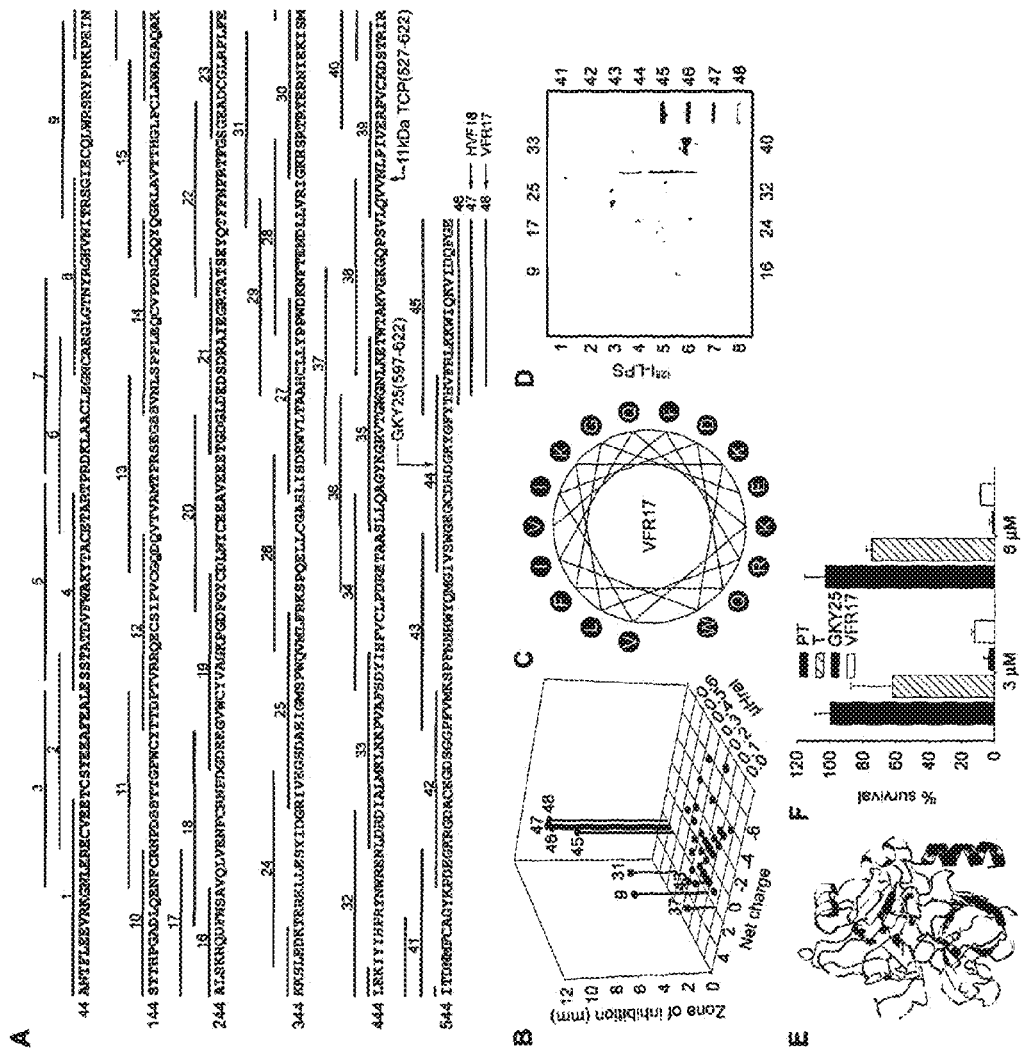

FIG. 2. Activities of peptides derived from prothrombin.

(A) Sequence of prothrombin [SEQ ID NO:31] and overlapping peptides (indicated by numbers). The color markings indicate antimicrobial regions. In addition to the regular overlapping peptides, peptide regions of high net charge, and/or content of predicted helical regions (Agadir; see worldwide web at embl-heidelberg.de/Services/Serrano/Agadir-start.html) were selected. Peptides described in subsequent experiments are also indicated; GKY25, VFR17, and the major ~11 kDa peptide (amino acids 527-622). (B) Overlapping peptides of prothrombin were analysed for antimicrobial activities against E. coli. The inhibitory zones, relative hydrophobic moment (µHrel) as well as net charge of respective peptides (only active peptides are numbered) are indicated in the 3-D graph. For determination of antibacterial activities, E. coli ($4 \times 10^6$ cfu) was inoculated in 0.1% TSB agarose gel. Each 4 mm-diameter well was loaded with 6 µl of peptide (at 100 µM). The zones of clearance correspond to the inhibitory effect of each peptide after incubation at 37° C. for 18-24 h (mean values are presented, n=3). (C) Helical wheel representation of the C-terminal peptide VFR17. The amino acids are indicated. (D) LPS-binding activity of the prothrombin-derived peptide sequences. Peptides (5 µg) were applied to nitrocellulose membranes followed by incubation in PBS (containing 2% bovine serum albumin) with iodinated ($^{125}$I)-LPS. Only peptides from the C-terminal part of prothrombin demonstrated significant binding to LPS. (E) Molecular model of thrombin. The peptides GKY25 (indicated in FIG. 2A) and VFR17 (peptide 48 n FIG. 2A) are indicated in the crystal structure of human thrombin (PDB code 1C5L). (F) Activities of prothrombin (PT), thrombin (T), GKY25 and VFR17 on E. coli ATCC 25922. In viable count assays GKY25 and VFR17 displayed significant antibacterial activities. $2 \times 10^6$ cfu/ml of bacteria were incubated in 50 µl with proteins and peptides at a concentration of 3 and 6 µM, respectively.

Figure 3:
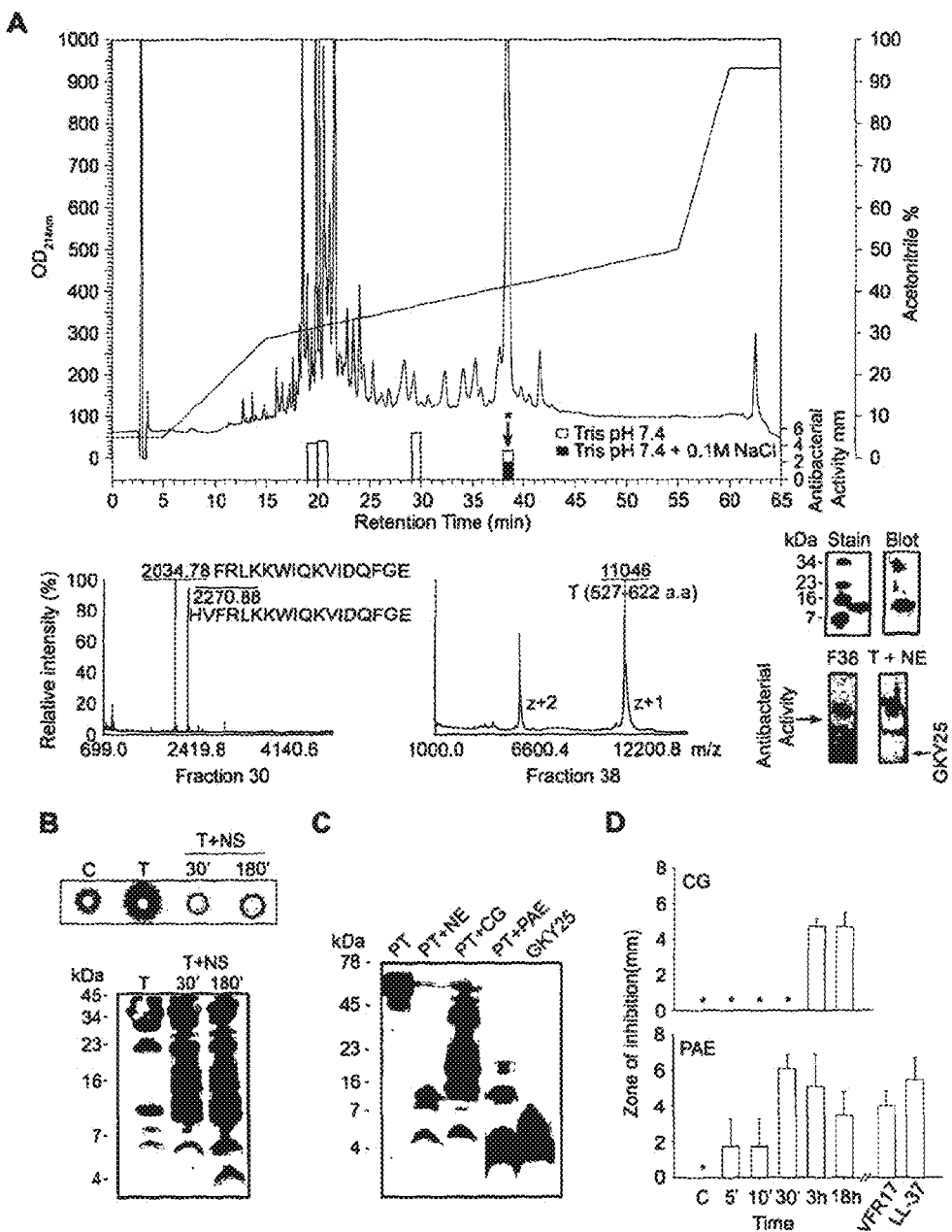

FIG. 3. Identification of antibacterial regions of thrombin and prothrombin.

(A) RP-HPLC separation of thrombin digested with neutrophil elastase. The bars indicate the antibacterial activity of the fractions in low (gray) as well as high salt conditions (black). Fraction 30 (lower left) contained two peaks of masses 2034.78 and 2270.88, perfectly matching the indicated sequences obtained after ESI-MS/MS analysis. Fraction 38 was analysed by MALDI-MS, and subsequently by ESI-MS [SEQ ID NOs:9 and 51]. The ESI-MS analysis identified a dominant mass of 11041 corresponding to the 96-amino acid long peptide N527-E622 (indicated in FIG. 2A) with two intact disulphide bridges. A minor mass corresponding to V528-E622 was also detected by ESI-MS/MS. N- and C-terminal sequencing yelded NLPI and EGFQ, respectively. The rightmost insets illustrate the ~11 kDa peptide analysed by SDS-PAGE and stained for protein (stain), or after immunoblot (blot), and below, the peptide (F38) was analyzed by gel-overlay for detection of antibacterial activity. The activity of F38 was identical to the major clearing zone generated by elastase-digested thrombin (T+NE). Right arrow indicates the position of clearing zone generated by the peptide GKY25. The gel was run top to bottom. Finally, peptides of fractions 20-21 were predicted using the FIND-PEPT tool (www.expasy.org/tools/findpept.html) (Table S1). (B) Degradation of thrombin by neutrophil supernatants generates antibacterial activity in RDA (upper inset). RDA was performed in low-salt conditions. $E.\ coli$ ($4 \times 10^6$ cfu) was used as test organism. Each 4 mm-diameter well was loaded with 6 μl of material (C, supernatant only; T, thrombin only; T+NS; thrombin incubated for 30 and 180 min respectively, with neutrophil supernatants). The digests were analysed by SDS-PAGE (16.5 Tris-Tricine gels) and immunoblotting with antibodies against VFR17 (lower panel). (C) Prothrombin was digested with the enzymes as indicated for 3 h, and analysed by SDS-PAGE (16.5 Tris-Tricine gels) and immunoblotting using antibodies against VFR17 (NE, neutrophil elastase; CG, cathepsin G; PAE, $P.\ aeruginosa$ elastase). (D) RDA results of prothrombin digested with cathepsin G (CG) and $P.\ aeruginosa$ elastase (PAE) for different time periods. VFR17 and LL-37 (10 μM) are shown for comparison.

Figure 4:
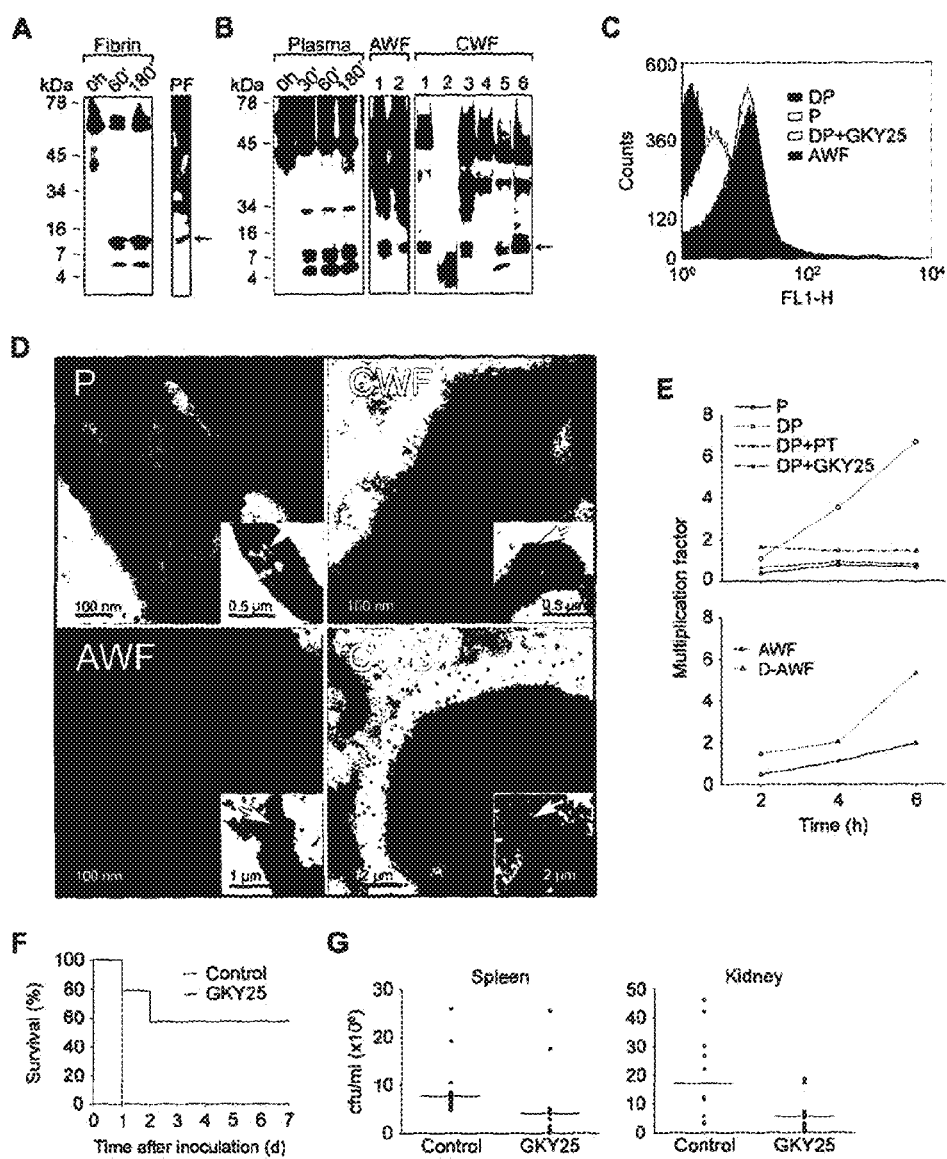

FIG. 4. Thrombin-derived C-terminal peptides, their presence and antimicrobial effects ex vivo and in vivo.

(A) Fibrin clots were produced from human plasma and incubated with neutrophil elastase for the indicated time periods (Fibrin), or obtained from a patient with a venous, non-infected, chronic ulcers (PF), extracted, and analyzed by immunoblotting using polyclonal antibodies against the thrombin C-terminal peptide VFR17. (B) Human plasma, incubated with neutrophil elastase for the indicated time periods (Plasma, left panel), acute wound fluid (patients 1-2, AWF, middle panel), or wound fluid from patients with chronic ulcers (patients 1-6, CWF, right panel) was analysed by Western blot using polyclonal antibodies against the thrombin C-terminal peptide VFR17. (C) Flow cytometry analysis of binding of C-terminal thrombin, epitopes to $P.\ aeruginosa$ bacteria. Bacteria were incubated for 4 h with control plasma (P), human plasma depleted of prothrombin (DP), depleted plasma supplemented with the peptide GKY25, or, acute wound fluid (AWF). Binding of C-terminal epitopes to the bacteria was detected using primary antibodies against the C-terminal epitope VFR17 followed by addition of FITC-labeled secondary antibodies. (D) Visualization of binding and membrane damage by TCPs. $P.\ aeruginosa$ bacteria were incubated ex vivo with human plasma (P), acute wound fluid (AWF), or wound fluid from a chronic leg ulcer (CWF), or visualized in vivo in fibrin slough (CWS) derived from a patient with a chronic ulcer infected by $S.\ aureus$. Arrows in P, AWF, and CWF point to damaged bacterial membranes Coccoid bacteria (indicated by an arrow in CWS) show extensive binding of antibodies directed against the C-terminal peptide VFR17 (negative and positive bacterial controls, and additional material are found in FIGS. 9 and 10). (E) TCPs inhibit bacterial growth in human plasma. Control plasma (P), plasma depleted of prothrombin (DP), depleted plasma supplemented with either prothrombin (DP+PT), or GKY25 (DP+GKY25) (PT and GKY25 at 1.5 μM), or control AWF or depleted AWF (D-AWF), were inoculated with $P.\ aeruginosa$ bacteria under similar conditions as in (C-D). The multiplication factors at various time points are given. After incubation, CFUs were determined by plating. Experiments were repeated three times and a representative experiment is shown. (F) The thrombin C-terminal peptide GKY25 significantly increases survival. Mice were i.p. injected with $P.\ aeruginosa$ bacteria, followed by subcutaneous injection of GKY25 or buffer only, after 1 h and then with intervals of 24 h for the three following days. Treatment with the peptide significantly increased survival (n=10 for controls and treated, p=0.002). (G) GKY25 suppresses bacterial dissemination to the spleen and kidney. Mice were infected as above, GKY25 was administrated subcutaneously after 1 h, and the cfu of $P.\ aeruginosa$ in spleen and kidney was determined after a time period of 8 h (n=10 for controls and treated, P<0.05 for spleen and kidney. Horizontal line indicates median value).

Figure 5:
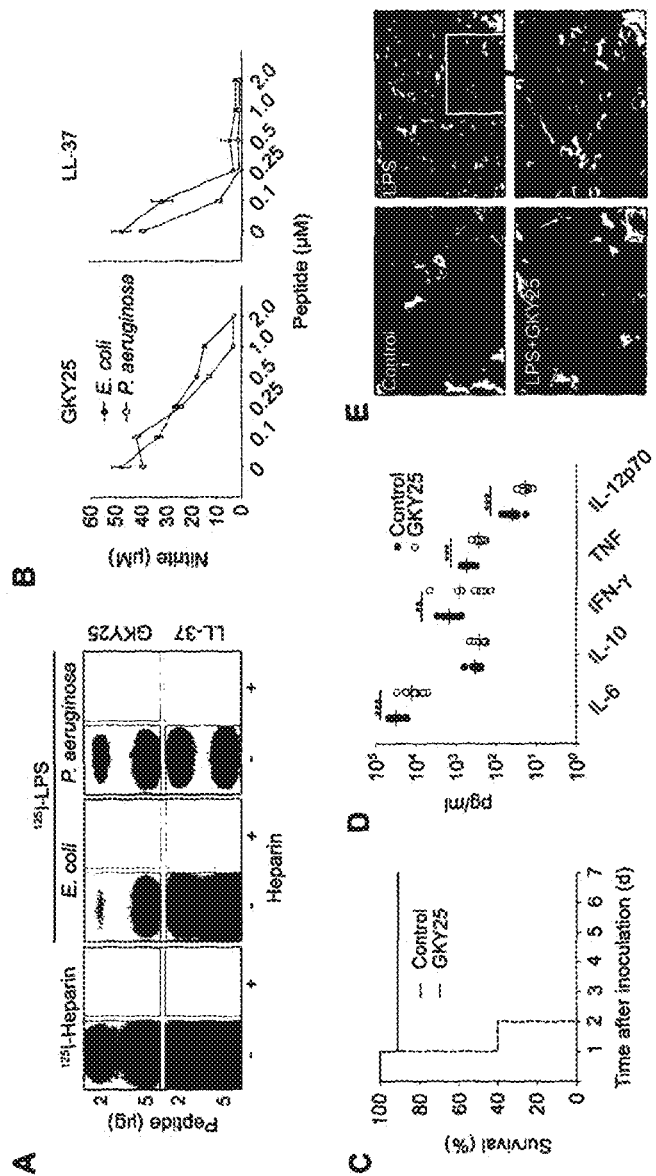

FIG. 5. LPS-binding and immunomodulatory role in vitro and in vivo of thrombin-derived C-terminal peptides.

(A) GKY25 binds heparin and LPS. 2 and 5 μg GKY25 were applied to nitrocellulose membranes. These membranes were then blocked in PBS (containing 2% bovine serum albumin) for 1 h at room temperature and incubated in PBS-with iodinated ($^{125}$I) heparin or LPS. Unlabeled heparin (6 mg/ml) (+) was added for competition of binding. LL-37 was used for comparison. The membranes were washed (3×10 min in PBS). A Bas 2000 radioimaging system (Fuji) was used for visualization of radioactivity. (B) GKY25 inhibits NO production. RAW264.7 macrophages were stimulated with LPS from $E.\ coli$ and $P.\ aeruginosa$, in presence of GKY25 at the indicated concentrations. LL-37 is presented for comparison. (C) GKY25 significantly increases survival in LPS-induced shock. Mice were injected with LPS followed by intraperitoneal administration of GKY25 (200 μg). Survival was followed for 7 days. (n=9 for controls, n=10 for treated animals, P<0.001). (D) GKY25 attenuates proinflammatory cytokines. In a separate experiment, mice were sacrificed 6 hours after i.p. injection of LPS followed by treatment with GKY25 (200 μg) or buffer, and the indicated cytokines were analysed in blood (n=9 for controls, n=10 for treated animals, the P values for the respective cytokines are IL-6, 0.001; IFN-γ=0.009; TNF, 0.001; IL-12p70, 0.001. IL-10 was not significant.). (E) Lungs were analyzed by scanning electron microscopy 20 h after LPS injection i.p. followed by treatment with GKY25 (200 μg) or buffer. Treatment with the peptides blocked leakage of proteins and erythrocytes (see inset) (n=3 in both groups, and a representative lung section is shown).

Figure 6:
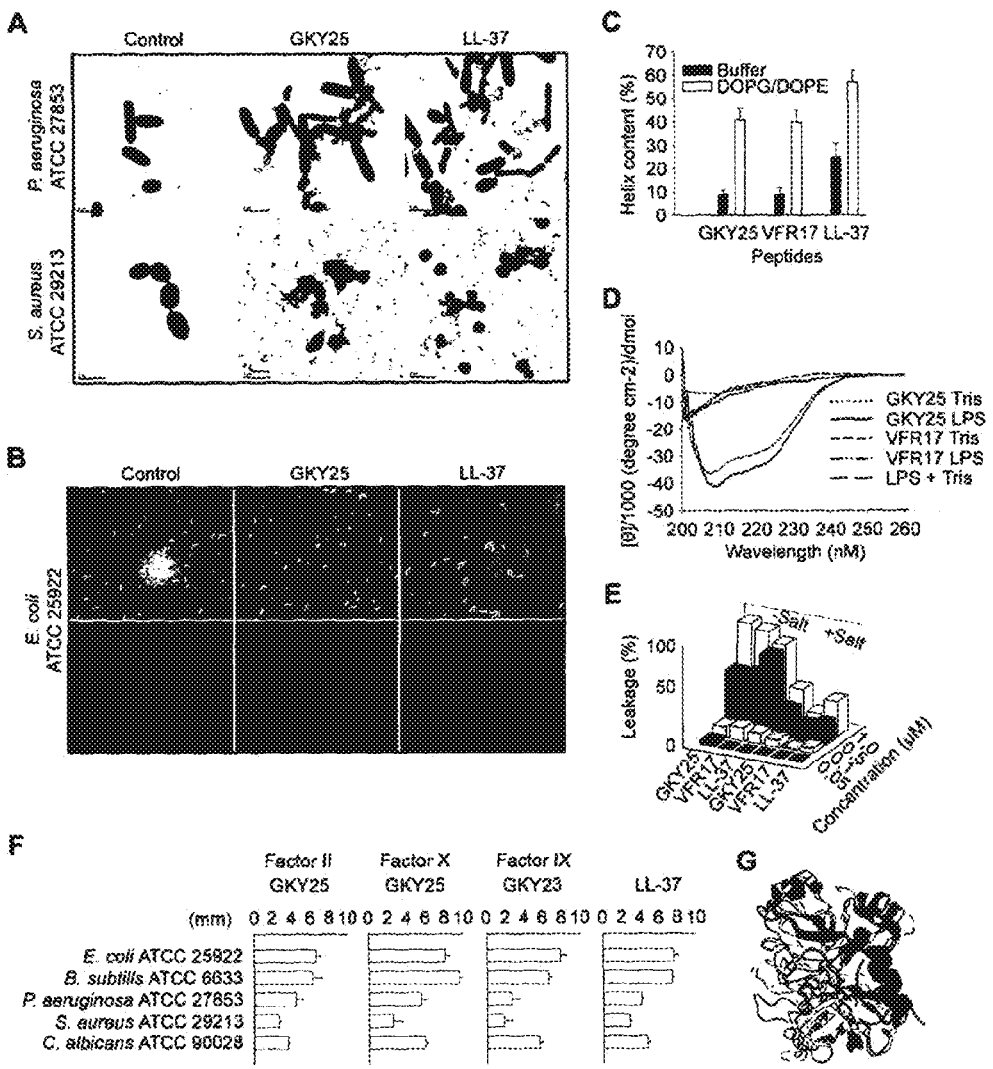

FIG. 6. Mode of action of thrombin-derived C-terminal peptides.

(A) Electron microscopy analysis. $P.\ aeruginosa$ and $S.\ aureus$ bacteria was incubated for 2 h at 37° C. with 30 μM of GKY25 and LL-37 and analysed with electron microscopy. Scale bar represents 1 μm. Control; Buffer control. (B) Permeabilizing effects of peptides on $E.\ coli$. Bacteria was incubated with the indicated peptides at 30 μM and permeabilization was assessed using the impermeant probe FITC. (C) Helical content of the thrombin-derived C-terminal peptides GKY25 and VFR17 in presence of negatively charged liposomes (DOPE/DOPG). The two peptides showed a marked helix induction upon addition of the liposomes. (D) CD spectra of GKY25 and VFR17 in Tris-buffer and in presence of LPS. For control, CD spectra for buffer and LPS alone are also presented. (E) Effects of the indicated peptides on liposome leakage. The membrane permeabilizing effect was recorded by measuring fluorescence release of carboxyfluorescein from DOPE/DOPG (negatively charged) liposomes. The experiments were performed in 10 mM Tris-buffer, in absence and presence of 0.15 M NaCl. Values represents mean of triplicate samples. (F) Activities of corresponding C-terminal peptides of the indicated coagulation factors. Peptides were tested in RDA against the indicated bacteria. Bacteria ($4 \times 10^6$ cfu) was inoculated in 0.1% TSB agarose gels. Each 4 mm-diameter well was loaded with 6 μl of peptide at 100 μM. The zones of clearance correspond to the inhibitory effect of each peptide after incubation at 37° C. for 18-24 h.

(G) Overlay 3D-model showing the three coagulation factors thrombin, and factor X and IX. The C-terminal parts are indicated.

Figure 7:
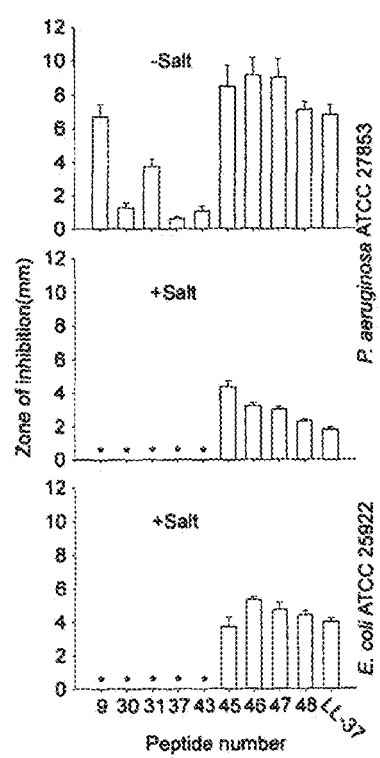

FIG. 7. Antimicrobial activities.

Activities of peptides (RDA) of prothrombin-derived peptides against *P. aeruginosa* in absence and presence of 0.1 M NaCl, and against *E. coli* in 0.1 M NaCl. Each 4 mm-diameter well was loaded with 6 μl of the Solution. The bar diagrams indicate the zones of clearance obtained (in mm).

Figure 8:
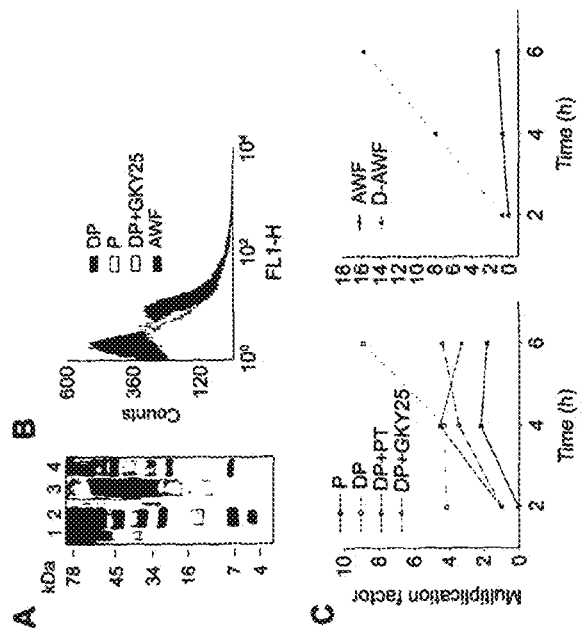

FIG. 8. TCPs are formed and bind to and inhibit microbes in plasma environment.

(A) Overnight cultures of *P. aeruginosa* 15159 bacteria were washed, resuspended, and incubated with citrate plasma or a preformed fibrin clot for 4 h at 37° C. The bacterial cells were collected, washed with PBS, and bound proteins and corresponding supernatants were subjected to Tris-Tricine SDS-PAGE under reducing conditions, followed by immunoblotting with antibodies recognizing the C-terminal part of thrombin. 1 and 2, unbound and bound material in plasma; 3 and 4, unbound and bound material after incubation with fibrin. (B) Flow cytometry analysis of binding of C-terminal thrombin epitopes to *S. aureus* bacteria. Bacteria were incubated for 4 h with control plasma (P), human plasma depleted of prothrombin (DP), depleted plasma supplemented with the peptide GKY25 or, acute wound fluid (AWF). Binding of C-terminal epitopes to the bacteria was detected using primary antibodies against the C-terminal epitope VFR17 followed by addition of FITC-labeled secondary antibodies. Absence of detectable binding of FITC-labeled secondary antibodies to *S. aureus* in prothrombin-depleted plasma, excludes any significant influence of unspecific Protein A based interactions in this experimental system. (C) TCPs inhibit growth of *S. aureus* in human plasma. Similarly as in FIG. 4E, control plasma (P), plasma depleted of prothrombin (DP), depleted plasma supplemented with either prothrombin (DP+PT), or GKY25 (DP+GKY25) (both at 1.5 μM) were inoculated with *S. aureus* bacteria under similar conditions as in (B-D), shown to result in generation of TCPs, bacterial binding, and membrane damage. The multiplication factors at various time points are given. After incubation, CFUs were determined by plating. Experiments were repeated three times and a representative experiment is shown.

Figure 9:
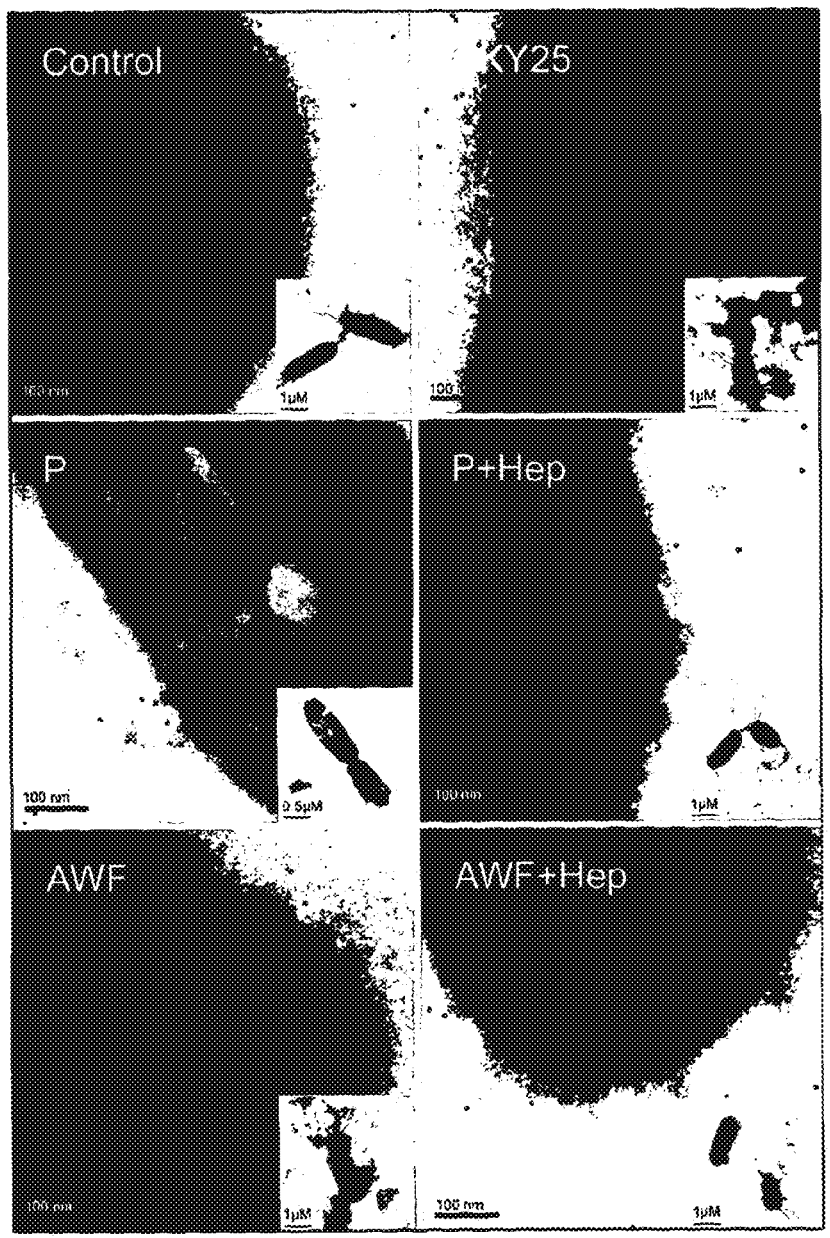

FIG. 9. TCPs bind and damage bacteria.

Visualization of binding and membrane damage by TCPs. *P. aeruginosa* bacteria alone (Control) or after incubation with 1.5 μM of GKY25, were analyzed by electron microscopy following negative staining. P+Hep and AWF+Hep indicate the results obtained after addition of 100 μg/ml heparin during the incubation with human plasma and acute wound fluid, respectively. Absence of TCPs at bacterial surfaces as well as membrane damage was noted in the heparin-treated material. Examination of at least 50 different bacterial profiles demonstrated a significant difference between immunogold binding in P and AWF sections and corresponding material with heparin. Thus >80% of gold particles were associated with bacterial surfaces in P and AWF, whereas the material supplemented with heparin contained a low background of particles distributed unspecifically.

Figure 10:
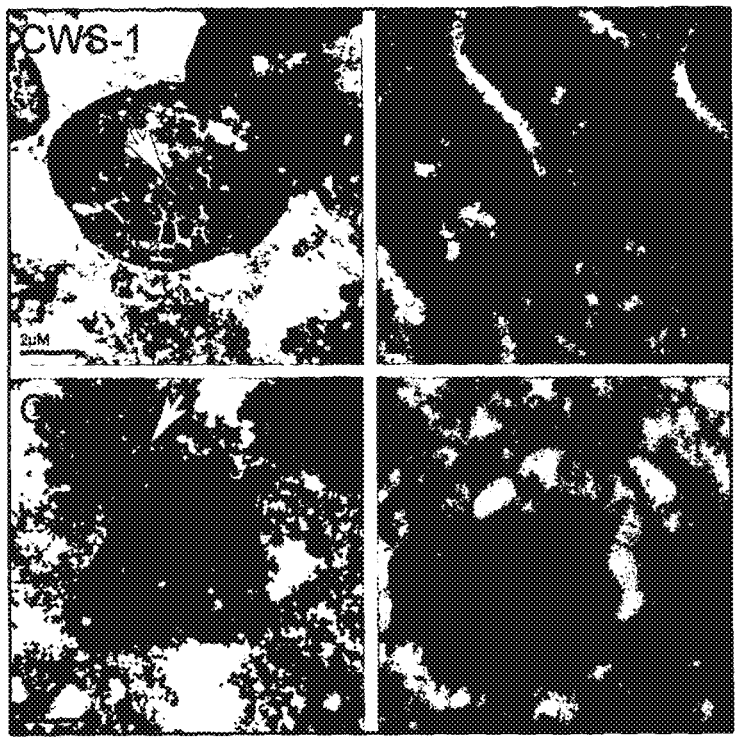

FIG. 10. TCPs are found in human wounds.

Visualization of binding of TCPs to cocci found in fibrin slough from a chronic wound surface (CWS-1 and -2) of two patients with *S. aureus* infected chronic leg ulcers. In the EM experiments, no significant unspecific binding of gold-conjugated IgG was observed. Scale bar; 200 nm.

Figure 11:
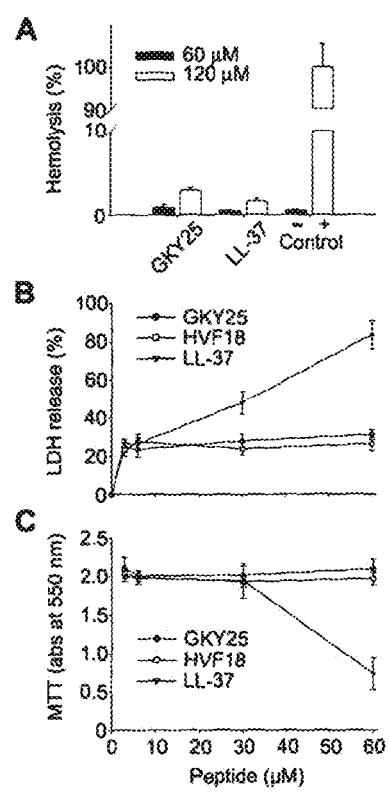

FIG. 11. Effects on eukaryotic cells.

(A) Hemolytic effects of GKY25 in blood (EDTA-blood made 50% with PBS) were investigated. The cells were incubated with different concentrations of the peptide or LL-37.2% Triton X-100 (Sigma-Aldrich) served as positive control. The absorbance of hemoglobin release was measured at λ 540 nm and is expressed as % of Triton X-100 induced hemolysis (note the scale of the y-axis). (B) HaCaT keratinocytes were subjected to GKY25 and LL-37 in presence of 20% human serum. Cell permeabilizing effects were measured by the LDH based TOX-7 kit. LDH release from the cells was monitored at λ 490 nm and was plotted as % of total LDH release. (C) The MTT-assay was used to measure viability of HaCaT keratinocytes in the presence of the indicated peptides. In the assay, MTT is modified into a dye, blue formazan, by enzymes associated with metabolic activity. The absorbance of the dye was measured at λ 550 nm.

Figure 12:
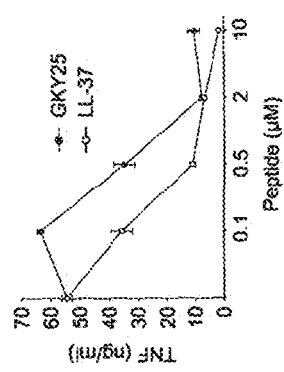

FIG. 12. TNF-α release is inhibited by GKY25.

RAW264.7 macrophages were stimulated with LPS from *E. coli*, in presence of GKY25 at the indicated concentrations. LL-37 is presented for comparison.

Figure 13:
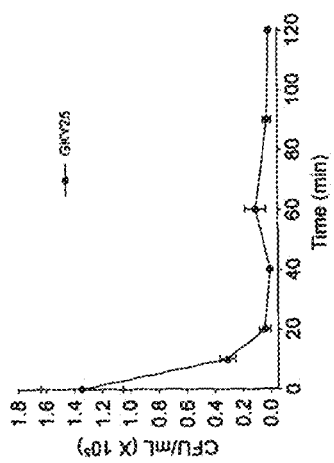

FIG. 13. Kinetics of GKY25 action.

*E. coli* bacteria were grown to mid-logarithmic phase in Todd-Hewitt (TH) medium. They were then washed and diluted in 10 mM Tris, pH 7.4 containing 5 mM glucose. Following this, bacteria (50 μl; $2 \times 10^6$ cfu/ml) were incubated, at 37° C. for for 5, 10, 20, 40, 60 and 120 min with GKY25 at 6 μM in presence of 10 mM Tris, 0.15 M NaCl, pH 7.4. To quantify the bactericidal activity, serial dilutions of the incubation mixtures were plated on TH agar, followed by incubation at 37° C. overnight and the number of colony-forming units was determined. 100% survival was defined as total survival of bacteria in the same buffer and under the same condition in the absence of peptide.

Figure 14:
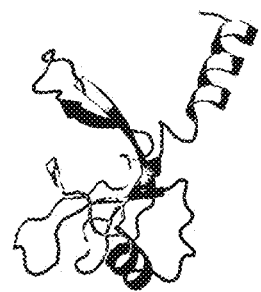

FIG. 14. γ-core motif of TCP.

Cartoon representation of the part corresponding to the C-terminal 96 amino acids of the crystal structure of thrombin (PDB code: 1C5L, amino acids 527-622). The region $C^{536}$KDSTRIRITDNMFCAGYKP$^{555}$ [SEQ ID NO:30] containing the proposed γ-core motif is indicated in red. Cysteines are indicated in yellow and glycines in orange. The motif corrsponds to the levomeric isoform 1 described by Yount and Yeaman (Yount, N.Y. & Yeaman, M.R. Multidimensional signatures in antimicrobial peptides. *Proc Natl Acad Sci USA* 101, 7363-7368(2004)); ($NH_2$ ... [C]-[$X_{13}$]-[CXG]-[$X_2$]-P ... COOH [SEQ ID NO:8]), and is quite similar to the γ-core motif found in kinocidins (Yeaman, M.R & Yount, N.Y. Unifying themes in host defence effector polypeptides. *Nat Rev Microbiol.* 5, 727-740 (2007).

Figure 15:
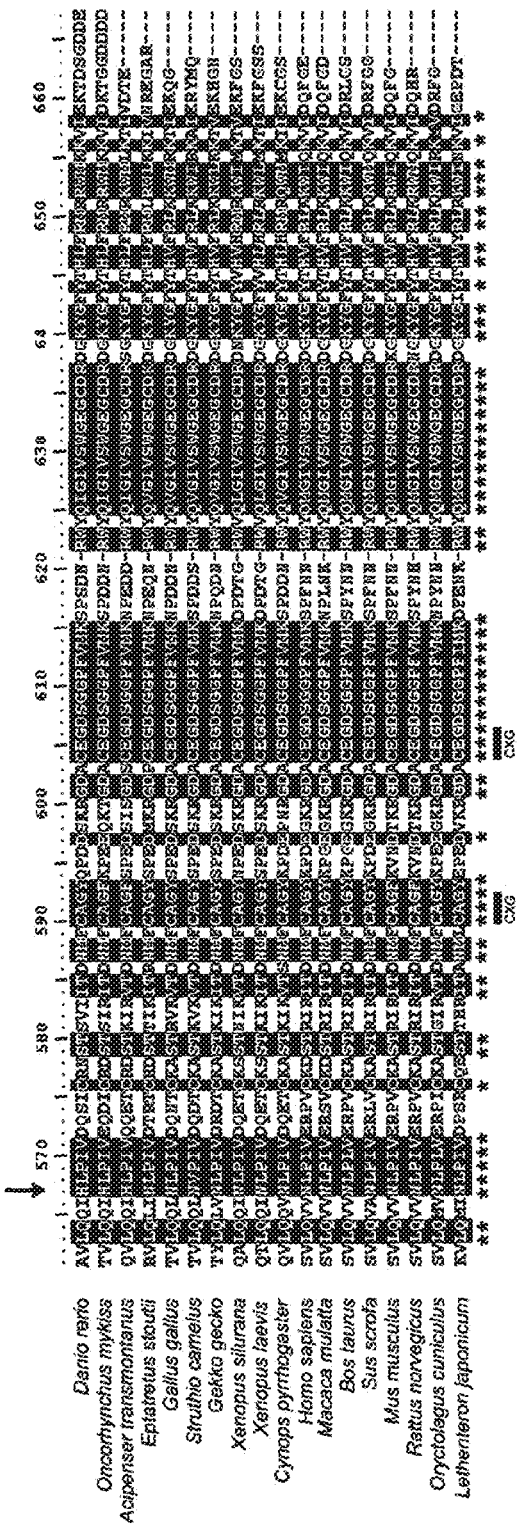

FIG. 15. Alignment of human TCP with related thrombin sequences.

The conserved cysteine residues, as well as two CXG motifs are indicated. Arrow indicates the N-terminus of the 96 amino acid peptide generated by neutrophil elastase [SEQ ID NOS:32-491].

Figure 16:
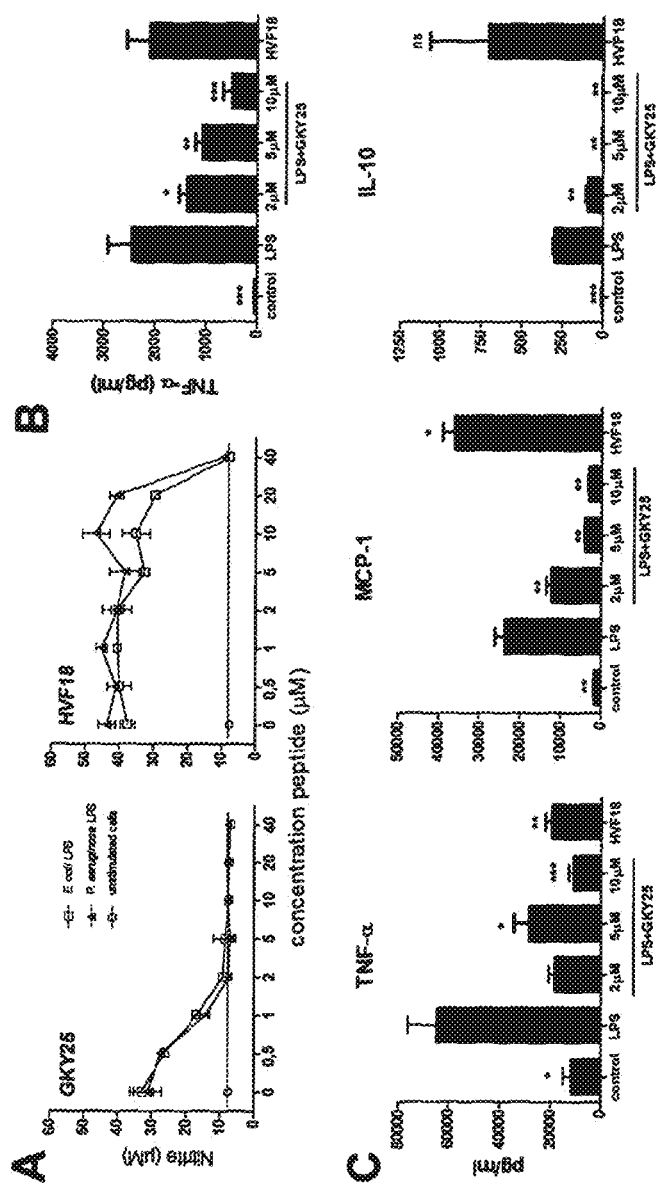

FIG. 16. Thrombin-derived peptides modulate the cytokine response to LPS in vitro (A) GKY25 and HVF18 significantly block nitrite production. RAW 264.7 macrophages were stimulated with 10 ng/ml *E. coli* or *P. aeruginosa* LPS in combination with indicated concentrations of GKY25 and HVF18. (B) GKY25 and HVF18 damped TNF-α production by human peripheral blood monocytes (C) GKY25 and HVF18 significantly modulate the release of proinflammatory cytokines. RAW 264.7 cells were stimulated with 10 ng/ml *E. coli* LPS and cytokines were analysed in the cell supernatants.

Figure 17:
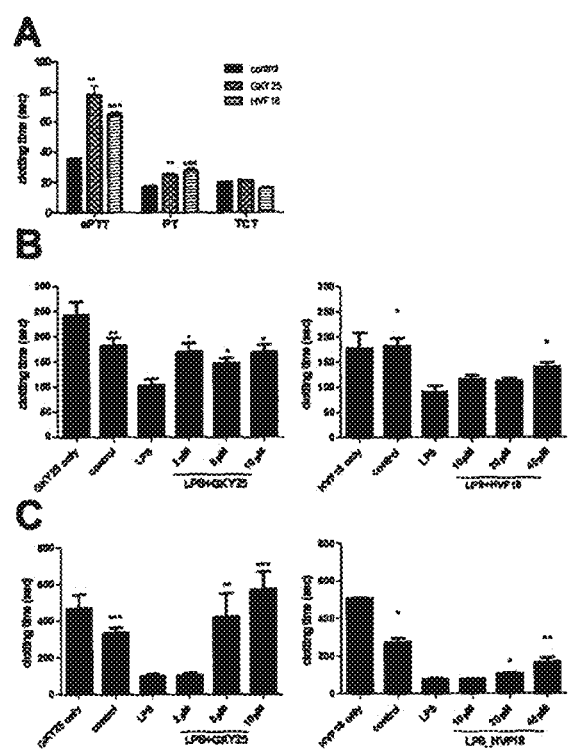

FIG. 17. Thrombin-derived peptides influence the coagulation system in vitro.

(A) GKY25 and HVF18 significantly prolong the activated partial thrombin time (aPTT) and prothrombin time (PT) in vitro. Thrombin clotting time (TCT) times were determined without (control) or with 20 μM of GKY25 or HVF18. (B) GKY25 and HVF18 prolong clotting times in a whole blood assay. Whole blood was incubated with 10 ng/ml E. coli LPS+/−the indicated concentrations of peptide. The clotting reaction in human citrated plasma was initiated by adding the blood cells. (C) GKY25 and HVF18 prevent reduction of clotting times. Human monocytes were stimulated with LPS and/or peptides, and the clotting times were determined by adding the treated cells to human citrate plasma supplemented with $CaCl_2$ FIG. 18. Anti-inflammatory effects of thrombin derived peptides in vivo.

(A-D) Septic shock in C57BL6 mice was induced by intraperitoneal injection of 18 mg/kg E.coli LPS. Thirty minutes later GKY25 and HVF18 (0.5mg; 10 mM Tris, pH 7.4) or buffer only was administered. (A) GKY25 and HVF18 treatment leads to 100% survival in LPS-induced shock compared to control mice (controls; n=12, GKY25; n=10, HVF18; n=10 (p<0.001)). (B) Weight was followed for 7 days. (C) Peptide treatment significantly increases the number of platelets in the LPS-induced shock model. In separate experiments mice were injected with LPS followed by administration of 0.5 mg of GKY25 or HVF18, or buffer. Animals were sacrificed at 8 h, 20 h, or after 7 days and the number of platelets in blood counted using the VetScanSystem. (D) Administration of GKY25 and HVF18 (0.5mg) significantly attenuates the cytokine response compared to control mice. (8 h control; n=12, GKY25; n=8, HVF18; n=11; 20 h control; n=14, GKY25'; n=10, HVF18; n=11). Cytokines were measured in blood from animals sacrificed at 8 or 20 h after LPS injection. (E) GKY25 decreases cytokine levels in P. aeruginosa LPS induced septic shock. C57BL6 were i.p. injected with 36 mg/kg LPS followed by 0.5 mg of GKY25. After 20 h mice were sacrificed and cytokine levels in blood were determined. (control; n=8, GKY25; n=10). All data are representative of two independent experiments [SEQ IDS NOS:2, 50-53, 3, 54-73, 5, 6, 9, 74-83, 7, 84, 29, 85-891].

Figure 19:
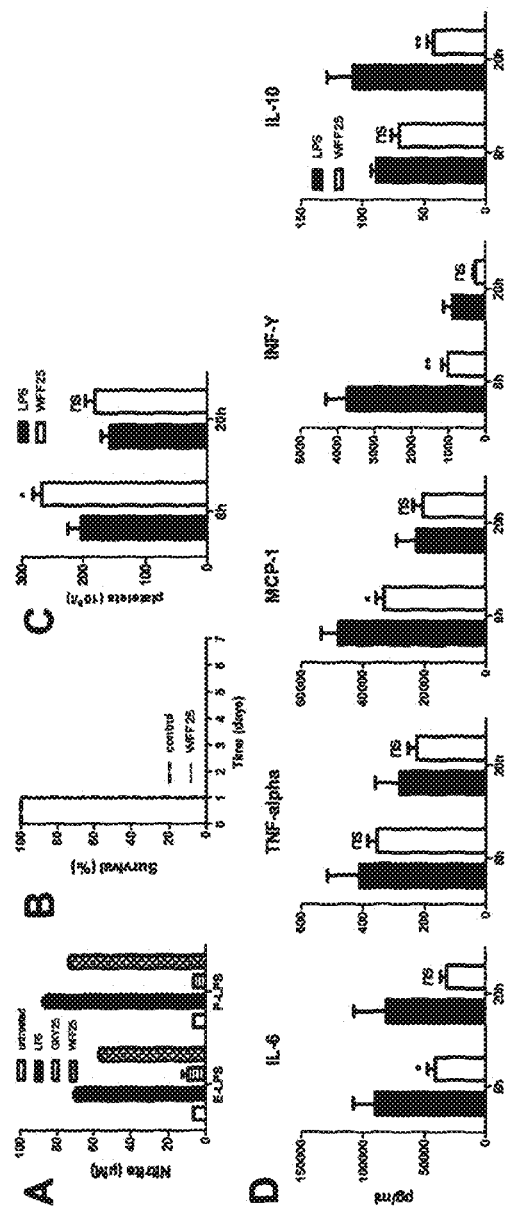

FIG. 19. The scrambled peptide WFF25 does not exert anti-inflammatory effects.

(A) Effects of GKY25 and WFF25 on NO production by macrophages. RAW 264.7 macrophage cells were stimulated with LPS from E. coli or P. aeruginosa (10 ng/ml) followed by treatment with the indicated peptides. NO production in the culture media 24 h after the treatment was determined using the Griess reagent. LPS-stimulated cells without peptide were used as control. (B) WFF25 does not increase survival in LPS-induced shock. Mice were injected with LPS followed by intraperitoneal administration of WFF25 (500 μg). Survival was followed for 7 days. (C) In a separate experiment, mice were sacrificed 20 h after i.p. injection of LPS followed by treatment with WFF25 (500 μg) or buffer, and thrombocytes analyzed in blood. (D) As in (C), but the indicated cytokines were analyzed in blood. (n for controls, n=for treated animals).

Figure 20:
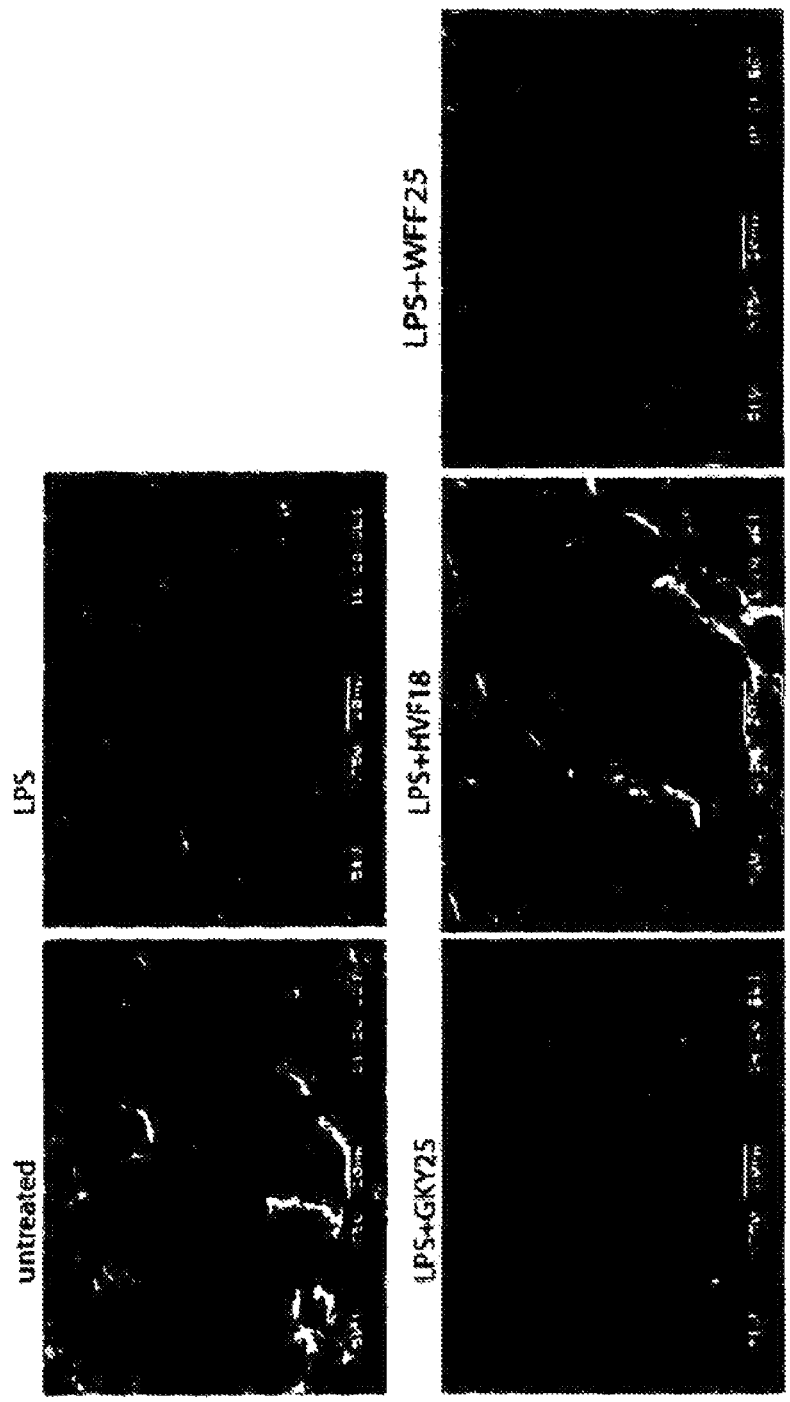

FIG. 20. GKY25 and HVF18 prevent organ damage in a LPS model in vivo.

Lungs were analyzed by scanning electron microscopy 20 h after LPS injection i.p., followed by treatment with the indicated peptides (0.5 mg) or buffer. Treatment with the peptides GKY25 and HVF18, but not with WFF25, blocked leakage of proteins and erythrocytes (n=3 in both groups, and a representative lung section is shown).

Figure 21:
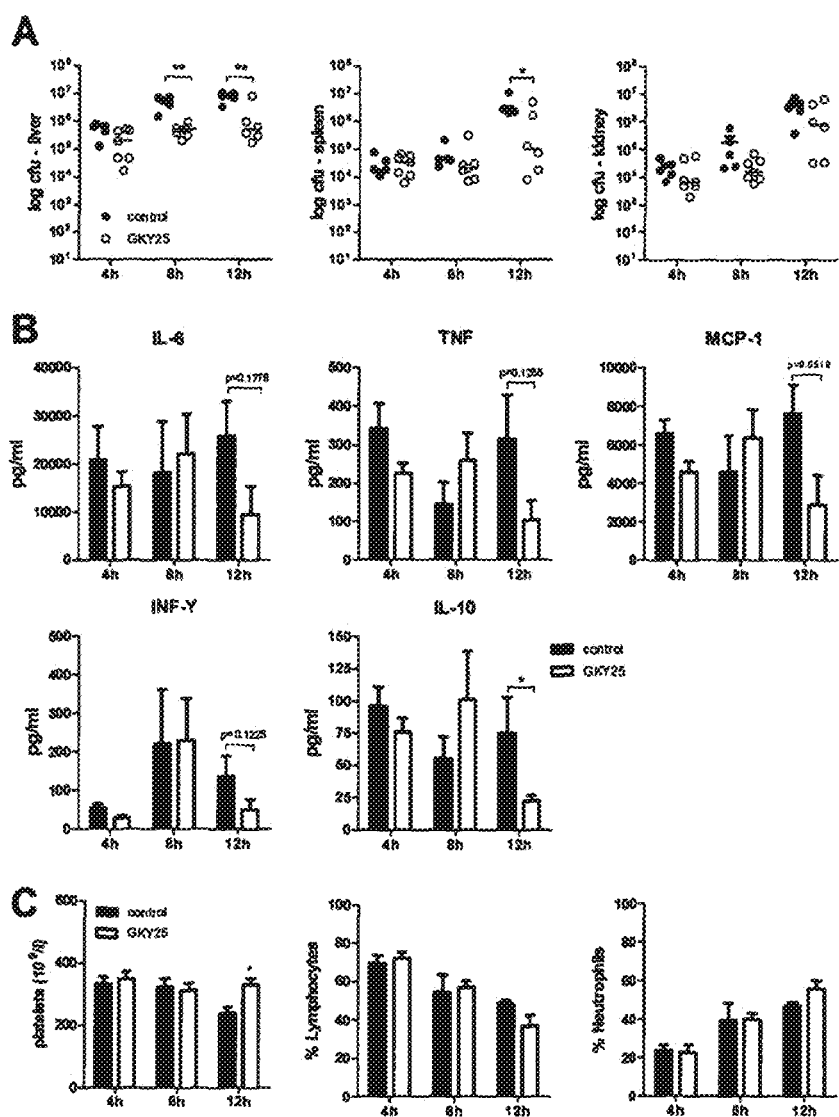

FIG. 21. Kinetics of P. aeruginosa Infection in mice and effects on cytokines.

Mice were inoculated with P. aeruginosa and GKY25 (0.5 mg) was administrated sc 1 h after infection. (A) Bacterial counts in the indicated organs were analyzed after a time period of 4, 8, and 12 h. (B) In parallel, the indicated cytokines were analyzed in blood. (C) Effects on platelets, lymphocytes, and neutrophils are shown.

Figure 22:
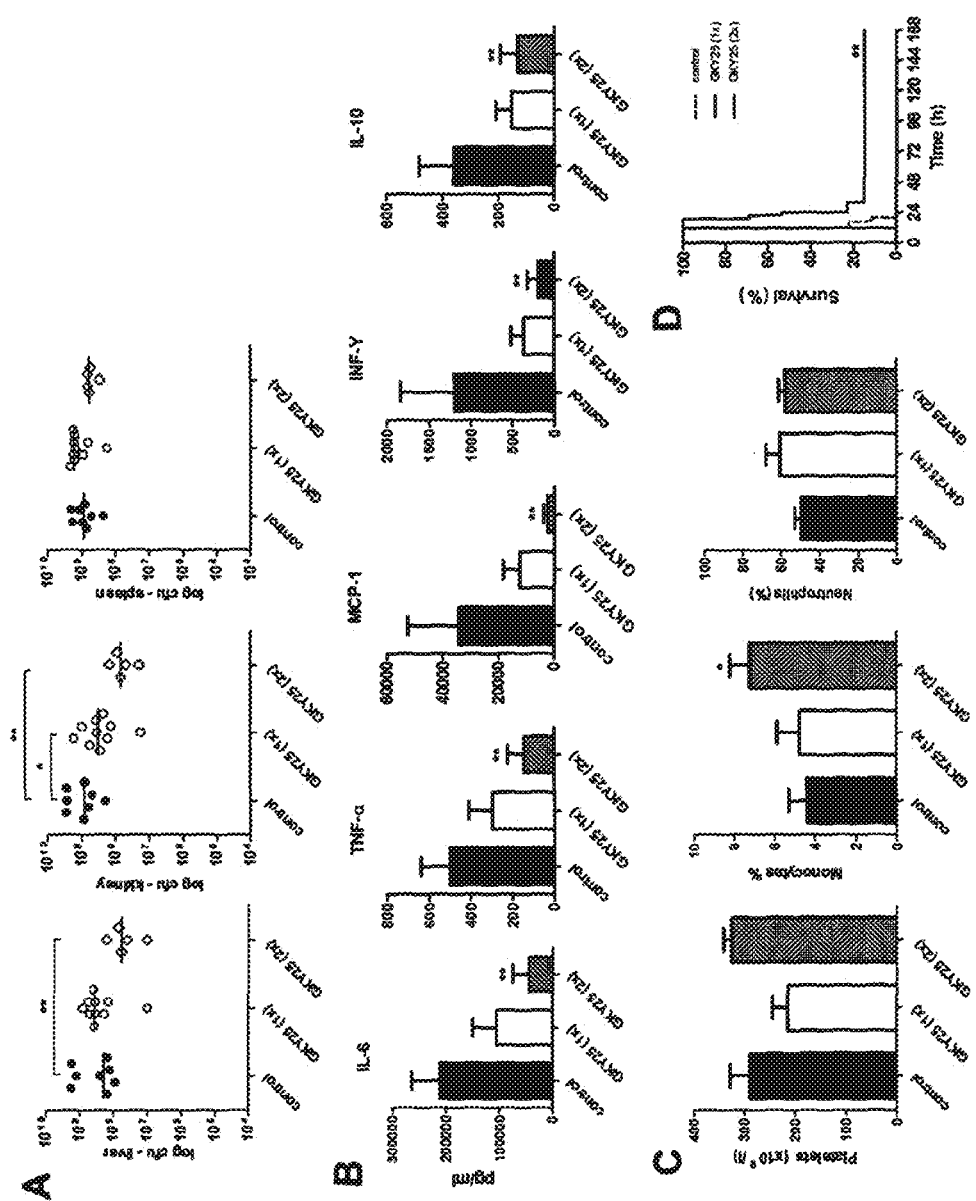
Figure 23:
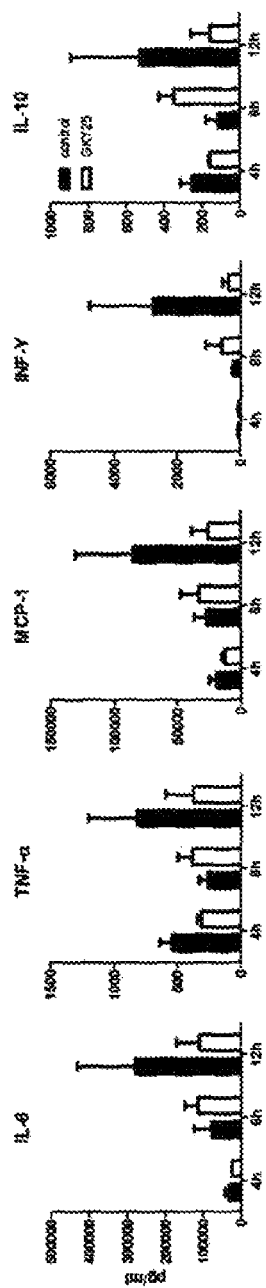

FIG. 22. Therapeutic efficiency of GKY25 in P. aeruginosa sepsis. Mice were inoculated with P. aeruginosa intraperitoneally and GKY25 was administrated sc 1 h, or 1 and 7 h after inoculation with the bacteria. (A) Bacterial counts in the indicated organs were analyzed after a time period of 12 h. (B) In parallel, the indicated cytokines were analyzed in blood. (C) Effects on platelets, lymphocytes, and neutrohils are shown. (D) Mice were inoculated with P. aeruginosa and GKY25 was administrated sc 1 h, or 1 and 7 h after inoculation with the bacteria, and survival of animals was registered. Administration of GKY25 twice (1 and 7 h after infection) significantly enhances survival.

FIG. 23.

Mice were inoculated with P. aeruginosa (at a higher dose than in FIG. 6; $1\times10^8$ cfu/ml) and GKY25 (500 μg) was administrated sc 1 h after infection. The indicated cytokines were analyzed in blood.

Figure 24:
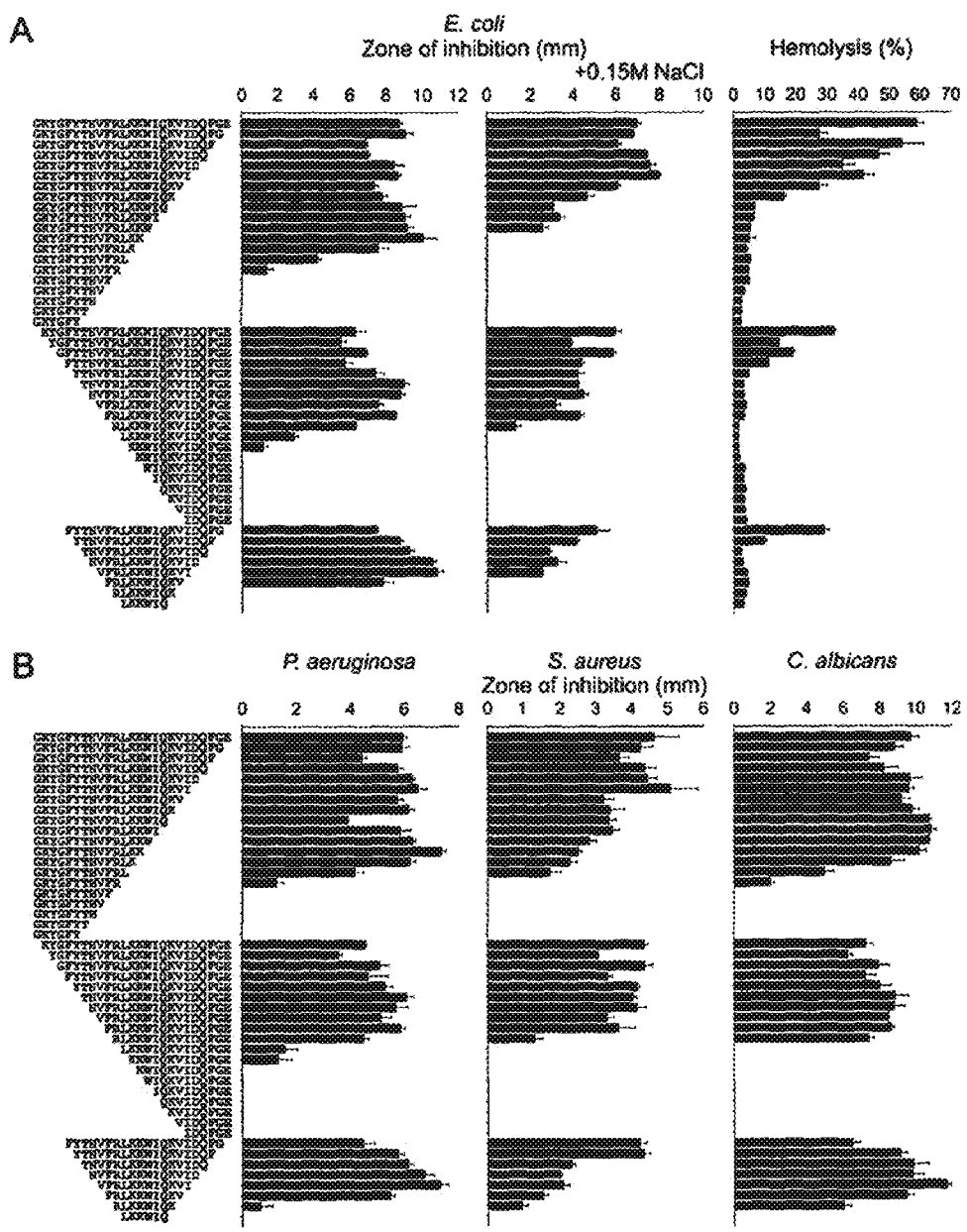

FIG. 24. Antibacterial and hemolytic activities of PEP screen peptides.

(A) Composite figure indicating antimicrobial activity against E. coli and hemolysis (in %). The peptides were tested for antimicrobial activity in low-salt and high-salt conditions. E. coli ATCC 25922 ($4\times10^6$ cfu) was inoculated in 0.1% TSB agarose gel with or without 0.15M NaCl. Each 4 mm-diameter well was loaded with 6 μl of peptide (at 100 μM). The bar diagram indicate the zones of clearance obtained (in mm) correspond to the inhibitory effect of each peptide after incubation at 37° C. for 18-24 h. Hemolytic effects were investigated by incubating the cells with 60 μM of the peptides. 2% Triton X-100 (Sigma-Aldrich) served as positive control. The absorbance of hemoglobin release was measured at λ540 nm and is expressed as % of Triton X-100 induced hemolysis. Error bars represent the standard error of the mean (n=3). (B) Antimicrobial activities of peptides (at 100 μM in RDA) against P. aeruginosa ATCC 27853, S. aureus ATCC 29213, and Candida albicans ATCC 90028 [SEQ IDS NOS: 2, 50-53, 3, 54-73, 5, 6, 9, 74, 83, 7, 84, 29, and 85-891].

Figure 25:
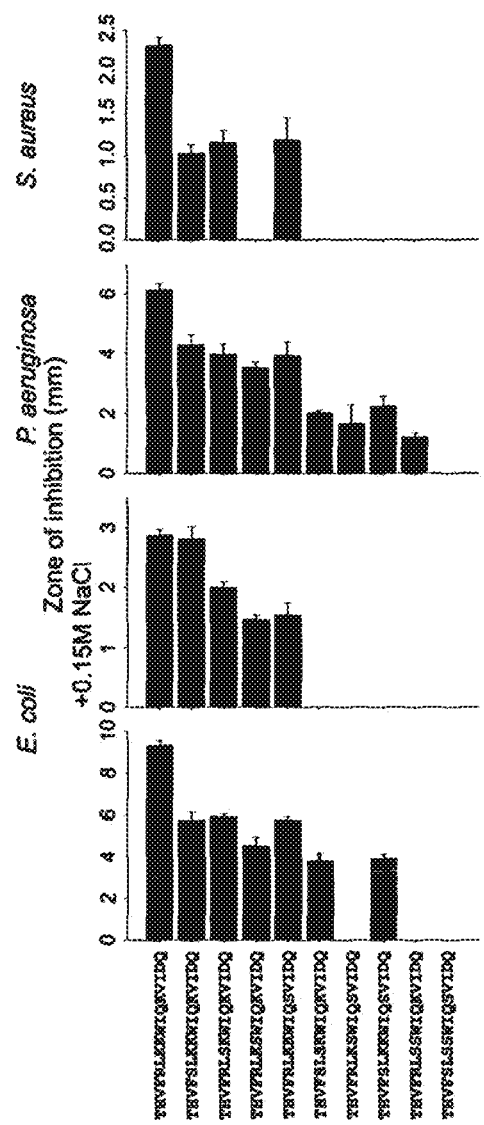

FIG. 25. Activities of K-S variant peptides.

Antimicrobial activity (in RDA) of peptides having lysine replaced by serine against E. coli ATCC25922, P. aeruginosa ATCC 27853, and S. aureus ATCC 29213 are shown. Bacteria ($4\times10^6$ cfu) were inoculated in 0.1% TSB agarose gel. Each 4 mm-diameter well was loaded with 6 μl of peptide (at 100 μM). The bar diagram indicate the zones of clearance obtained (in mm) correspond to the inhibitory effect of each peptide after incubation at 37° C. for 18-24 h [SEQ IDS NOS:29, and 90-981].

Figure 26:
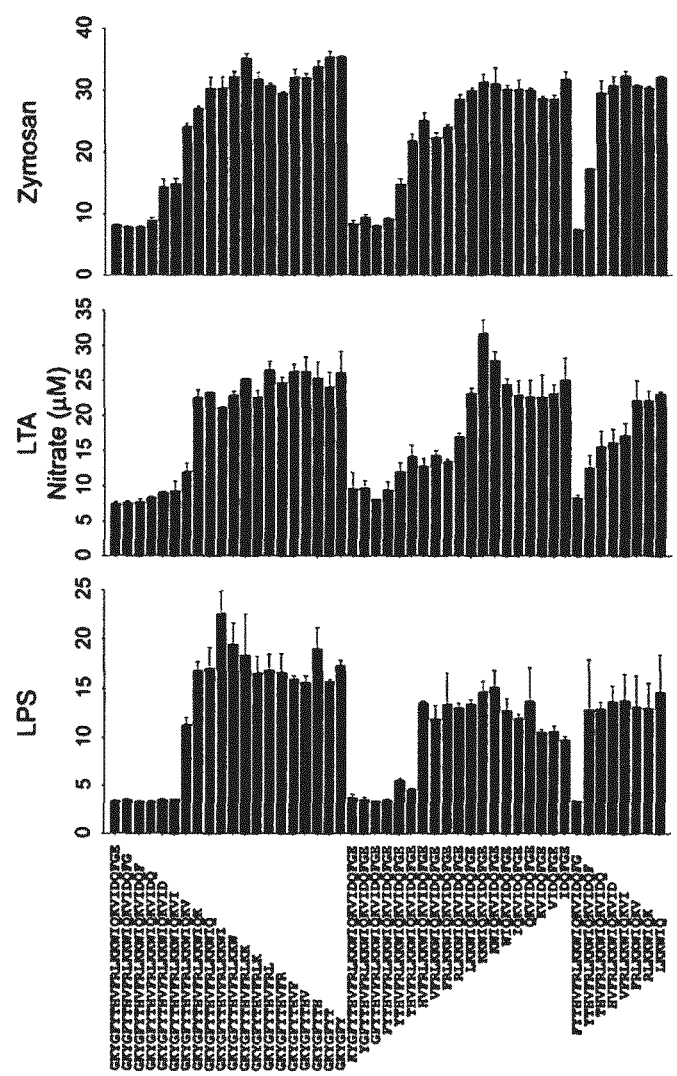

FIG. 26. Immunomodulatory activities in vitro.

Effects on NO production. (A) RAW 264.7 macrophage cells were stimulated with LPS from E. coli (10 ng/ml), LTA from S. aureus (10 μg/ml), and zymosan A from Saccharomyces cerevisiae (25 μg/ml), followed by treatment with 10 μM of peptide. NO production in the culture media 24 h after the treatment was determined using the Griess reagent.

Figure 27:
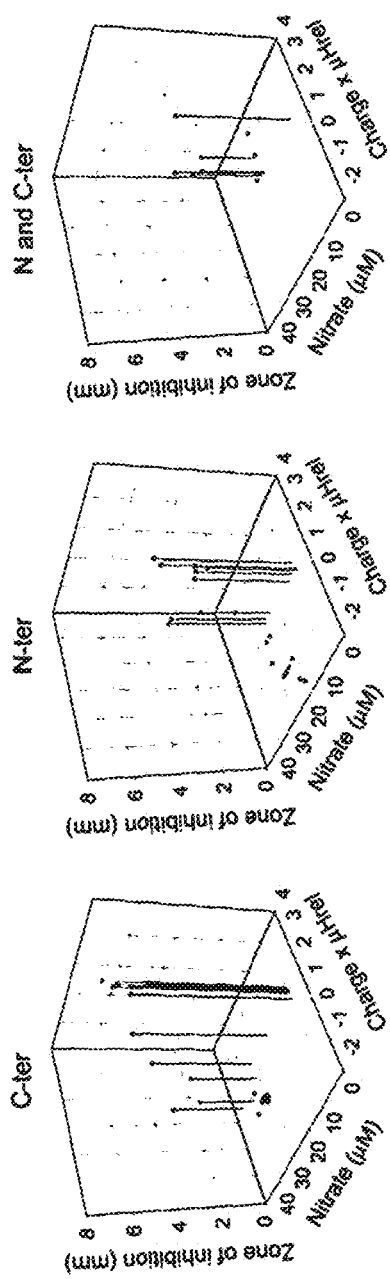

FIG. 27. Correlation of the biological activity, net charge and relative hydrophobic moment.

The antimicrobial and immunomodulatory activities vs. net charge and relative hydrophobic moment (μHrel) of the truncated GKY25 variants (C-, N-, or combined C and N-terminal truncations), are indicated in the 3-D graph. Effects of peptides (at 100 μM in 0.15 M NaCl) against E. coli ATCC 25922 in RDA are indicated.

Figure 28:
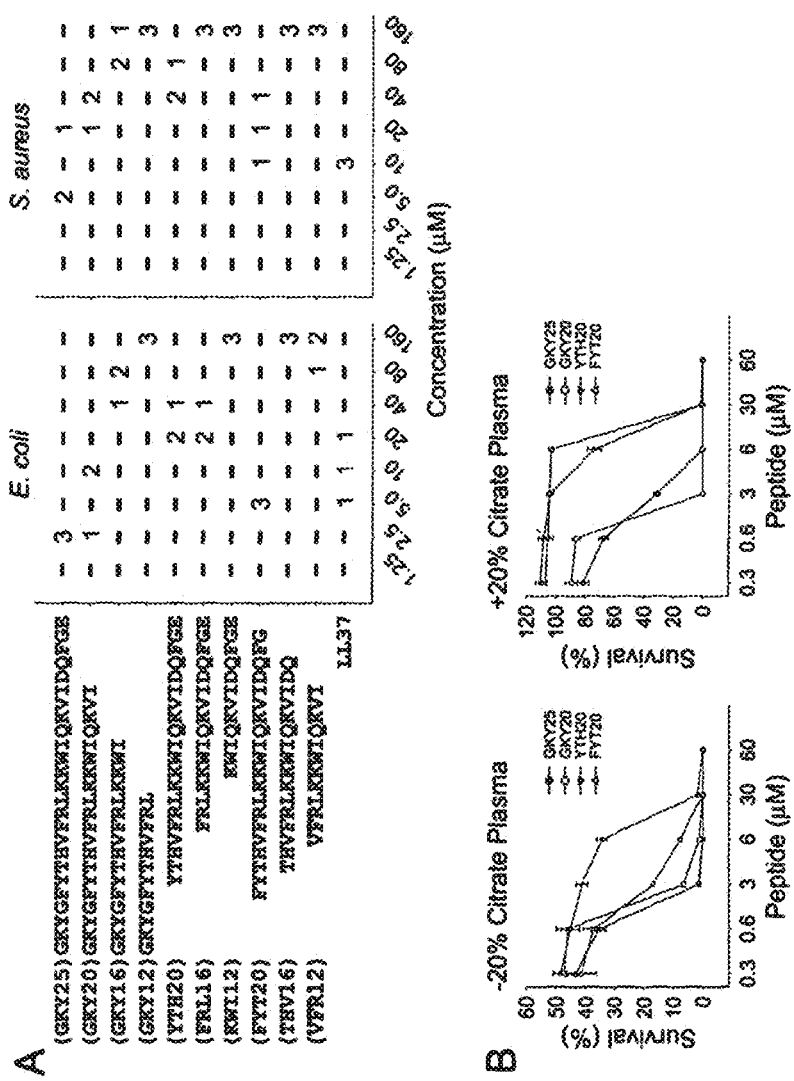

FIG. 28. Antimicrobial activities of selected peptides at physiological conditions.

(A) Minimal inhibitory concentrations (MIC) of peptides for different strains of *E. coli, S. aureus* and *P. aeruginosa* are indicated. (B) Antibacterial effects of the indicated peptides against *E. coli* ATCC 25922 in viable count assay are presented. $2 \times 10^6$ cfu/ml of bacteria were incubated in 50 µl with the indicated peptides at 0.3-60 µM in 10 mM Tris, pH 7.4, 0.15 M NaCl (left panel) or the same buffer containing 20% human plasma (right panel). Identical buffers without peptides were used as controls [SEQ IDS NOS:2, 3, 57, 61, 72, 9, 74, 7, 29, and 861].

Figure 29:
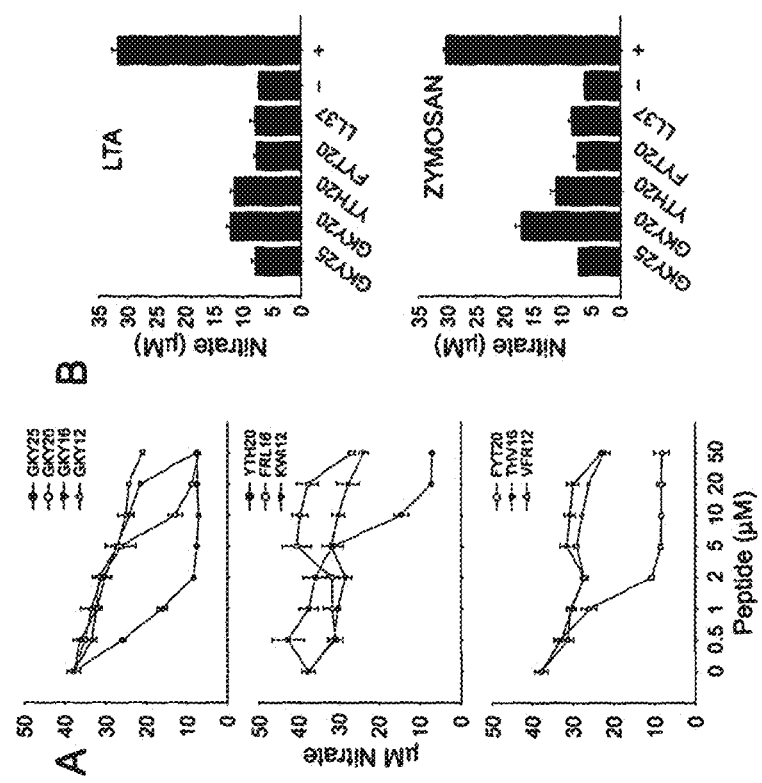

FIG. 29. Immunomodulatory activities of selected peptides.

(A) Dose dependent inhibitory effects on NO production by RAW 264.7 macrophage cells stimulated by LPS are evaluated. Cells were stimulated with LPS from *E. coli* (10 ng/ml), followed by treatment with the indicated peptides at 0.5-50 µM. NO production in the culture media 24 h after the treatment was determined using the Griess reagent. LPS-stimulated cells without peptide were used as control. (B) Peptide effects on NO production of macrophages subjected to LTA or zymosan. LTA from *S. aureus* (10 µg/ml), and zymosan A from *Saccharomyces cerevisiae* (25 µg/ml) at 10 µM was used. GKY25 and LL37 are presented for comparison. Unstimulated and stimulated cells served as negative and positive controls, respectively.

Figure 30:
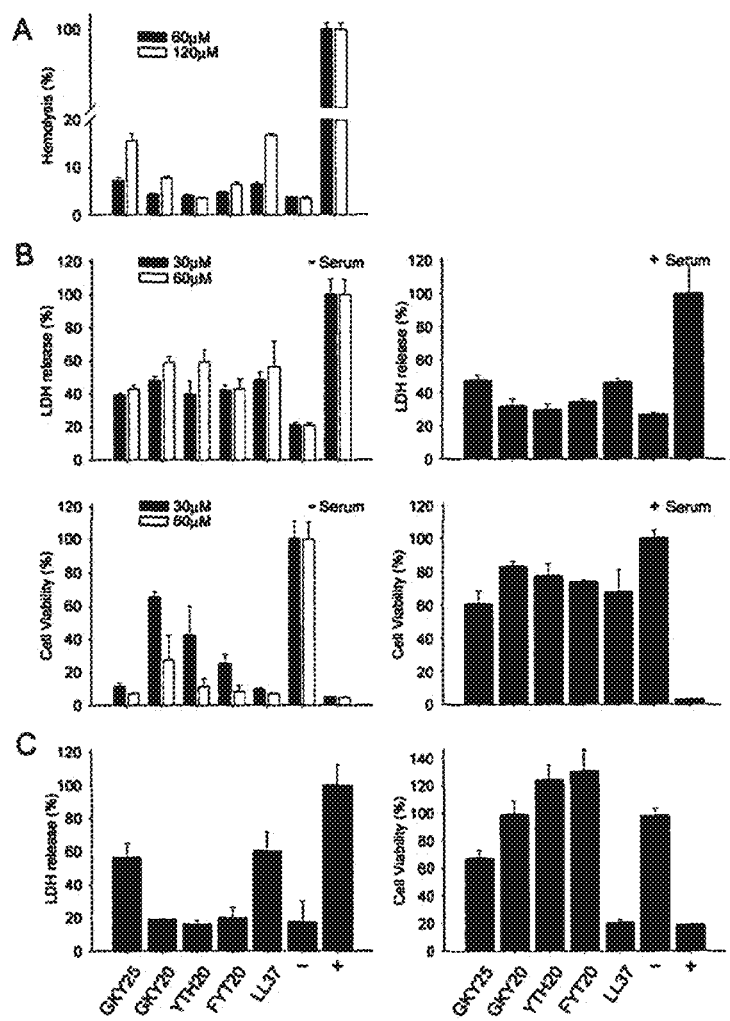

FIG. 30. Activities of peptides against eukaryotic cells.

(A) Hemolytic effects of the indicated variant peptides were investigated, and corresponding data for LL-37 are included for comparison. The cells were incubated with the peptides at 60 µM and 120 µM, 2% Triton X-100 served as positive control. The absorbance of hemoglobin release was measured at 540 nm and is expressed as % of Triton X-100 induced hemolysis (note scale of y-axis). (B) Effects of peptides on HaCaT cells in absence (left panel) and presence of human serum (right panel). The MTT-assay (upper panel) was used to measure viability of HaCaT keratinocytes at 30 µM and 60 µM in absence of human serum, and at 60 µM in the presence of. In the assay, MTT is modified into a dye, blue formazan, by enzymes associated with metabolic activity. The absorbance of the dye was measured at 550 nm. Cell permeabilizing effects of the indicated peptides (lower panels) were measured by the LDH based TOX-7 kit. LDH release from the cells was measured at 490 nm and was plotted as % of total LDH release. (C) Effects of peptides on human skin fibroblasts. The MTT-assay (left panel) was used to measure viability of fibroblasts in the presence of the indicated peptides at 60 µM in absence of human serum. Cell permeabilizing effects of the indicated peptides (right panel) were measured by the LDH based TOX-7 kit as above.

Figure 31:
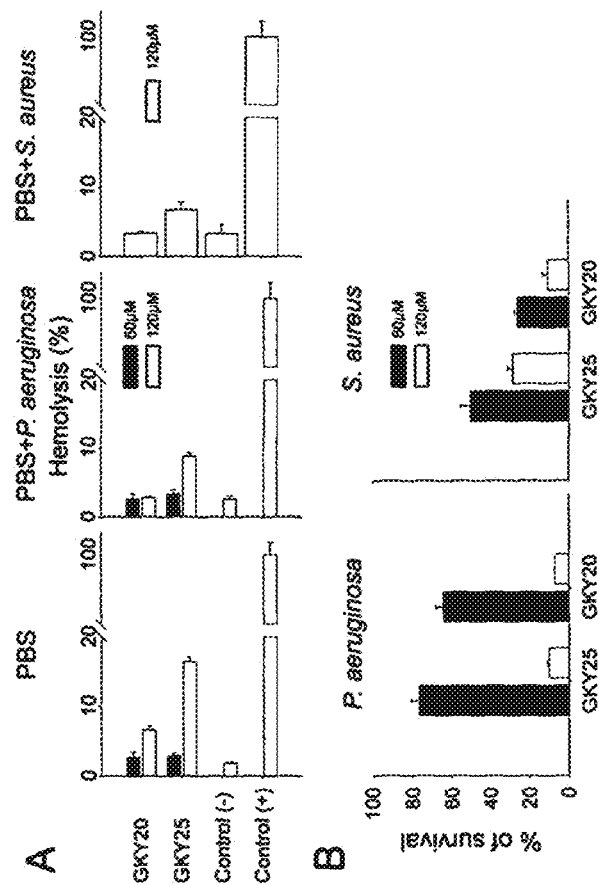

FIG. 31. Activities of GKY25 and GKY20 in human blood infected by bacteria.

(A) Hemolysis in human blood (made 50% in PBS) in presence of the indicated bacteria as well as peptides. Hemolysis was assessed after 1 hour. (B) In an identical setup, antibacterial effects of the indicated peptides were studied. *S. aureus* and *P. aeruginosa* ($2 \times 10^8$ cfu/ml) were added to 50% citrate blood, followed by addition of peptide at 60 or 120 □M. The number of cfu was determined after an incubation period of 1 hour.

Figure 32:
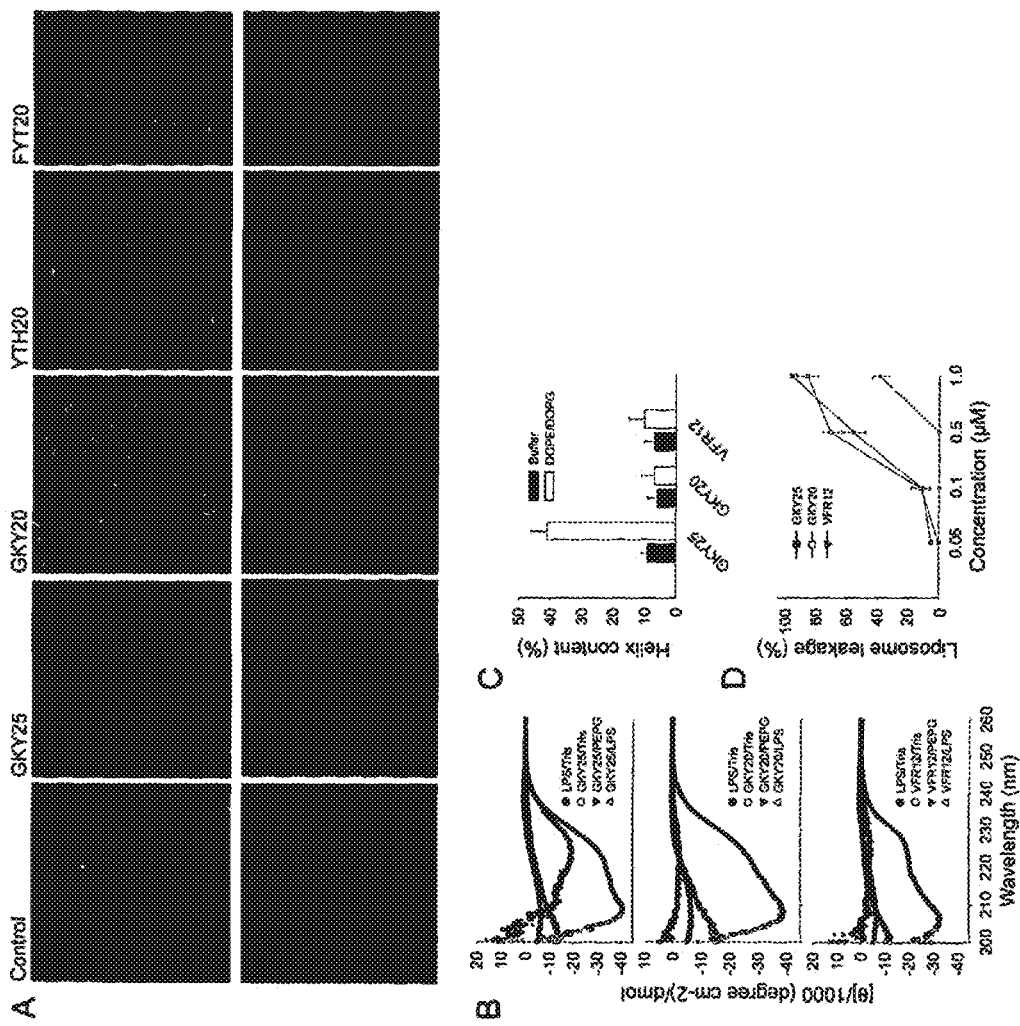

FIG. 32. Permeabilization effects and structure of peptides (A) Permeabilizing effects of peptides on *E. coli*. Bacteria were incubated with the indicated peptides and permeabilization was assessed using the impermeant probe FITC. (B) CD spectra of the indicated peptides in Tris-buffer and in presence of LPS or anionic liposomes. (C) Helical content of GKY25, GKY20, or VFR12 in presence of negatively charged liposomes (DOPE/DOPG). (D) Effects of the indicated peptides on liposome leakage. The membrane permeabilizing effect was recorded by measuring fluorescence release of carboxyfluorescein from PA (negatively charged) liposomes. The experiments were performed in 10 mM Tris-buffer. Values represents mean of triplicate samples.

Figure 33:
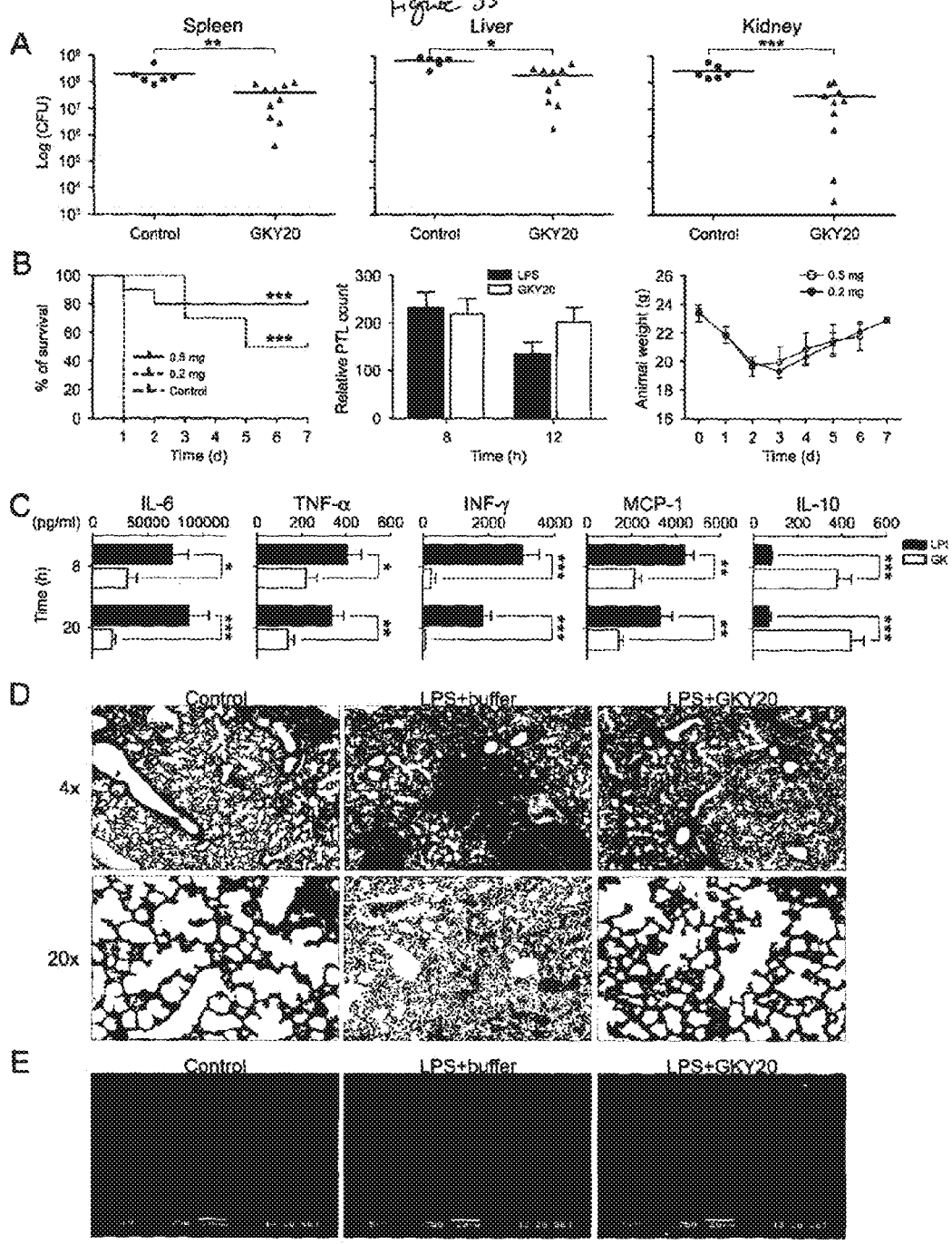

FIG. 33. In vivo effects of GKY20.

(A) GKY20 suppresses bacterial dissemination to the spleen, liver and kidney. Mice were injected i.p. with *P. aeruginosa* bacteria, followed by i.p. injection of GKY20 or buffer only, and the cfu of *P. aeruginosa* in spleen and kidney was determined after a time period of 12 h (n=6 for controls and n=10 for treated (spleen; P<0.002, liver; P<0.011; and kidney; P<0.001). Horizontal line indicates median value). (B) GKY20 significantly increases survival in LPS-induced shock. Mice were injected intraperitoneally with LPS followed by intraperitoneal administration of GKY25 (200 OR 500 µg). Survival was followed for 7 days. (n=12 for controls, n=10 for treated animals, P<0.001) (left panel). Platelet counts (middle panel) and weight of the animals (right panel) is also indicated. (C) GKY20 reduces release of pro-inflammatory cytokines. In a separate experiment, mice were sacrificed 20 h after i.p. injection of LPS followed by treatment with GKY20 (500 µg) or buffer, and the indicated cytokines were analyzed in blood (n=9 for controls, n=8 for treated animals, the P values for the respective cytokines are IL-6; 0.001, TNF-α; 0.006, IFN-γ; 0.001, MCP-1; 0.008. IL-10 was increased (P=0.001). (D) Lungs were analyzed 20 h after LPS injection i.p. followed by treatment with GKY20 (500 µg) or buffer. Histochemical analysis shows marked attenuation of inflammatory changes in GKY20-treated lungs (a representative lung section is shown). (E) Lungs were analyzed by scanning electron microscopy 20 h after LPS injection i.p., followed by treatment with GKY20 (500 µg) or buffer. Treatment with the peptide blocked leakage of proteins and erythrocytes (n=3 in both groups, and a representative lung section is shown).

EXAMPLES

Example A

Proteolysis of Human Thrombin Generates Novel Host Defense Peptides

Summary

Wounding of the skin, as well as other epithelial barriers, represents an ever present challenge, posing a potential threat for invasive infection and sepsis. Therefore, it is not surprising that evolutionary pressure has maintained, and developed multiple host defense systems involving initial hemostasis and fibrin formation, and the subsequent action of multiple proteins and peptides of our innate immune system. In humans, the coagulation pathways and those mediating innate immune responses to infections have so far been seen as separate entities. This view is challenged by the present study, disclosing novel host defense functions of C-terminal peptides of thrombin, a key enzyme in the coagulation cascade. The thrombin-derived peptides, which are detected in human wounds and fibrin, effectively kill microbes by membrane lysis, but also exert potent immunomodulatory and anti-endotoxic functions. Importantly, in animal models, they are protective against *P. aeruginosa* sepsis, as well as lipopolysaccharide-induced shock. Thus, from the perspective of wounding and infection, thrombin, after fulfilling its primary function in generating a first line of defense, the fibrin clot, serves an additional role by the generation of antimicrobial and anti-endotoxic host-defense peptides.

Introduction

The innate immune system, largely based on antimicrobial peptides, provides a first line of defense against invading microbes [1,2,3,4,5]. During recent years it has become increasingly evident that many cationic and amphipathic antimicrobial peptides, such as defensins and cathelicidins, are multifunctional, also mediating immunomodulatory roles and angiogenesis [6,7,8], thus motivating the recent and broader definition host defense peptides (HDP) for these members of the innate immune system. The family of HDPs has recently been shown to encompass various bioactive peptides with antimicrobial activities, including proinflammatory and chemotactic chemokines [9], neuropeptides [10], peptide hormones [11,12], growth factors [1,3], the anaphylatoxin peptide C3a [14,15], and kininogen-derived peptides [16,17,18].

The coagulation cascade represents a fundamental host defense system activated in response to injury and infection [19,20]. Through a series of cascade-like proteinase activation steps, thrombin is formed, leading to fibrinogen degradation and clot formation [20]. In addition, thrombin has other physiologic functions in hemostasis; i.e., mediating clot stabilization by activation of TAFI and activation of transglutaminase (FXIII), providing anticoagulant and antifibrinolytic activities in complex with thrombomodulin, and causing platelet aggregation due to PAR cleavage [19,20]. Moreover, thrombin elicits numerous cellular responses, including increased CAM expression and growth factor and cytokine release by endothelial cells, as well as growth stimulation of both to smooth muscle and fibroblast cells [20]. These pivotal functions of thrombin in host defense, its ubiquitous occurrence in blood and in fibrin networks, the high evolutionary conservation of the enzyme, as well as presence of an amphipathic, cationic and helical C-terminus in the protein [19], made us raise the question whether thrombin could constitute a source of HDPs released at sites of wounding and infection. Our results indeed show that C-terminal peptides of thrombin constitute a previously undisclosed and significant class of HDPs, generated in humans during wounding and with therapeutic potential against infection and septic shock.

Results

Proteolysis of Prothrombin and Thrombin Generates Antimicrobial Activity

To test the hypothesis that prothrombin or its activated forms may generate antimicrobial peptides upon fragmentation, we incubated human prothrombin and thrombin with neutrophil elastase, a major neutral protease released by leukocytes during blood coagulation and inflammation or in response to bacterial products such as endotoxins. Earlier studies have shown that neutrophil elastase acts on proteinase-sensitive regions in human thrombin, generating smaller fragments [21]. As judged by the RDA assays (FIG. 1A), digestion of the proteins yielded antimicrobial activity already after 5 min of incubation with the enzyme. In contrast, the intact mother proteins were inactive. The activity following proteolysis was still observed after several hours of incubation, suggesting the presence of relatively stable intermediates. Noteworthy, the maximum observed inhibition zones were similar in size to those generated by the classical antimicrobial peptide LL-37. Analysis by SDS-PAGE (FIG. 1B) showed that the degradation generated several low molecular weight fragments in the range of 5-15 kDa. In spite of the known amidolytic properties of thrombin, no detectable antimicrobial activity was detected after prolonged incubation of the enzyme form alone (not shown).

The observation that the zymogen as well as the activated forms generated similar activities, suggests that the antimicrobial epitopes localize to regions in the active enzyme after R271 (prothrombin numbering).

Structure-based Screening for Identification of Antimicrobial Epitopes

In order to identify possible antibacterial peptide regions of prothrombin/thrombin, overlapping peptide sequences comprising 20 mers (FIG. 2A) were synthesized and screened for antibacterial activities against the two test bacteria *E. coli* and *P. aeruginosa*. Properties common for most antimicrobial peptides include minimum levels of cationicity, amphipathicity, and hydrophobicity [5]. Taking these structural prerequisites into account, additional peptides comprising regions of high net charge and/or presence of amphipathic helical regions, such as those encompassing the C-terminus, were selected and synthesized (FIG. 2A). The experiments showed that particularly peptides derived from the C-terminal region (peptides 45-48) were antimicrobial, although other active peptides were also identified (eg. 9 and 31) (FIG. 2B). However, at high ionic strength (0.1 M NaCl), only the C-terminal peptides retained their antimicrobial activity against *E. coli* as well as *P. aeruginosa* (FIG. 7) demonstrating that only this region, characterized by a high relative hydrophobicity ($\mu$Hrel), positive net charge ($z_{net}$=+2 for the most active C-terminal peptides) (FIG. 2B) and amphipathicity (FIG. 2C), features typical of classical antimicrobial peptides [1,2,3,4], may generate peptides active against bacteria at physiologic conditions. Corresponding to the antimicrobial activities observed above, only peptides derived from the C-terminal part significantly bound to *E. coli* LPS (FIG. 2D).

Figure 1:
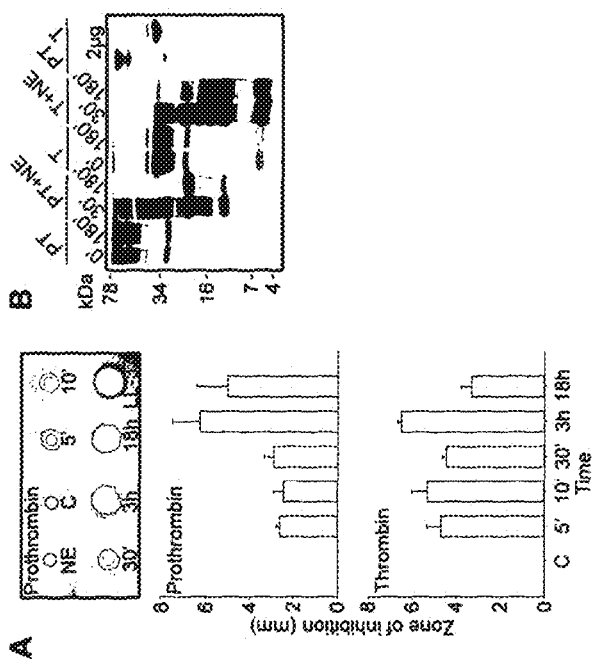
FIG. 1. Generation of antimicrobial peptides by degradation of prothrombin and thrombin.

Since the absence of activity of the holoproteins in RDA could possibly be attributed to their high molecular weight (compromising diffusion during the assay), the antibacterial results above were further substantiated by matrix-free viable count assays. The results demonstrated that in contrast to the holoproteins, the selected model peptides VFR17 (FIG. 2A; peptide 48) and the longer 25mer peptide GKY25 (indicated in FIG. 2A) from the C-terminal part of the enzyme (both peptides indicated by colors in the 3D model of thrombin; FIG. 2E), demonstrated significant antibacterial activity (FIG. 2F), thus corroborating the RDA assays above (FIG. 1A and FIG. 2B). In conclusion, LPS-binding and antimicrobial data, combined with structural and biophysical considerations clearly indicate a pivotal role of Thrombin-derived C-terminal Peptides, in the following text denoted "TCP", for mediating the antimicrobial activity.

Definition of Low Molecular Weight Fragments Generated by Degradation of Thrombin In parallel to the above structure-based screening approach, studies were undertaken to identify active fragments generated after subjection of thrombin to neutrophil elastase. RP-HPLC separation of elastase-digested thrombin, followed by antibacterial assays using *E. coli* identified several antibacterial peptide fractions (FIG. 3A). Combined analyses using MALDI-TOF, ESI-MS/MS, and N- and C-terminal sequencing of fraction no. 38, which contained the majority of the activity comprising peptides active in high salt, unambiguously identified a major 11041 Da fragment comprising the C-terminal 96 amino acids of thrombin (amino acid 527-622, predicted pI 8.4, indicated in FIG. 2A). Correspondingly, SDS-PAGE identified one single peptide of ~11 kDa, that contained the C-terminal epitope, as shown by immunoblot analysis using polyclonal antibodies against the C-terminal peptide VFR17 (FIG. 3A, rightmost upper panel).

Gel overlay assays demonstrated that the major antimicrobial peptide of fraction 38 corresponded to one major active peptide, also identified in neutrophil elastase-digested thrombin (FIG. 3A, rightmost lower panel), showing significantly lower mobility when compared to the C-terminal peptide GKY25, thus reflecting its higher molecular mass. Interestingly, MALDI-TOF and ESI-MS/MS of fraction no. 30 identified the peptide HVFRLKKWIQKVIDQFGE [SEQ ID NO:5], described in the previous in vitro screening experiments (FIGS. 2A and B, peptide 47), as well as a shorter 16 aa long variant (FIG. 3A, FRLKKWIQKVIDQFGE [SEQ ID NO:9]), both peptides from the C-terminus of thrombin. The analyses of the less hydrophobic material (fractions 20 and 21) yielded several low molecular weight fragments corresponding to internal, and cationic, sequences of low hydrophobicity and amphipathicity, matching antibacterial regions identified by the previous 20-mer screening (Table S1 and FIG. 2A). Taken together, these results showed that neutrophil elastase generates antimicrobial TCPs, of which the major forms comprise a ~11 kDa fragment of 96 amino acids, but also smaller fragments from the distal helical and amphipathic terminus.

Thrombin-derived C-Terminal Fragments are Generated by Human and Bacterial Proteinases During inflammation, neutrophils release a multitude of enzymes, which could have activity on either thrombin or its proform. Therefore, thrombin was incubated with supernatants from activated neutrophils and the material analysed for antimicrobial activity and generation of TCPs. Indeed, antimicrobial activity was found upon proteolysis, while immunoblotting identified several TCPs of similar molecular weights as those generated by neutrophil elastase alone (FIG. 3B). Similar fragments (FIG. 3C) and corresponding antimicrobial activity (FIG. 3D) were also detected when prothrombin was subjected to neutrophil elastase, cathepsin G as well as the bacterial thermolysin-like proteinase of *Pseudomonas aeruginosa*, lasB (also denoted *P. aeruginosa* elastase) [22]. Interestingly, low molecular weight peptides (~3-4 kDa), generated by the latter *P. aeruginosa* enzyme, co-migrated with the model peptide GKY25 (FIG. 3C). These results demonstrated that both human and bacterial enzymes may generate TCPs, irrespective of the activation state of prothrombin.

C-terminal Thrombin Peptides are Generated Ex vivo and In vivo and are Protective Against Infection Prothrombin, as many other proteins in plasma, is under meticulous control by antiproteinases in the normal state, preventing its activation and/or degradation. Therefore, we hypothesized that favorable environments promoting TCP formation should comprise i) localisation as well as concentration of thrombin, and ii) local release of enzymes, such as neutrophil elastase or bacterial proteinases. These environments are typical of sites of injury and infection, such as skin wounds, comprising thrombin activation, fibrin formation, bacterial colonisation or infection, and subsequent neutrophil influx. Earlier studies have shown that thrombin binds to fibrin clots, and that fibrin acts as a reservoir for active thrombin [23]. Furthermore, human neutrophils release elastase during clotting, and neutrophils also penetrate fibrin [21]. Bacteria, such as *S. aureus* and *P. aeruginosa* frequently colonize and infect skin wounds, accompanied by excessive proteolysis and activation of neutrophils [24,25]. Given this, the production of TCPs in fibrin, as well as in sterile or infected biological fluids and wounds was investigated. The results showed that TCPs were formed when fibrin clots were subjected to neutrophil elastase in vitro (FIG. 4A). Furthermore, a similar ~11 kDa fragment was detected in fibrin "slough" from a patient with a non-infected chronic venous leg ulcer, indicating that TCPs can be found in fibrin in vivo (FIG. 4A). Analogous results, showing rapid formation of TCPs, were obtained using human plasma subjected to proteolysis by neutrophil elastase, thus simulating the high elastase activity observed during wounding (FIG. 4B). Importantly, TCPs were also identified in wound fluid from patients post-surgery, as well as in wound fluid from patients with chronic (non-infected) venous leg ulcers (FIG. 4B). The latter wounds are always colonized by bacteria such as *S. aureus* and *P. aeruginosa* [24].

Next, a series of experiments were performed in order to study the physiological role of TCPs in relation to bacterial infection. First, initial experiments showed that immunoreactive thrombin fragments, including the ~11 kDa TCP peptide, are proteolytically generated and exclusively bind to bacteria during *P. aeruginosa* infection of plasma and in presence of fibrin (FIG. 8). FACS analysis utilizing antibodies against the C-terminal part of thrombin showed that TCPs, either occurring in wound fluid from acute wounds, or generated in human plasma during *P. aeruginosa* infection, bind to the bacteria similarly to the above described antibacterial C-terminal peptide GKY25 (FIG. 4C). Similar results were obtained using *S. aureus* (FIG. 8). Second, electron microscopy studies employing gold-labeled antibodies demonstrated that TCPs are predominantly associated with bacterial surfaces ex vivo and in vivo. Thus, *P. aeruginosa* grown in plasma or acute wound fluid exhibited disintegrated areas as shown by ejected cytoplasmic material and membrane blebs (FIG. 4D, see P and AWF). Furthermore, C-terminal epitopes of thrombin were found particularly in association with these damaged zones. Similar findings were seen after incubating *P. aeruginosa* with wound fluid derived from patients with chronic ulcers (FIG. 4D, CWF), as well after incubating the bacteria with the C-terminal thrombin peptide GKY25 (FIG. 9). Bacteria grown in plasma or acute wound fluid supplemented with heparin (shown to block the antimicrobial effects of the two C-terminal, heparin-binding peptides of thrombin described above, GKY25 and VFR17) were similar to the control bacteria, and did not exhibit either binding of TCPs or membrane damage (FIG. 9). Additionally, analysis of fibrin slough from a patient with a chronic ulcer infected with *P. aeruginosa* and *S. aureus*, identified multiple coccoid bacteria both extracellularly and inside phagocytes (FIG. 4D, CWS; FIG. 10), that all displayed significant binding of immunogold antibodies, demonstrating the existence of TCPs at bacterial surfaces in vivo in fibrin from human wounds. FIG. 4E (upper panel) further shows that the growth of *P. aeruginosa* is significantly enhanced in plasma depleted of prothrombin, when compared with native control plasma. Furthermore, addition of physiological concentrations of prothrombin, or the peptide GKY25 (at 1.5 µM, equivalent to the physiological prothrombin concentration), restored the suppressive effect of plasma on bacterial growth. Acute wound fluid depleted of thrombin and C-terminal fragments also showed increased growth of *P. aeruginosa* when compared with the control (FIG. 4E, lower panel). Similar results were obtained with *S. aureus* (FIG. 8C). Taken together, these results, and given the above findings on the generation and binding of TCPs to bacteria ex vivo and in vivo, unequivocally demonstrate a direct link between occurrence of TCPs and suppression of bacterial growth in plasma.

Further experiments with the model C-terminal peptide GKY25, exhibiting antibacterial activities similar to the endogenously produced C-terminal peptide HVF18 (peptide 47, FIG. 2A), were employed in order to further study a physiological, as well as therapeutical role of TCPs. The MIC-levels of GKY25, according to standard NCSLA-protocols, were comparable to, and in some cases lower than, those observed for LL-37 and omiganan (Table S2). Since the latter is a highly active and broad-spectrum designed antimicrobial peptide now in Phase III clinical studies, the data on GKY25 also implied a possible therapeutic role for TCPs. Initial studies revealed no significant permeabilizing effects of GKY25 on human erythrocytes (60-120 µM peptide) as well as keratinocytes (up to 60 µM peptide) in plasma and serum conditions, respectively (FIG. 11). In order to investigate a possible in vivo function of GKY25, we therefore injected this peptide subcutaneously into mice infected intraperitoneally with *P. aeruginosa*. Compared to the controls, treatment with GKY25 yielded a significant increase in survival (FIG. 4F) and significantly lower bacterial numbers in the spleen and kidney of the animals (FIG. 4G). Taken together, these results demonstrate that TCPs constitute a previously undisclosed neo-structure of thrombin, formed in vitro as well as ex vivo in plasma, but also in vivo in human wound fluid and fibrin, exerting activities at physiological concentrations in plasma, and finally, showing significant therapeutic potential.

Immunomodulatory Roles of TCPs

As mentioned above, recent evidence shows that HDPs trigger a range of immunomodulatory responses. The observation of LPS-binding of TCPs (FIG. 2D), prompted us to investigate possible endotoxin-neutralizing effects of the model peptide GKY25. Slot-binding experiments showed that the peptides bound heparin as well as LPS from *E. coli* and *P. aeruginosa* (FIG. 5A). In a mouse macrophage model, GKY25 significantly inhibited NO-release of LPS-stimulated macrophages (FIG. 5B), as well as release of TNF-α at concentrations below 2 µM (FIG. 12). Similar effects on TNF-α were noted using human monocyte-derived macrophages (not shown). In a mouse model of LPS-induced shock, GKY25 displayed a dramatic improvement on survival (FIG. 5C). Analyses of cytokines 6 hours after LPS injection, showed significant reductions of proinflammatory IL-6, IFN-γ, TNF-α, and IL-12p70, whereas IL-10 remained unchanged (FIG. 5D). SEM analyses of lungs from LPS-treated animals demonstrated pulmonary leakage of protein and red blood cells (see inset in FIG. 5E), an effect completely blocked by GKY25 (FIG. 5E). The results thus demonstrate that GKY25, like many HDPs, is multifunctional; in addition to its antimicrobial activity it also exerts potent anti-endotoxic and immunomodulatory effects.

Functional and Structural Studies of Thrombin-derived C-terminal Peptides

To examine possible peptide-induced permeabilization of bacterial plasma membranes, *P. aeruginosa* and *S. aureus* was incubated with GKY25 at concentrations yielding complete bacterial killing (30 µM), and analyzed by electron microscopy (FIG. 6A). Clear differences in morphology between peptide-treated bacteria and the control were demonstrated. The peptide caused local perturbations and breaks along *P. aeruginosa* and *S. aureus* plasma membranes, and intracellular material was found extracellularly. These findings were similar to those seen after treatment with LL-37 (FIG. 6A). The data suggest that GKY25 acts on bacterial membranes, but do not demonstrate the exact mechanistic events following peptide addition to bacteria, as secondary metabolic effects on bacteria may also trigger bacterial death and membrane destabilization. However, analogous results were also obtained using the impermeant dye FITC and *E. coli* as test bacterium (FIG. 6B) demonstrating membrane permeabilisation after exposure to GKY25. Kinetic studies showed that GKY25 killed >90% of bacteria after 10 minutes, compatible with a direct action on bacterial membranes (FIG. 13). Furthermore, circular dichroism (CD) spectroscopy was used to study the structure and the organization of the peptides GKY25 and VFR17 in solution and on interaction with negatively charged (bacteria-like) liposomes as well as *E. coli* LPS. Neither GKY25 nor VFR17 adopted an ordered conformation in aqueous solution, however the CD spectra revealed significant structural change, largely induction of helicity, taking place in the presence of negatively charged liposomes (FIG. 6C), and *E. coli* LPS (FIG. 6D). Compatible with earlier results, LL-37 displayed some helicity also in buffer solution [26]. Similarly to LL-37, the two thrombin-derived peptides induced leakage of liposomes, also at high ionic strength (FIG. 5E). Kinetic analysis showed that ~80% of the maximum leakage was reached within ~200 seconds for the two thrombin-derived peptides (at 1 µM) (not shown). Considering the above results with GKY25 and VFR17, both containing the crucial helical (and antimicrobial) epitope, the results therefore indicate that TCPs function like most helical AMPs such as LL-37 [5,27], by interactions with both the lipid membrane and LPS (possibly also peptidoglycan) at bacterial surfaces, leading to induction of an α-helical conformation, which in turn facilitates membrane interactions, membrane destabilization, and bacterial killing.

The TCP Structure Complies with a γ-core Motif and is Evolutionary Conserved

Recently, a multidimensional signature, the γ-core motif, was identified in multiple classes of cystein-containing AMPs [28]. Analysis showed that the 96aa TCP is closely related to this fundamental motif so common in various HDPs (FIG. 14). Furthermore, this region of thrombin is highly conserved in various species (FIG. 15). Next, we compared the antibacterial activities of C-terminal peptide GKY25 of thrombin with corresponding peptides from other closely related human coagulation factors (FIG. 6F, for sequences see Table S3). Whereas the peptide from thrombin (Factor II), as well as peptides from factors X and IX were antimicrobial against Gram-negative *P. aeruginosa* and *E. coli*, Gram-positive *S. aureus* and *B. subtilis*, as well as the fungus *C. albicans* (FIG. 6F), corresponding peptides from factor XI and kallikrein were inactive against these microbes (not shown). As seen in the 3D model (FIG. 6G), the coagulation factors (II, X, IX) share a similar overall structure with a helical C-terminal "tail". Indeed, C-terminals of these factors, as well as factor XI and kallikrein, contain a pattern sequence {DS}-X-[PFY]-G-[FIV]-Y-T-X-V-{C}-[AEQRY]-X-{R}-X-W-[IL]-X-{H}-X(4,24) [SEQ ID NO: 10], which describes an amphipathic structure. However, only factors II, X, IX have a positive net charge (+3 or more) in this region (Table S3), thus in perfect agreement with the data obtained on the antimicrobial activity (FIG. 6F). Taken together, these analyses show that the TCP molecule represents a novel structural entity, which is related to other cysteine-linked HDPs containing the γ-core motif, and also found in closely related coagulation factors.

Discussion

The key finding in this report is the discovery of a novel function of thrombin-derived C-terminal peptides in host defense. The findings expand the field of innate immunity to thrombin and the coagulation system. From an evolutionary perspective, this function of thrombin is logical, since injury and infection both represent situations necessitating an optimized innate immune system. Hence, from the perspective of wounding, thrombin, after fulfilling its primary function in generating a first line of defense, the fibrin clot, adds expanded functionality this natural physical shield by subsequent generation of antimicrobial and anti-endotoxic HDPs upon proteolysis. The significant and curative effect of a thrombin-derived peptide in a model of LPS-induced shock underscores the anti-inflammatory role this novel peptide, and contrasts to the pro-inflammatory actions of other HDPs, such as the anaphylatoxin C3a and chemotactic defensins [14,29]. Thus, during injury and infection, different pathways are activated, employing HDPs with multiple and sometimes opposite roles, all balancing and fine-tuning inflammation while counteracting microbial invasion. Recent evidence showing a significant cross-talk between the coagulation and complement systems [30] further adds biological relevance to the observed generation of C3a and various TCPs during inflammation.

TCPs further add to the increasingly recognized redundancy of host defense mechanisms, enforcing optimized control of the microbial flora by minimizing the risk for resistance development against one particular HDP, as well as protecting against detrimental effects due to specific HDP deficiencies. Notably, the observation of proteolytic formation of multiple TCP fragments of different lengths parallel previous findings on LL-37 and C3a [14,31], showing that these molecules are further processed while retaining their antimicrobial activity. Although not shown in this study, additional HDPs may be released from C-termini of factor X and XI, further increasing the arsenal of HDPs and adding to redundarcy. From an investigatory standpoint, such concerted action is challenging when it comes to defining roles of a given peptide in vivo. Nevertheless, the suppressive effects of formed TCPs on bacterial growth ex vivo, their association with bacterial surfaces ex vivo and in vivo, as well as significant effects of the TCP GKY25 under standard NCSLA conditions, as well as in an animal model of P. aeruginosa sepsis, clearly indicate an in vivo role for released TCPs. These findings, in concert with the anti-endotoxic and immunomodulatory effects of the peptides in vitro and in vivo, infer interesting therapeutic possibilities for TCPs in treatment of local and systemic infections, as well as sepsis. Recent evidence, showing a higher susceptibility to S. aureus infection in mice rendered thrombin-deficient [32], is also compatible with the new role in host-defense of thrombin-derived C-terminal peptides revealed here. Of relevance is also the increased susceptibility to infection after inhibition of the contact system, linked to abrogated release of kininogen-derived HDPs [16], but possibly also due to a reduced capability to form TCPs and other antimicrobial molecules associated with fibrin networks. Of particular clinical relevance is also the finding that TCPs are detected in wound fluids from patients with acute surgical wounds, as well as in patients with non-healing wounds. The latter patient group is characterized by an excessive bacterial colonization e.g. by P. aeruginosa, extensive proteolysis and inflammation [24]. Although speculative, the noted absence of TCPs in some patients could therefore be indicative of a defective host-defense and diminished control of released endotoxins (local or systemic). Thus, apart from therapeutic possibilities, the present findings provide a potential diagnostic marker for inflammation, which is currently under evaluation in larger patient groups. Concerning the immunomodulatory role of TCPs, it should be noted that although a direct binding and thus inhibition of LPS activity was demonstrated, the observed anti-inflammatory effects could also depend on additional effects by TCPs on various intracellular signaling pathways including inhibition of NF-kB activation.

From a structural standpoint, the TCP structure relates to the previously reported γ-core signature that characterize many cysteine-containing AMPs [28], further supporting the concept of multidimensional signatures in antimicrobial peptides and extending these also to HDPs of coagulation factors.

The high degree of conservation of the cysteine-constrained TCP-molecule during evolution also suggests that the TCP structure is, although novel to science, not necessarily new. Interestingly, the 96-amino acid TCP also contains a peptide region responsible for the well-known growth promoting activity of thrombin [33], further adding biological importance to the findings. It remains to be investigated whether thrombin fragments comprising this region promote cell-growth. If so, these TCPs, generated in response to injury mediate not only microbial evasion and immunomodulation, but also wound closure, three fundamental aspects of host defense.

Materials and Methods

Ethics Statement

The use of human wound materials was approved by the Ethics Committee at Lund University (LU 708-01, LU 509-01). Written informed consent was obtained from the participants. The animal experiments were conducted according to national guidelines (Swedish Animal Welfare Act SFS 1988: 534), and were approved by the Laboratory Animal Ethics Committee of Malmö/Lund.

Peptides and Proteins

Prothrombin and thrombin were from Innovative Research, USA. The coagulation factor-derived peptides (Table S3) and omiganan (ILRWPWWPWRRK-amide [SEQ ID NO: 11]) were synthesized by Biopeptide Co. The purity (>95%) and molecular weight of these peptides was confirmed by mass spectral analysis (MALDI.TOF Voyager). LL-37 (LLGDFFRKSKEKIGKEFKRIVQRIKDFL-RNLVPRTES [SEQ ID NO: 12]) was from Innovagen AB. 20mer peptides corresponding to various overlapping regions of prothrombin (FIG. 2) were from Sigma (Custom Peptide Libraries, SigmaGenosys).

Biological Materials

Wound fluids (100-600 μl) from patients with chronic venous leg ulcers were collected under a Tegaderm dressing for 2 h as previously described [25]. Fibrin slough from two chronic venous leg ulcers (chronic wound slough/surface, denoted CWS) was collected by a sterile spatula, and was immediately put into the fix solution for electron microscopy. Sterile wound fluids were obtained from surgical drainages after mastectomy. Collection was for 24 h, 24 to 48 h after operation. Wound fluids were centrifuged, aliquoted and stored at −20° C.

Microorganisms

Escherichia coli ATCC 25922, Pseudomonas aeruginosa ATCC 27853, Pseudomonas aeruginosa 15159, Staphylococcus aureus ATCC 29213, Bacillus subtilis ATCC 6633 bacterial isolates, and the fungal isolate Candida albicans ATCC 90028 were from the Department of Bacteriology, Lund University Hospital.

Radial Diffusion Assay

Essentially as described earlier [34,35], bacteria were grown to mid-logarithmic phase in ml of full-strength (3% w/v) trypticase soy broth (TSB) (Becton-Dickinson). The microorganisms were then washed once with 10 mM Tris, pH 7.4. Subsequently, $4\times10^8$ cfu were added to 15 ml of the underlay agarose gel, consisting of 0.03% (w/v) TSB, 1% (w/v) low electroendosmosis type (EEO) agarose (Sigma-Aldrich) and 0.02% (v/v) Tween 20 (Sigma-Aldrich). The underlay was poured into a Ø 144 mm petri dish. After agarose solidification, 4 mm-diameter wells were punched and 6 μl peptide solution of required concentration added to each well. Plates were incubated at 37° C. for 3 h to allow peptide diffusion. The underlay gel was then covered with 15 ml of molten overlay (6% TSB and 1% Low-EEO agarose in distilled H$_2$O). Antimicrobial activity of a peptide was visualized as a zone of clearing around each well after 18-24 h of incubation at 37° C.

Viable Count Assays and Analysis of Bacterial Growth

E. coli ATCC 25922 bacteria were grown to mid-logarithmic phase in Todd-Hewitt (TH) medium. Bacteria were washed and re-suspended in 10 mM Tris, pH 7.4 containing 5 mM glucose. E. coli ATCC 25922 (50 µl; 2×10$^6$ cfu/ml) were incubated, at 37° C. for 2 h with prothrombin, thrombin, GKY25, or VFR17 at 3 and 6 µM. For assessment of bacterial growth in plasma and effect of TCPs, overnight cultures (in TH) of P. aeruginosa 15159 and S. aureus ATCC 29213 bacteria were incubated (17 µl in 450 µl) with control plasma, acute wound fluid (AWF) or depleted AWF, plasma depleted of prothrombin (DP, Innovative Research), or DP supplemented with the peptide GKY25 (at 1.5 µM) for 0, 2, 4, and 6 h at 37° C. Serial dilutions of the incubation mixtures were plated on TH agar, followed by incubation at 37° C. overnight and cfu determination. In order to deplete acute wound fluids (AWF) of thrombin and fragments containing C-terminal peptides, AWF was diluted with an equal volume of PBS, and passaged 5 times through an affinity column (0.3 ml, Thermo Scientific) having coupled IgG antibodies specific for VFR17 (Innovagen AB). For control, a column with rabbit IgG was used.

Flow Cytometry Analysis

50 µl of overnight bacteria was added to 450 µl of human plasma, AWF, or DP either alone or supplemented with the peptide GKY25 (at 1.5 µM). Samples were incubated for 4 h at 37° C., centrifuged, washed with PBS, resuspended in 100 µl PBS with polyclonal antibodies against VFR17 (1:100), and subsequently incubated for one hour at room temperature. Bacteria were pelleted and washed twice with PBS, incubated in 100 µl PBS with goat anti rabbit IgG FITC-labeled antibodies (1:500, Sigma) for 30 min at room temperature and washed twice with PBS. Flow cytometry analysis (Becton-Dickinson, Franklin Lakes, N.J.) was performed using a FACS-Calibur flow cytometry system equipped with a 15 mW argon laser turned a 488 nm. The bacterial population was selected by gating with appropriate settings of forward scatter (FSC) and sideward scatter (SSC).

Slot-blot Assay

LPS-binding ability of the peptides was examined by a slot-blot assay. Peptides (2 and 5 µg) were bound to nitrocellulose membranes (Hybond-C, GE Healthcare BioSciences), pre-soaked in PBS. Membranes were then blocked by 2 wt % BSA in PBS, pH 7.4, for 1 h at room temperature, and subsequently incubated with $^{125}$I-labelled LPS (40 µg/ml; 0.13× 10$^6$ cpm/□g) for 1 h in PBS. After incubation, the membranes were washed 3 times, 10 min each time, in PBS and visualized for radioactivity on Bas 2000 radioimaging system (Fuji). Unlabeled heparin (6 mg/ml) was added for competition of binding.

Liposome Preparation and Leakage Assay

Dry lipid films were prepared by dissolving either dioleoylphosphatidylethanolamine (Avanti Polar Lipids, Alabaster, Ala.) (70 mol %) and dioleoylphosphatidylglycerol (30 mol %) in chloroform, and then removing the solvent by evaporation under vacuum overnight. Subsequently, buffer solution containing 10 mM Tris, pH 7.4, either with or without additional 150 mM NaCl, was added together with 0.1 M carboxyfluorescein (CF) (Sigma). After hydration, the lipid mixture was subjected to eight freeze-thaw cycles consisting of freezing in liquid nitrogen and heating to 60° C. Unilamellar liposomes with a diameter of about 130 nm (as found with cryo-TEM; results not shown) were generated by multiple extrusions through polycarbonate filters (pore size 100 nm) mounted in a LipoFast miniextruder (Avestin). Untrapped carboxyfluorescein was then removed by filtration through two subsequent Sephadex G-50 columns with the relevant Tris buffer as eluent. Both extrusion and filtration was performed at 22° C. The CF release was monitored by fluorescence at 520 nm from a liposome dispersion (10 mM lipid in 10 mM Tris pH 7.4). An absolute leakage scale is obtained by disrupting the liposomes at the end of the experiment through addition of 0.8 mM Triton X100 (Sigma), thereby causing 100% release and dequenching of CF. A SPEX-fluorolog 1650 0.22-m double spectrometer (SPEX Industries) was used for the liposome leakage assay.

CD-spectroscopy

Circular dichroism (CD) spectra were measured by a Jasco J-810 Spectropolarimeter (Jasco, Easton, USA). The measurements were performed in triplicate at 37° C. in a 10 mm quartz cuvette under stirring with a peptide concentration of 100M. The effect on peptide secondary structure of liposomes at a lipid concentration of 10 □M, and of E. coli LPS at a concentration of 0.02 wt %; was monitored in the range 200-250 nm. To account for instrumental differences between measurements, the background value (detected at 250 nm, where no peptide signal is present) was subtracted. Signals from the bulk solution were also corrected for.

Fluorescence Microscopy

For study of membrane permeabilization using the impermeant probe FITC, E. coli ATCC 25922 bacteria were grown to mid-logarithmic phase in TSB medium. The bacteria were washed and resuspended in either 10 mM Tris, pH 7.4, 10 mM glucose, to yield a suspension of 1×10$^7$ cfu/ml. 100 µl of the bacterial suspension was incubated with 30 µM of the respective peptides at 30° C. for 30 min. Microorganisms were then immobilized on poly (L-lysine)-coated glass slides by incubation for 45 min at 30° C., followed by addition onto the slides of 200 µl of FITC (6 µg/ml) in the appropriate buffers and incubated for 30 min at 30° C. The slides were washed and bacteria fixed by incubation, first on ice for 15 min, then in room temperature for 45 min in 4% paraformaldehyde. The glass slides were subsequently mounted on slides using Prolong Gold antifade reagent mounting medium (Invitrogen). For fluorescence analysis, bacteria and fungi were visualized using a Nikon Eclipse TE300 (Nikon, Melville, N.Y.) inverted fluorescence microscope equipped with a Hamamatsu C4742-95 cooled CCD camera (Hamamatsu) and a Plan Apochromat ×100 objective (Olympus, Orangeburg, N.Y.). Differential interference contrast (Nomarski) imaging was used for visualization of the microbes themselves.

Electron Microscopy

For transmission electron microscopy and visualization of peptide effects on bacteria, P. aeruginosa ATCC 27853 and S. aureus ATCC 29213 (1–2×10$^8$ cfu/sample) were incubated for 2 h at 37° C. with the peptide GKY25 at 30 µM. LL-37 (30 µM) was included as a control. Samples of P. aeruginosa and S. aureus suspensions were adsorbed onto carbon-coated copper grids for 2 min, washed briefly on two drops of water, and negatively stained on two drops of 0.75% uranyl formate. The grids were rendered hydrophilic by glow discharge at low pressure in air. For analysis of effects on biological fluids on bacterial integrity as well as detection of bound TCPs, P. aeruginosa 15159 bacteria, grown overnight in TH, were washed and resuspened in PBS (1×10$^9$ cfu/ml). Equal volumes of bacterial suspension and chronic wound fluids were incubated together for 30 min at 37° C. For control, 2 µM of GKY25 was incubated with bacteria for 30 min at 37° C. In another experiment, *P. aeruginosa* 15159 bacteria were directly added to citrate plasma or AWF in the absence or presence of heparin (100 μg/ml), and further incubated for 4 h at 37° C. All the samples were centrifuged and washed with PBS and re-suspended in 4% paraformaldehyde and stored at 4° C., followed by gold labeling. Fibrin slough from patients with chronic venous ulcers (CWS) was fixed (1.5% PFA, 0.5% GA in 0.1 M phosphate buffer, pH 7.4) for 1 hour at room temperature, followed by washing with 0.1 M phosphate buffer, pH 7.4. The fixed and washed samples were subsequently dehydrated in ethanol and further processed for Lowicryl embedding [36]. Sections were cut with a LKB ultratome and mounted on gold grids. For immunostaining, the grids were floated on top of drops of immune reagents displayed on a sheet of parafilm. Free aldehyde groups were blocked with 50 mM glycine, and the grids were then incubated with 5% (vol/vol) goat serum in incubation buffer (0.2% BSA-c in PBS, pH 7.6) for minutes. This blocking procedure was followed by overnight incubation with 1 μg/ml of VFR17 polyclonal antibodies at 4° C. Controls without these primary antibodies were included. After washing the grids in a large volume (200 ml) of incubation buffer, floating on drops containing the gold conjugate reagents, 1 μg/ml EM goat antiRabbit IgG 10 nm Au (BBI) in incubation buffer was performed for 2 h at 4° C. After further washes by an excess volume of incubation buffer, the sections were postfixed in 2% glutaraldehyde. Finally, sections were washed with distilled water and poststained with 2% uranyl acetate and lead citrate. All samples were examined with a Jeol JEM 1230 electron microscope operated at 80 kV accelerating voltage. Images were recorded with a Gatan Multiscan 791 charge-coupled device camera.

Degradation of Prothrombin and Thrombin

Prothrombin and thrombin (Innovative Research) (27 μg, 0.6 mg/ml) was incubated at 37° C. with human neutrophil elastase (NE) (0.6 μg, 20 units/mg) (Sigma) and prothrombin also with cathepsin G (0.5 μg, 2 units/mg) (BioCol GmbH) or *P. aeruginosa* elastase (PAE) (30 mU, a generous gift from Dr. H. Maeda, Kumamoto University, Japan) in a total volume of 45 μl 10 mM Tris, pH 7.4 for different time periods as indicated in the figures. Neutrophils; were prepared by routine procedures (Polymorphprep) from blood obtained from healthy human donors. The cells were disrupted by freeze-thawing and addition of 0.3% Tween 20. Neutrophil extracts (corresponding to $4.8 \times 10^7$ cells) were incubated at 37° C. with thrombin (27 μg, 0.6 mg/ml) for 180 min. The reaction was stopped by boiling at 95° C. for 3 min. 6 μl (3.6 μg) of the material was analysed by RDA and 20 μl (12 μg) fractions analysed by SDS-PAGE using 16.5% precast Tris-tricine gels (Bio-rad), run under non-reducing or reducing conditions. The gels were stained with Coomassie brilliant blue and destained.

Definition of Cleavage Products of Thrombin

Peptide fragments of thrombin, digested by neutrophil elastase for 30 min, were separated by hplc (PerkinElmer Series 200) on a reversed phase column (Vydac 218TPC18, 250×4.6 mm, 5 μm) (Dalco chromtech AB). After injection, samples were eluted with a gradient of acetonitrile in 0.1% aqueous trifluoroacetic acid at 1 ml per minute. Fractions were collected and stored at −80° C. Samples were freeze-dried, redissolved in water, and analyzed by RDA, SDS-PAGE, immunoblotting and gel-overlay assay (FIG. 3). Active fractions were analysed by combinations of MALDI-TOF MS, ESI-MS/MS, N- and C-terminal sequencing at the Karolinska Institutet Protein Analysis Center (PAC Stockholm). See also legend to FIG. 3 for additional information.

SDS-PAGE and Immunoblotting

Prothrombin and thrombin, either intact or subjected to enzymes, were analyzed by SDS-PAGE on 16.5% Tris-tricine gels (Bio-Rad). Proteins and peptides were transferred to nitrocellulose membranes (Hybond-C). Membranes were blocked by 3% (w/v) skimmed milk, washed, and incubated for 1 h with rabbit polyclonal antibodies recognizing the peptide VFR17 (1:800) (Innovagen AB) or rabbit antibodies of similar specificity (1:1000) (Dako), washed three times for 10 min, and subsequently incubated (1 h) with HRP-conjugated secondary antibodies (1:2000) (Dako), and then washed again three times, each time for 10 min. C-terminal thrombin peptides were visualized by an enhanced chemiluminesent substrate (LumiGLO®) developing system (Upstate cell signaling solutions). For identification of TCPs in human fibrin, normal citrate-plasma was supplemented with 10 mM $Ca^{2+}$ in eppendorf tubes at 37° C. overnight. The clots formed were washed three times with PBS and incubated with human neutrophil elastase (20 units/mg) for 0, 1, and 3 h at 37° C. Samples were centrifuged at 10000 RPM for 10 min, after which supernatants and pellets were separated. Samples were freeze-dried and then redissolved in 60% acetonitrile and 0.1% aqueous TFA. Pooled samples were freeze-dried, redissolved in water and analysed by SDS-PAGE followed by immunoblotting as above. For identification of TCPs in human citrate plasma, 1.5 μl of citrate-plasma or patient would fluids were analysed by SDS-PAGE under reducing conditions, followed by immunoblotting as above. For identification of TCPs bound to bacteria, overnight cultures of *P. aeruginosa* 15159 bacteria were washed, resuspended, and incubated with human plasma or a preformed fibrin clot[37] for 4 h at 37° C. The bacterial cells were collected, washed wih PBS, and bound proteins were eluted with 0.1 M glycine-HCL, pH 2.0. The pH of the eluted material was raised to 7.5 with the addition of 1 M Tris. Eluted proteins were precipitated with 5% trichloroacetic acid (TCA) for 30 min on ice followed by centrifugation at 15 000 g (4° C. for 20 min). Precipitated material was dissolved in SDS sample buffer and subjected to Tris-Tricine SDS-PAGE under reducing conditions, followed by immunoblotting as above.

Gel-overlay Assay

Gel overlay assay was performed essentially as described previously [35]. Briefly, duplicate samples were run on non-denaturing acid urea (AU-PAGE) gels in 5% acetic acid at 100 V for 1 h 15 min. Bacteria were grown overnight in TH broth, inoculated, and grown until the OD was 0.4. The bacteria were washed and resuspended in 10 mM Tris, pH 7.4. Bacteria ($4 \times 10^8$) were added to 12 ml melted underlay agarose (10 mM Tris, pH 7.4, 0.03% TH broth, 1% agarose type 1 (Sigma-Aldrich)) and poured into a square petri dish. One AU gel was stained with Coomassie brilliant blue and one AU gel was washed three times for 4 min in 10 mM Tris, pH 7.4 and then placed on top of the agarose gel and incubated for 3 h at 37° C. The AU gel was then removed and an overlay agarose (6% TH broth, 1% agarose type 1) was poured on top of the underlay and incubated overnight at 37° C. To make the clearing zones more visible, the agarose was stained with Coomassie brilliant blue and then destained with water.

Animal Infection Model

Animals were housed under standard conditions of light and temperature and had free access to standard laboratory chow and water. *P. aeruginosa* 15159 bacteria were grown overnight, harvested, washed in PBS, diluted in the same buffer to $2 \times 10^8$ cfu/ml, and kept on ice until injection. Hundred microliter of the bacterial suspension were injected intraperitoneally (ip) into female BALB/c mice. Sixty minutes after the bacterial injection, 0.5 mg GKY25 or buffer alone was injected sc into the mice. This was repeated after 24 hours. In this *Pseudomonas* infection model, infected mice develop severe signs of sepsis within 1-2 days and usually do not recover from the infection. In order to study bacterial dissemination to target organs, the mice were infected as previously described and after a time period of 8 hours, spleen and kidney were harvested, placed on ice, homogenized, and colony-forming units determined. The P-value was determined using the Mann-Whitney U-test. Data from three independent experiments were pooled.

LPS Effects on Macrophages In vitro $3.5 \times 10^5$ cells were seeded in 96-well tissue culture plates (Nunc, 167008) in phenol red-free DMEM (Gibco) supplemented with 10% FBS and antibiotics. Following 6 hours of incubation to permit adherence, cells were stimulated with 100 or 10 ng/mL *E. coli* (0111:B4) or *P. aeruginosa* LPS (Sigma), with and without peptide of various doses. The levels of NO in culture supernatants were determined after 24 hours from stimulation using the Griess reaction [38]. Briefly, nitrite, a stable product of NO degradation, was measured by mixing 50 µl of culture supernatants with the same volume of Griess reagent (Sigma, G4410) and reading absorbance at 550 nm after 15 min. Phenol-red free DMEM with FBS and antibiotics were used as a blank. A standard curve was prepared using 0-80 µM sodium nitrite solutions in $ddH_2O$.

LPS Model In vivo

C57BL16 mice (8-10 weeks, 22+/−5 g), divided into weight and sex matched groups, were injected intraperitoneally with 18 mg *E. coli* 0111:B4 LPS (Sigma) per kg of body weight. Thirty minutes after LPS injection, 0.2 mg GKY25 or buffer alone was intraperitoneally into the mice. Survival and status was followed during seven days. For the cytokine assay, mice were sacrificed 6 hours post LPS challenge, and blood was collected by cardiac puncture. For SEM, mice were sacrificed 20 h after LPS challenge, and lungs were removed and fixed. The Laboratory Animal Ethics Committee of MalmÖ/Lund has approved the animal experiments.

Cytokine Assay

The cytokines IL-6, IL-10, MCP-1, INF-☐, TNF, and IL-12p70 were measured in plasma from LPS-infected mice (with or without GKY25 treatment) using the Cytometric bead array; mouse inflammation kit (Becton Dickinson AB) according to the manufacturer's instructions.

Statistical Analysis

Bar diagrams (RDA, VCA) are presented as mean and standard deviation, from at least three independent experiments. Animal data are presented as dot plots, with mean for normally distributed data, or median for data, which do not meet the criteria for normal distribution. Outliers were not excluded from the statistical analysis. Differences with P<0.05 were considered statistically significant MIC, Hemolysis, MTT, and LDH Assay MIC assay was carried out by a microtiter-broth dilution method as previously described in the NCSLA guidelines [39]. Hemolysis, MTT, and LDH assays were performed as previously described [40] (Supplementary data).

Alignment of TCPs

See Supplementary data below.

Supplementary Data

Methods

Minimal Inhibitory Concentration (MIC) Determination

MIC assay was carried out by a microtiter broth dilution method as previously described in the NCSLA guidelines (Wiegand, I., Hilpert, K. & Hancock, R. E. Agar and broth dilution methods to determine the minimal inhibitory concentration (MIC) of antimicrobial substances. *Nat Protoc* 3, 163-175 (2008)). In brief, fresh overnight colonies were suspended to a turbidity of 0.5 units and further diluted in Mueller-Hinton broth (Becton Dickinson). For determination of MIC, peptides were dissolved in water at concentration 10 times higher than the required range by serial dilutions from a stock solution. Ten µl of each concentration was added to each corresponding well of a 96-well microtiter plate (polypropylene, Costar Corp.) and 90 µl of bacteria ($1 \times 10^5$) in MH medium added. The plate was incubated at 37° C. for =16-18 h. MIC was taken as the lowest concentration where no visual growth of bacteria was detected.

Hemolysis Assay

EDTA-blood was diluted (1:1) with PBS. The cells were then incubated with end-over-end rotation for 1 h at 37° C. in the presence of peptides (60 and 120 µM). 2% Triton X-100 (Sigma-Aldrich) served as positive control. The samples were then centrifuged at 800 g for 10 min. The absorbance of hemoglobin release was measured at λ 540 nm and is in the plot expressed as % of TritonX-100 Induced hemolysis.

Lactate Dehydrogenase (LDH) Assay

HaCaT keratinocytes were grown in 96 well plates (3000 cells/well) in serum free keratinocyte medium (SFM) supplemented with bovine pituitary extract and recombinant EGF (BPE-rEGF) (Invitrogen, USA) to confluency. The medium was then removed, and 100 µl of the peptides investigated (at 3, 6, 30 and 60 µM, diluted in SFM/BPE-rEGF with 20% human serum), were added in triplicates to different wells of the plate, and incubations were performed for 16 h. The LDH based TOX-7 kit (Sigma-Aldrich, St Louis, USA) was used for quantification of LDH release from the cells. Results given represent mean values from triplicate measurements. Results are given as fractional LDH release compared to the positive control consisting of 1% Triton X-100 (yielding 100% LDH release).

MTT Assay

Sterile filtered MTT (3-(4,5-dimethylthiazolyl)-2,5-diphenyl-tetrazolium bromide; Sigma-Aldrich) solution (5 mg/ml in PBS) was stored protected from light at −20° C. until usage. HaCaT keratinocytes, 3000 cells/well, were seeded in 96 well plates and grown in keratinocyte-SFM/BPE-rEGF medium to confluency. Peptides were then added at the concentrations indicated in the figure (in the same medium supplemented with 20% human serum). After incubation for 16 h, 20 µl of the MTT solution was added to each well and the plates incubated for 1 h in $CO_2$ at 37° C. The MTT containing medium was then removed by aspiration. The blue formazan product generated was dissolved by the addition of 100 µl of 100% DMSO per well. The plates were then gently swirled for 10 min at room temperature to dissolve the precipitate. The absorbance was monitored at 550 nm, and results given represent mean values from triplicate measurements.

Alignment of TCPs

The prothrombin amino acid sequence was retrieved from the NCBI site. Each sequence was analyzed with Psi-Blast (NCBI) to find the ortholog and paralog sequences. Sequences that showed structural homology >70% were selected. These sequences were aligned using ClustalW using Blosum 69 protein weight matrix settings. Internal adjustments were made taking the structural alignment into account utilizing the ClustalW interface. The level of consistency of each position within the alignment was estimated by using the alignment-evaluating software Tcoffee.

Tables

TABLE S1

Peptide sequences of fraction 20-21.

| MALDI mass | DB mass | Δ mass (daltons) | Peptide |
|---|---|---|---|
| colspan="4" | Fraction 20 | | |
| 975.000 | 974.517 | -0.483 | (Y)KGRVTGWGN(L) [SEQ ID NO: 13] |
| 1581.510 | 1581.869 | 0.358 | (Y)GFYTHVFRLKKW(I) [SEQ ID NO: 14] |
| 1581.510 | 1581.974 | 0.463 | (T)HVFRLKKWIQKV(I) [SEQ ID NO: 15] |
| 2243.000 | 2243.089 | 0.088 | (F)VMKSPFNNRWYQMGIVSW(G) [SEQ ID NO: 16] |
| 2502.000 | 2502.108 | 0.107 | (K)SPFNNRWYQMGIVSWGEGCD R(D) [SEQ ID NO: 17] |
| 4076.000 | 4075.846 | -0.153 | (V)MKSPFNNRWYQMGIVSWGEG CDRDGKYGFYTHVF(R) [SEQ ID NO: 18] |
| colspan="4" | Fraction 21 | | |
| 975.000 | 974.517 | -0.483 | (Y)KGRVTGWGN(L) [SEQ ID NO: 19] |
| 1189.510 | 1189.579 | 0.068 | (K)YGFYTHVFR(L) [SEQ ID NO: 20] |
| 1739.690 | 1739.796 | 0.105 | (F)NNRWYQMGIVSWGE(G) [SEQ ID NO: 21] |
| 2536.090 | 2536.331 | 0.240 | (A)SLLQAGYKGRVTGWGNLKET WTA(N) [SEQ ID NO: 22] |

Masses were obtained by MALDI-MS analysis, and possible peptide sequences from the prothrombin sequence were deduced using the FINDPEPT tool (www.expasy.org/tools/findpept.html).

TABLE S2

Minimal inhibitory concentrations (MIC) of GKY25, LL-37 and omiganan against various bacterial isolates.

| Bacteria | | MIC in (μM) | | |
|---|---|---|---|---|
| | | GKY25 | LL-37 | Omiganan |
| E. coli | ATCC 25922 | 2.5 | 20 | 20 |
| | Clinical isolate 37.4 | 2.5 | 5 | 20 |
| | Clinical isolate 47.1 | 1.2 | 5 | 20 |
| | Clinical isolate 49.1 | 10 | 10 | 10 |
| P. aeruginosa | ATCC 27853 | 160 | 10 | 160 |
| | Clinical isolate 15159 | 20 | 20 | 20 |
| | Clinical isolate 13.2 | 80 | 10 | 40 |
| | Clinical isolate 27.1 | 20 | 10 | >160 |
| | Clinical isolate 23.1 | 40 | 20 | 40 |
| | Clinical isolate 10.5 | 20 | 10 | 40 |
| | Clinical isolate 51.1 | 80 | 40 | 80 |
| | Clinical isolate 62.1 | 20 | 20 | 20 |
| | Clinical isolate 18488 | 10 | 20 | 20 |
| S. aureus | ATCC 29213 | 10 | 40 | 10 |
| | FDA 486 | 10 | 10 | 20 |
| | Clinical isolate 1088 | 10 | 160 | 20 |
| | Clinical isolate 1090 | 10 | 160 | 80 |
| | Clinical isolate 1086 | 80 | 20 | 10 |
| | Clinical isolate 16065 | 2.5 | 10 | 5 |
| | Clinical isolate 13430 | 10 | 20 | 10 |
| | Clinical isolate 14312 | 10 | 10 | 20 |
| | Clinical isolate 18800 | 2.5 | 5 | 2.5 |
| | Clinical isolate 18319 | 2.5 | 10 | 20 |
| E. faecalis | Clinical isolate 2374 | 20 | >160 | 160 |
| S. pyogenes | AP1 | 2.5 | 1.2 | 5 |

The analysis was performed as described in Wiegand et al. and according to NCSLA guidelines. Additional clinical isolates were obtained from the Department of Bacteriology, Lund University Hospital. P. aeruginosa, E. coli and E. faecalis isolates were initially derived from patients with chronic ulcers, S. aureus from patients with atopic dermatitis. The S. pyogenes strain AP1 was from the WHO Collaborating Center for References and Research on Streptococci (Prague, Czech Republic).

TABLE S3

Sequences of coagulation factor-derived peptides.

| Protein | Designation | Sequence | net charge |
|---|---|---|---|
| Thrombin (FII) | GKY25 | GKYGFYTHVFRLKKWIQKVIDQFGE | +3 |
| | VFR17 | VFRLKKWIQKVIDQFGE [SEQ ID NO: 6] | +2 |
| FX | GKY25(X) | GKYGIYTKVTAFLKWIDRSMKTRGL [SEQ ID NO: 23] | +5 |
| FIX | GKY23 | GKYGIYTKVSRYVNWIKEKTKLT [SEQ ID NO: 24] | +5 |

TABLE S3-continued

Sequences of coagulation factor-derived peptides.

| Protein | Designation | Sequence | net charge |
|---|---|---|---|
| FXI | ERP23 | ERPGVYTNVVEYVDWILEKTQAV [SEQ ID NO: 25] | −2 |
| Kallikrein | EQP25 | EQPGVYTKVAEYMDWILEKTQSSDG [SEQ ID NO: 26] | −3 |

REFERENCES

1. Lehrer R I, Ganz T (2002) Cathelicidins: a family of endogenous antimicrobial peptides. Curr Opin Hematol 9: 18-22.
2. Harder J, Glaser R, Schröder J M (2007) Review: Human antimicrobial proteins effectors of innate immunity. J Endotoxin Res 13: 317-338.
3. Zasloff M (2002) Antimicrobial peptides of multicellular organisms. Nature 415: 389-395.
4. Tossi A, Sandri L, Giangaspero A (2000) Amphipathic, alpha-helical antimicrobial peptides. Biopolymers 55: 4-30.
5. Yount N Y, Bayer A S, Xiong Y Q, Yeaman M R (2006) Advances in antimicrobial peptide immunobiology. Biopolymers.
6. Zanetti M (2004) Cathelicidins, multifunctional peptides of the innate immunity. J Leukoc Biol 75: 39-48.
7. Elsbach P (2003) What is the real role of antimicrobial polypeptides that can mediate several other inflammatory responses? J Clin Invest 111: 1643-1645.
8. Ganz T (2003) Defensins: antimicrobial peptides of innate immunity. Nat Rev Immunol 3: 710-720.
9. Cole A M, Ganz T, Liese A M, Burdick M D, Liu L, et al. (2001) Cutting edge: IFN-inducible ELR-CXC chemokines display defensin-like antimicrobial activity. J Immunol 167: 623-627.
10. Brogden K A (2005) Antimicrobial peptides: pore formers or metabolic inhibitors in bacteria? Nat Rev Microbiol 3: 238-250.
11. Kowalska K, Carr D B, Lipkowski A W (2002) Direct antimicrobial properties of substance P. Life Sci 71: 747-750.
12. Mor A, Amiche M, Nicolas P (1994) Structure, synthesis, and activity of dermaseptin b, a novel vertebrate defensive peptide from frog skin: relationship with adenoregulin. Biochemistry 33: 6642-6650.
13. Malmsten M, Davoudi M, Walse B, Rydengard V, Pasupuleti M, et al. (2007) Antimicrobial peptides derived from growth factors. Growth Factors 25: 60-70.
14. Nordahl E A, Rydengard V, Nyberg P, Nitsche D P, Morgelin M, et al. (2004) Activation of the complement system generates antibacterial peptides. Proc Natl Acad Sci USA 101: 16879-16884.
15. Pasupuleti M, Walse B, Nordahl E A, Morgelin M, Malmsten M, et al. (2007) Preservation of antimicrobial properties of complement peptide C3a, from invertebrates to humans. J Biol Chem 282: 2520-2528.
16. Frick I M, Akesson P, Herwald H, Morgelin M, Malmsten M, et al. (2006) The contact system—a novel branch of innate immunity generating antibacterial peptides. Embo J 25: 5569-5578.
17. Nordahl E A, Rydengard V, Morgelin M, Schmidtchen A (2005) Domain 5 of high molecular weight kininogen is antibacterial. J Biol Chem 280: 34832-34839.
18. Rydengard V, Andersson Nordahl E, Schmidtchen A (2006) Zinc potentiates the antibacterial effects of histidine-rich peptides against *Enterococcus faecalis*. Febs J 273: 2399-2406.
19. Davie E W, Kulman J D (2006) An overview of the structure and function of thrombin. Semin Thromb Hemost 32 Suppl 1: 3-15.
20. Bode W (2006) The structure of thrombin: a janus-headed proteinase. Semin Thromb Hemost 32 Suppl 1: 16-31.
21. Brower M S, Walz D A, Garry K E, Fenton J W, 2nd (1987) Human neutrophil elastase alters human alpha-thrombin function: limited proteolysis near the gamma-cleavage site results in decreased fibrinogen clotting and platelet-stimulatory activity. Blood 69: 813-819.
22. Schmidtchen A, Hoist E, Tapper H, Bjorck L (2003) Elastase-producing *Pseudomonas aeruginosa* degrade plasma proteins and extracellular products of human skin and fibroblasts, and inhibit fibroblast growth. Microb Pathog 34: 47-55.
23. Liu C Y, Nossel H L, Kaplan K L (1979) The binding of thrombin by fibrin. J Biol Chem 254: 10421-10425.
24. Lundqvist K, Herwald H, Sonesson A, Schmidtchen A (2004) Heparin binding protein is increased in chronic leg ulcer fluid and released from granulocytes by secreted products of *Pseudomonas aeruginosa*. Thromb Haemost 92: 281-287.
25. Schmidtchen A (2000) Degradation of antiproteinases, complement and fibronectin in chronic leg ulcers. Acta Derm Venereol 80: 179-184.
26. Oren Z, Lerman J C, Gudmundsson G H, Agerberth B, Shai Y (1999) Structure and organization of the human antimicrobial peptide LL-37 in phospholipid membranes: relevance to the molecular basis for its non-cell-selective activity. Biochem J 341: 501-513.
27. Zelezetsky I, Tossi A (2006) Alpha-helical antimicrobial peptides-Using a sequence template to guide structure-activity relationship studies. Biochim Biophys Acta.
28. Yount N Y, Yeaman M R (2004) Multidimensional signatures in antimicrobial peptides. Proc Natl Acad Sci USA 101: 7363-7368.
29. Oppenheim J J, Yang D (2005) Alarmins: chemotactic activators of immune responses. Curr Opin Immunol 17: 359-365.
30. Amara U, Rittirsch D, Flied M, Bruckner U, Klos A, et al. (2008) Interaction between the coagulation and complement system. Adv Exp Med Biol 632: 71-79.
31. Murakami M, Lopez-Garcia B, Braff M, Dorschner R A, Gallo R L (2004) Postsecretory processing generates multiple cathelicidins for enhanced topical antimicrobial defense. J Immunol 172: 3070-3077.
32. Mullins E S, Kombrinck K W, Talmage K E, Shaw M A, Witte D P, et al. (2009) Genetic elimination of prothrombin in adult mice is not compatible with survival and results in spontaneous hemorrhagic events in both heart and brain. Blood 113: 696-704.

33. Glenn K C, Frost G H, Bergmann J S, Carney D H (1988) Synthetic peptides bind to high-affinity thrombin receptors and modulate thrombin mitogenesis. Pept Res 1: 65-73.
34. Andersson E, Rydengard V, Sonesson A, Mörgelin M, Björck L, et al. (2004) Antimicrobial activities of heparin-binding peptides. Eur J Biochem 271: 1219-1226.
35. Lehrer R I, Rosenman M, Harwig S S, Jackson R, Eisenhauer P (1991) Ultrasensitive assays for endogenous antimicrobial polypeptides. J Immunol Methods 137: 167-173.
36. Carlemalm E, Villiger W, Hobot J A, Acetarin J D, Kellenberger E (1985) Low temperature embedding with Lowicryl resins: two new formulations and some applications. J Microsc 140: 55-63.
37. Rydengard V, Shannon O, Lundqvist K, Kacprzyk L, Chalupka A, et al. (2008) Histidine-rich glycoprotein protects from systemic *Candida* infection. PLoS Pathog 4: e1000116.
38. Pollock J S, Forstermann U, Mitchell J A, Warner T D, Schmidt H H, et al. (1991) Purification and characterization of particulate endothelium-derived relaxing factor 45 synthase from cultured and native bovine aortic endothelial cells. Proc Natl Acad Sci USA 88: 10480-10484.
39. Wiegand I, Hilpert K, Hancock R E (2008) Agar and broth dilution methods to determine the minimal inhibitory concentration (MIC) of antimicrobial substances. Nat Protoc 3: 163-175.
40. Pasupuleti M, Walse B, Svensson B, Malmsten M, Schmidtchen A (2008) Rational design of antimicrobial C3a analogues with enhanced effects against Staphylococci using an integrated structure and function-based approach. Biochemistry 47: 9057-9070.

Example B

Thrombin-derived C-terminal Peptides have Therapeutic Potential in Endotoxin Mediated Shock and *P. aeruginosa* Sepsis Results The anti-inflammatory effect of GKY25 and its truncated form HVF18 was first studied in a macrophage model. As seen in FIG. 16, GKY25 completely eliminated LPS-induced NO-responses already at 1-2 µM, while the shorter fragment HVF18 required much higher doses for complete inhibition of LPS-mediated signalling. Similarly, GKY25, but not HVF18, reduced cytokines at 10 µM. Worth noticing here is also a significant up-regulation of IL-10. after treatment with HVF18 (FIG. 16). Next, effects of GKY25 and HVF18 on coagulation were investigated. From measurements of the activated partial thromboplastin time (aPTT) both peptides were found to impair the intrinsic pathway of coagulation in normal human plasma. Other parts of the coagulation system, as judged by the prothrombin time (PT; monitoring the extrinsic pathway of coagulation), and the thrombin clotting time (TCT; measuring thrombin induced fibrin network formation), were not significantly affected (FIG. 17A). Next, blood was subjected to LPS and clotting time was evaluated. As seen, treatment with GKY25, and to a lesser extent HVF18 increased the clotting time (FIG. 17B) It is notable, that GKY25 almost restored the clotting time to normal values at concentrations similar to the physiological concentration of the holoprotein, thrombin (1.5 µM) (FIG. 17C). In order to study the effect of expression of tissue factor, human monocytes were stimulated with LPS, and TF-mediate coagulation recorded. As seen, particularly GKY25 was significantly prolonged coagulation to normal levels, while HVF18 was less potent also here.

Figure 18:
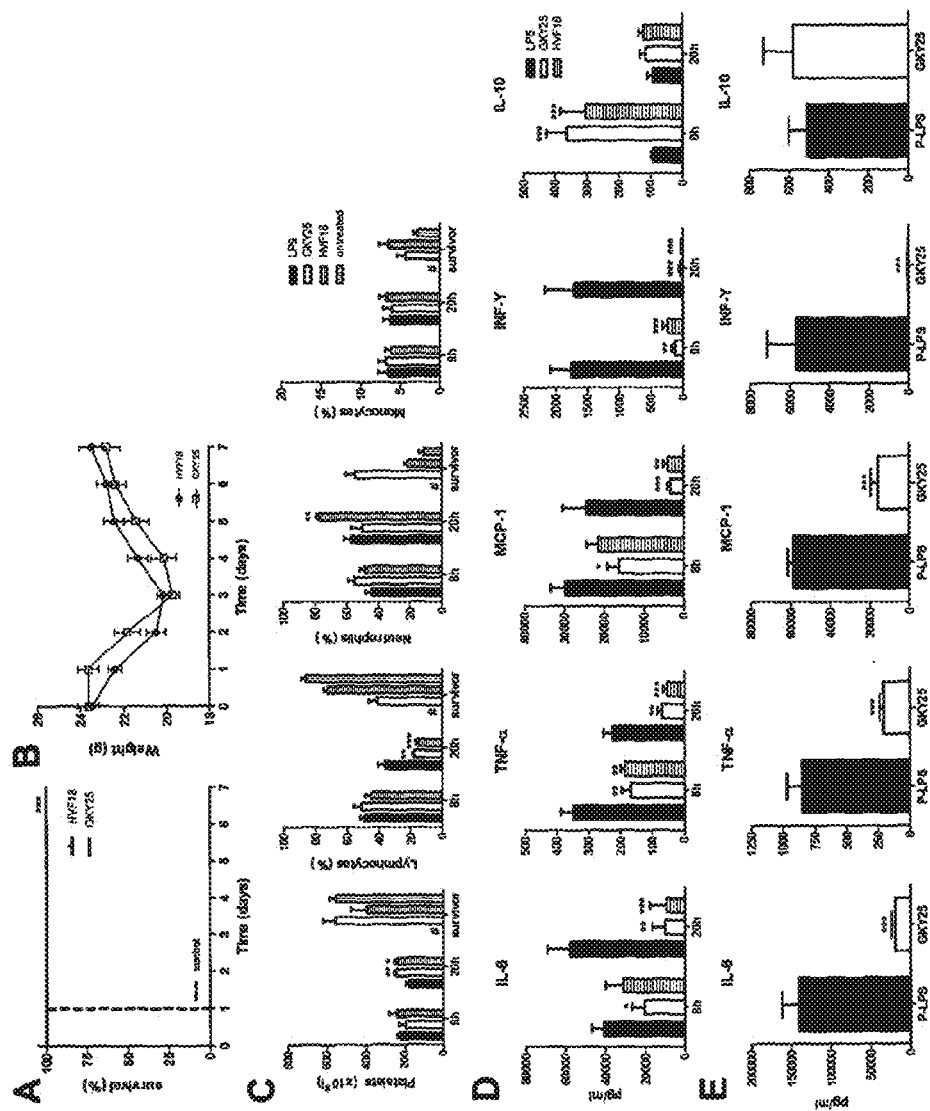

In a mouse model of LPS-induced shock (FIG. 18), both GKY25 and HVF18 displayed a dramatic improvement on survival (FIG. 18A). The treated animals also showed full recovery of weight (FIG. 18B). Analyses of platelet counts after 8 and 20 h showed that the two peptides significantly increased platelets, indicative of reduced consumption in this particular LPS-model (FIG. 18C). The levels were completely normalized in the survivors. Analyses of cytokines 8 and 20 h after LPS injection showed significant reductions of proinflammatory IL-6, IFN-γ, TNF-α, and MCP-1, whereas an increase in IL-10 was observed after 8 h for both peptides (FIG. 18D). Similar reductions after treatment with GKY25 were seen in a similar chock model using *P. aeruginosa* LPS, suggesting limited strain variability between Gram-negative bacteria in regards to the effects of GKY25 and HVF18. WFF25, a control peptide of the same composition as GKY25, but with the amino acids sorted after hydrophobicity in order to eliminate sequence dependence, as well as the ability to form an ordered helix on interaction with LPS, with retained antimicrobial effects in vitro, did not show anti-inflammatory effects in vitro and in vivo, and did not rescue the mice from LPS-induced sepsis (FIG. 19). Correspondingly, while SEM analyses of the lungs from LPS-treated animals demonstrated pulmonary leakage of protein and red blood cells (FIG. 20), lungs of GKY25- and HVF18-treated animals, in contrast to those treated with WFF25, showed marked reductions of these LPS-induced effects. The results thus demonstrate a marked anti-inflammatory effect of particularly GKY25 in this animal model of LPS-shock. In order to further explore a potential therapeutic effect of the latter peptide in bacterial sepsis, a model employing *P. aeruginosa* was used. Initial studies a low infective dose (FIG. 21), showed that bacterial levels increased between 4-12 h in the organs analysed (spleen, kidney, and liver). Treatment with the peptide only marginally reduced bacterial levels, although the reductions were statistically significant for liver and spleen. It was notable however, that a concomitant reduction of cytokine levels was observed, particularly after 12 h (FIG. 218), and noted for proinflammatory IL-6, IFN-γ, TNF-α, and MCP-1, whereas an increase in IL-10 was observed after 8 h (not significant), a decrease was observed after 12 h (FIG. 21B). Similar findings were demonstrated using a higher infective dose of *P. aeruginosa*. Notably, a marked increase in cytokines was observed in this experiment, reflecting the higher levels of cfu (see FIG. 22). Based on these initial results, the effects of one vs. two administrations of GKY25 was evaluated in the *P. aeruginosa* sepsis model. As seen in FIG. 22A, repeated treatment yielded a moderate reduction of cfu numbers in the organs evaluated. This was paralleled by a concomitant and highly significant reduction of cytokines in blood (FIG. 22B). Treatment with one dose of GKY25 did not increase survival. However, a two-dose regime as above, resulted in a significant delay of septic symptoms as well as delayed mortality, and eventually also increase survival (FIG. 22).

Discussion

Taken together, the results demonstrate that GKY25 has dual effects on both TLR-mediated pathways and coagulation. Apart from demonstrating these effects in vitro, the mice models indicate the ability of GKY25 and HVF18 to cure animals with acute septic shock in a seemingly strain-independent manner, including a promising reduction of leakage and inflammation in the lungs. Substantial reduction of a range of key cytokines, as well as promotion of antiinflammatory IL10 seems to play an important role, together with peptide effects on coagulation. In line with previous findings, the shorter HVF18 is less potent than GKY28, suggesting a length-dependent interaction with TRL receptors, potentially dependent on length-dependent helix formation by these peptides. The latter is compatible with the strongly reduced effects of observed for WFF25 (a scrambled version of GKY25) compared to GKY25, since the former peptide is unable to form a helix on LPS interaction as done for HVF18 and even more so by GKY25. Additionally, GKY25 ameliorates P. aeruginosa sepsis, with a pronounced reduction in proinflammatory cytokine levels, as well as displaying anti-coagulative effects. Strikingly, repeated administrations of GKY25 in the P. aeruginosa sepsis model leads to further reduced cytokine levels. Partly, the advantageous effect of the repeated peptide administration is due to the remainder of relatively large number of bacteria due to insufficient direct antimicrobial effect of the peptides. However, both proteolytic degradation of GKY25 due to bacterial proteases (ref) and scavenging through binding of the positively charged GKY25 to negatively charged serum proteins and tissue components are likely to contribute to an effective consumption of free and intact GKY25, thus leading to a transient pharmacokinetic potency. Given this, the advantageous effect of the repeated peptide administration is not unexpected.

For both LPS and P. aeruginosa sepsis, the regulation of excessive cytokine levels is regarded as a relevant target in sepsis, and it is notable that the peptides significantly dampen the cytokine response, preferably on pro-inflammatory TNF-α and IL-6. In addition to these immunomodulating effects, GKY25 also exerts anticoagulative effects. Disseminated intravascular coagulation is a frequent complication of sepsis. Coagulation activation, inhibition of fibrinolysis, and consumption of coagulation inhibitors lead to a procoagulant state resulting in inadequate fibrin removal and fibrin deposition in the microvasculature. As a consequence, microvascular thrombosis contributes to promotion of organ dysfunction. Furthermore, excessive contact activation leads release of proinflammatory peptide bradykinin and initiates the intrinsic pathway of coagulation. A systemic activation of the coagulation cascade, including the contact system lead to pathologically high levels of bradykinin, and a subsequent induction of inflammatory reactions. These conditions contribute to serious complications such as hypotension and vascular leakage. Therefore, peptides blocking these pathways are potentially interesting in sepsis. This is particularly relevant, since contact activation is known to be a crucial early event during the initiation of sepsis. Finally, it should be noted that also repeated peptide administration resulted only in a relatively modest reduction in bacterial cfu, whereas potent antiinflammatory effects were observed. While the latter was sufficient to delay and reduce mortality, it can be expected that a combination treatment of GKY25 and an antibiotic may be interesting for further improved therapeutic outcome for bacterial sepsis. Through the combination of a more pronounced reduction in bacterial cfu from the antibiotic, and the antiinflammatory protection from GKY25, a clear therapeutic potential is offered.

Methods

Peptides

The thrombin-derived peptides GKY25 (GKYGFYTHV-FRLKKWIQKVIDQFGE [SEQ ID NO: 2]) and HVF18 (HVFRLKKWIQKVIDQFGE [SEQ ID NO: 5]), as well as the control peptide WFF25 (WFFFYYLIIGGGV-VTHQQRKKKKDE [SEQ ID NO: 27]), were synthesized by Biopeptide Co., San Diego, USA. The purity (>95%) of these peptides was confirmed by mass spectral analysis (MALDI-ToF Voyager).

Cells

The mouse macrophage cell line RAW 264.7 was obtained from the American Type Culture Collection (ATCC, Rockville, Md.). RAW 264.7 cells were cultured in Dulbecco's modified Eagle medium (DMEM) supplemented with 10% heat-inactivated fetal bovine serum (Invitrogen) and 1% Antibiotic-Antimycotic (Sigma-Aldrich). Human peripheral blood monocytes (hPBMNC) were isolated from fresh heparinized or citrated blood from healthy volunteers by using density gradient centrifugation. PBMNC were collected in RPMI 1640 (PAA-Laboratories).

LPS Models In vitro

Nitrite assay. $3.5 \times 10^5$ RAW 264.7 cells were seeded in 96-well tissue culture plates (Nunc no. 167008) in phenol red-free DMEM (Gibco) supplemented with 10% FBS containing 1% Anti-Anti (Invitrogen). Following 20 hours of incubation to permit adherence, cells were washed and stimulated with 10 ng/ml E. coli (0111:B4) or P. aeruginosa LPS (Sigma-Aldrich), with and without the peptides GKY25, HVF18, or WFF25 of various doses. The level of NO in culture supernatants was determined after a period of 20 hours using the Griess reaction (27)ref. Briefly, Nitrite, a stable product of NO degradation, was measured by mixing 50 μl of culture supernatants with the same volume of Griess reagent (Sigma, G4410), and reading absorbance at 550 nm after 15 min. Phenol-red free DMEM with FBS and antibiotics were used as a blank. A standard curve was prepared using sodium nitrite at 0-80 μM in ddH$_2$O.

TNF-α assay. hPBMNC were cultured for 7-10 days in phenol red-free RPMI 1640 supplemented with 10% heat-inactivated human plasma (donor corresponding) and 1% Anti-Anti (Invitrogen) followed by 6 hours stimulation with 10 ng/ml E. coli (0111:B4) LPS, with and without the peptides GKY25 or HVF18. Cell supernatants were collected and stored at −20° C. Whole human lepirudin-treated blood (500 μl) was incubated with 10 ng/ml E. coli (0111:14) LPS, with and without the peptides GKY25 or HVF18 for 6 h on rotation at 37° C. Plasma was obtained by centrifuging at 400 g, 10 min and stored at −20° C. The TNF-α level was measured using a human TNF-Elisa Kit (Invitrogen).

LPS Model In vivo

Male C57BL/6 mice (8 weeks, 21+/−5 g), were injected intraperitoneally with 18 mg E. coli 0111:B4 LPS or 36 mg P. aeruginosa LPS (Sigma) per kg of body weight. Thirty minutes after LPS injection, 0.2 or 0.5 mg GKY25, HVF18, or WFF25 (10 mM Tris, pH 7.4) or buffer alone was injected intraperitoneally into the mice. Survival and status was followed during seven days. For SEM and histochemistry, mice were sacrificed 20 h after LPS challenge, and lungs, liver, kidney, and spleen were removed and fixed. For determination of cytokine levels in mouse plasma, animals were sacrificed 8 h and 20 h after LPS injection. The blood was collected immediately by cardiac puncture. These experiments were approved by the Laboratory Animal Ethics Committee of Malmö/Lund.

Animal Infection Model

Animals were housed under standard conditions of light and temperature and had free access to standard laboratory chow and water. P. aeruginosa 15159 bacteria were grown to logarithmic phase (OD$_{620}$~0.5), harvested, washed in PBS, diluted in the same buffer to $2 \times 10^8$ cfu/ml, and kept on ice until injection. Hundred microliter of the bacterial suspension was injected intraperitoneally (i.p.) into female b16 mice. 60 minutes after the bacterial injection, 0.5 mg GKY25 or buffer alone was injected sc into the mice. In order to study bacterial dissemination to target organs spleen, liver and kidney were harvested, placed on ice, homogenized, and colony-forming units determined. The P-value was determined using the Mann-Whitney U-test. Data from three independent experiments were pooled.

Clinical Parameters

Mouse blood (anti-coagulated with EDTA) was taken by cardiac puncture and analysed with the VetScan HM5 System (TRIOLAB). The number of white blood cells, percentages of lymphocytes, neutrophils, monocytes and platelets were determined.

Cytokine Assay

The cytokines IL-6, IL-10, MCP-1, INF-γ, and TNF-α were measured in cell culture supernatants from RAW264.7 cells and plasma from mice injected with LPS or *P. aeruginosa* (with or without peptide treatment) using the Cytometric bead array; Mouse Inflammation Kit (Becton Dickinson AB) according to the manufacturer's instructions. All plasma samples were stored at −20° C. before the analysis.

Clotting Assays

All clotting times were analyzed using a coagulometer (Amelung, Lemgo, Germany). The prothrombin time (PT) and the Thrombin clotting time (TCT) were measured as followed: Hundred microliter of fresh human citrate plasma together with indicated concentrations of GKY25 or HVF18 were pre-warmed for 60 sec at 37° C. before clot formation was initiated by adding 100 µl a clotting reagent. (PT-thromboplastin reagent (Trinity Biotech), TCT: Thrombin reagent (Technoclone)). To record the activated partial thromboplastin time (aPTT), 100 µl of a kaolin-containing solution (Technoclone) was add to the plasma-peptide mix and incubated for 200 sec before clot formation was initiated by adding 100 µl of 30 mM fresh $CaCl_2$ solution. Alternatively, $1 \times 10^6$ hPB-MNC/ml in RPMI 1640 were stimulated with 100 ng/ml *E. coli* (0111:B4) LPS with and without GKY25 or HVF18 overnight on rotation at 37° C. Cells were washed and resuspended in 100 µl PBS. Hundred microliter of fresh human citrate plasma were reconstituted with 100 µl of fresh 30 mM $CaCl_2$ solution and pre-warmed for 60 sec. The clot formation was started by adding the hPBMNC. The same procedure was used to determine clotting times for whole blood.

Flow Cytometry $1 \times 10^6$ hPBMNC/ml in RPMI 1640 were stimulated with 100 ng/ml *E. coli* (0111:84) LPS with and without GKY25 or HVF18 for 6 h on rotation at 37° C. Cells were washed once and resuspended in PBS followed by incubation with FITC-anti-TF AB (American Diagnostics) or FITC-IgG1 (BD Biosciences), PE-anti-CD14 or PE-IgG1 (BD Biosciences) for 30 min on ice. Samples were washed and analysed with a FACS Calibur flow cytometer (BD). Monocyted were identified by forward/sideward scatter and CD14 expression.

Histochemistry

Organs collected 20 h after LPS injection were immediately fixed in 4% paraformaldehyde before they were embedded in paraffin and sectioned. Sections were stained 10 min with Mayers Hematoxilin (Histolab AB) and 7 min with Eosin (Merck). Sectioning and staining was done at Histocenter, Gothenburg, Sweden.

Scanning Electron Microscopy

For scanning electron microscopy lungs were taken 20 h after LPS injection. Samples were fixed in 2.5% glutaraldehyde in 0.15 M sodium cacodylate buffer, pH 7.4, over night at room temperature. Specimens were washed with cacodylate buffer, and dehydrated with an ascending ethanol series from 50% (vv) to absolute ethanol. The specimens were then subjected to critical-point drying in carbon dioxide, with absolute ethanol as intermediate solvent, mounted, on aluminium holders, sputtered with 30 nm palladium/gold and examined in a JEOL JSM-350 scanning electron microscope Statistics Values are shown as mean±SD. To compare two experimental groups the Man Whitney test or students t-test was used. P-values <0, 05 were considered as indicating a significant difference.

Example C

Structure-activity Studies of Host Defense Peptides of Human Thrombin

Summary

Peptides of the C-terminal region of human thrombin are released upon proteolysis, and identified in vivo. In this study we wanted to investigate minimal determinants, as well as structural features, governing the antimicrobial and immunomodulating activity of this region. Sequential amino acid deletions of the peptide GKYGFYTHVFR-LKKWIQKVIDQFGE (GKY25) [SEQ ID NO: 2], as well as substitutions at strategic and structurally relevant positions were followed by analyses of antimicrobial activity against the Gram-negative *Escherichia coli* and *Pseudomonas aeruginosa*, the Gram-positive *Staphylococcus aureus* as well as the fungus *Candida albicans*. Furthermore, peptide effects on lipopolysaccharide-, lipoteichoic acid-, or zymosan-induced macrophage activation were studied. The thrombin-derived peptides displayed length- and sequence-dependent antimicrobial as well as immunomodulating effects. A peptide length of at least 20 amino acids was required for effective anti-inflammatory effects in macrophage models, as well as optimal antimicrobial activity as judged by MIC assays. However, shorter (>12 amino acids) variants also displayed significant antimicrobial effects. A central K13 residue was important for optimal antimicrobial activity. Finally, one peptide variant, GKYGFYTHVFR-LKKWIQKVI (GKY20) [SEQ ID NO: 3] exhibiting improved selectivity, i.e., low toxicity and a preserved antimicrobial as well as anti-inflammatory effect, showed efficiency in mouse models of LPS-shock and *P. aeruginosa* sepsis. The work defines structure activity relationships of C-terminal host defense peptides of thrombin, and delineates a strategy for selecting peptide epitopes of therapeutic interest.

Introduction

The extensive use of classical antibiotics has led to the emergence of increasing resistance among bacteria [1]. In this perspective, cationic antimicrobial peptides (AMPs) are interesting since they provide a rapid and broad-spectrum response towards both Gram-negative and Gram-positive bacteria, as well as fungi [2,3,4,5,6,7,8], and show little risk of resistance induction [6]. Although AMPs may influence bacteria in a multitude of ways [5], bacterial wall rupture seems to play a key role in the bactericidal action of most AMPs. During recent years it has become increasingly evident that many AMPs, including defensins and cathelicidins, are multifunctional, also mediating various immunomodulatory roles and angiogenesis [9,10,11], thus motivating the recent and broader definition host defense peptides (HDP) for these members of the innate immune system. The family of HDPs has recently been shown to encompass a diverse family of peptides, including proinflammatory and chemotactic chemokines [12], neuropeptides [5], peptide hormones [13, 14], growth factors [15], the anaphylatoxin peptide C3a [16, 17], and kininogen-derived peptides [18,19,20]. We have previously shown that C-terminal peptides of thrombin constitute a novel class of host defense peptides, released upon proteolysis of thrombin in vitro, and detected in human wounds in vivo. Thus, under physiological conditions, these peptides exert antimicrobial effects against Gram-positive and Gram-negative bacteria, mediated by membrane lysis, as well as immunomodulatory functions, by inhibiting macrophage responses to bacterial lipopolysaccharide [21]. In mice, they are protective against *P. aeruginosa* sepsis, as well as lipopolysaccharide-induced shock. Moreover, the thrombin-derived C-terminal peptides exhibit helical structures upon binding to lipopolysaccharide, and permeabilize liposomes, features typical of "classical" helical antimicrobial peptides. These findings provide a novel link between the coagulation system and host-defense peptides, two fundamental biological systems activated in response to injury and microbial invasion. Although peptides were identified with these advantageous properties, however, the previous work provided no insight whether these peptides, or shorter sequences in these, are responsible for the effects observed. In the present study, we therefore set out to investigate minimal determinants, as well as structural features, governing the antimicrobial and immunomodulating activity of this peptide region.

Material and Methods

Peptides

Peptides were from Sigma-Genosys, generated by a peptide synthesis platform (PEPscreen®, Custom Peptide Libraries, Sigma Genosys). Prior to biological testing the PEPscreen peptides were diluted in dH$_2$O (5 mM stock), and stored at −20° C. This stock solution was used for the subsequent experiments. Selected peptides were synthesized by Biopeptide, San Diego, US. The purity (>95%) and molecular weight of these peptides was confirmed by both suppliers by mass spectral analysis (MALDI.TOF Voyager). LL37 was from Innovagen AB, Lund, Sweden (purity >95%).

Microorganisms

*Escherichia coli* ATCC 25922, *Pseudomonas aeruginosa* ATCC 27853 *Staphylococcus aureus* ATCC 29213, and *Candida albicans* ATCC 90028 were obtained from the Department of Clinical Bacteriology at Lund University Hospital. Additional *S. aureus* clinical isolates were obtained from patients with skin infections.

Radial Diffusion Assay

Essentially as described earlier [22,23] bacteria were grown to mid-logarithmic phase in 10 ml of full-strength (3% w/v) trypticase soy broth (TSB) (Becton-Dickinson, Cockeysville, Md.). The microorganisms were then washed once with 10 mM Tris, pH 7.4. Subsequently, 4×10 bacterial colony forming units were added to 15 ml of the underlay agarose gel, consisting of 0.03% (w/v) TSB, 1% (w/v) low electroendosmosis type (EEO) agarose (Sigma, St Louis Mo.) and 0.02% (v/v) Tween 20 (Sigma) with or without 0.15M NaCl. The underlay was poured into a Ø 144 mm petri dish. After agarose solidification, 4 mm-diameter wells were punched and 6 µl of test sample was added to each well. Plates were incubated at 37° C. for 3 hours to allow diffusion of the peptides. The underlay gel was then covered with 15 ml of molten overlay (6% TSB and 1% Low-EEO agarose in distilled H$_2$O). Antimicrobial activity of a peptide is visualized as a zone of clearing around each well after 18-24 hours of incubation at 37° C.

Viable-count Analysis

*E. coli* ATCC 25922 bacteria were grown to mid-logarithmic phase in Todd-Hewitt (TH) medium (Becton and Dickinson, Maryland, USA). The microorganisms were then washed and diluted in 10 mM Tris, pH 7.4 containing 5 mM glucose. Following this, bacteria (50 µl; 2×10$^8$ cfu/ml) were incubated, at 37° C. for 2 hours, with the peptides GKY25, GKY20, YTH20, or FYT20 (at 0.03, 0.06, 0.3, 0.6, 3, 6, 30, 60 µM) in 10 mM Tris, 0.15 M NaCl, with or without 20% human citrate-plasma. In the experiments using 50% whole blood, *S. aureus* ATCC 29213 and *P. aeruginosa* ATCC 27853 bacteria (50 µl; 2×10$^8$ cfu/ml) were incubated at 37° C. for 1 hour in the presence of peptide at 60 (for *P. aeruginosa*) and 120 µM (*P. aeruginosa* and *S. aureus*). To quantify the bactericidal activity, serial dilutions of the incubation mixtures were plated on TH agar, followed by incubation at 37° C. overnight and the number of colony-forming units was determined. 100% survival was defined as total survival of bacteria in the same buffer and under the same condition in the absence of peptide. Significance was determined using the statistical software SigmaStat (SPSS Inc., Chicago, Ill., USA).

Hemolysis Assay

For experiments in 50% blood, citrate-blood was diluted (1:1) with PBS. The cells were then incubated with end-over-end rotation for 1 h at 37° C. in the presence of peptides (60 or 120 µM). 2% Triton X-100 (Sigma-Aldrich, St. Louis, USA) served as positive control. The samples were then centrifuged at 800 g for 10 min. The absorbance of hemoglobin release was measured at 540 nm and is, expressed as % of TritonX-100 induced hemolysis. In the experiments with blood infected by bacteria, citrate-blood was diluted (1:1) with PBS. The cells were then incubated with end-over-end rotation for 1 h at 37° C. in the presence of peptides (60 and 120 µM) and *S. aureus* (2×10$^8$ cfu/ml) or *P. aeruginosa* (2×10$^8$ cfu/ml) bacteria. For evaluation of hemolysis, samples were then processed as above.

Minimal Inhibitory Concentration Assay (MIC)

MIC analysis, defining the lowest concentration of the AMP that prevents microbial growth, was carried out by a microtiter broth dilution method [24]. For determination of MIC, peptides were dissolved in 10 mM Tris, pH 7.4 at a concentration 5 times higher than the required range by serial dilutions from a stock solution. Twenty µl of each concentration was added to each corresponding well of a 96-well microtiter plate (polypropylene, Costar Corp., Cambridge, Mass.). Bacteria grown over night in 3% TSB was rinsed with Tris, pH 7.4, and diluted in refined LB medium to get a concentration of ~1×10$^5$ CFU/ml. One-hundred µl of bacterial solution in the refined LB medium was added to each well containing the test peptides. The plate was incubated at 37° C. overnight. The MIC was taken as the concentration at which no visible bacterial growth was observed.

LPS Effects on Macrophages In vitro 3.5×10$^5$ cells were seeded in 96-well tissue culture plates (Nunc, 167008) in phenol red-free DMEM (Gibco) supplemented with 10% FBS and antibiotics. Following 6 hours of incubation to permit adherence, cells were stimulated with 10 ng/mL *E. coli* LPS (0111:B4) or 10 µg/ml *S. aureus* LTA (L2515) or 25 µg/ml *Saccharomyces cerevisiae* Zymosan A(Z4250) (Sigma), with and without peptide of various doses. The levels of NO in culture supernatants were determined after 24 hours from stimulation using the Griess reaction [25]. Briefly, nitrite, a stable product of NO degradation, was measured by mixing 50 µl of culture supernatants with the same volume of Griess reagent (Sigma, G4410) and reading absorbance at 550 nm after 15 min. Phenol-red free DMEM with FBS and antibiotics were used as a blank. A standard curve was prepared using 0-80 µM sodium nitrite solutions in ddH20.

Lactate Dehydrogenase (LDH) Assay

HaCaT keratinocytes were grown in 96 well plates (3000 cells/well) in serum free keratinocyte medium (SFM) supplemented with bovine pituitary extract and recombinant EGF (BPE-rEGF) (Invitrogen, USA) to confluency. The medium was then removed, and 100 µl of the peptides investigated (at 60 µM and 120 µM, diluted in SFM/BPE-rEGF), was added in triplicates to different wells of the plate. The LDH based TOX-7 kit (Sigma-Aldrich, St Louis, USA) was used for quantification of LDH release from the cells. Results given represent mean values from triplicate measurements. Results are given as fractional LDH release compared to the positive control consisting of 1% Triton X-100 (yielding 100% LDH release).

MTT Assay

Sterile filtered MTT (3-(4,5-dimethylthiazolyl)-2,5-diphenyl-tetrazolium bromide; Sigma-Aldrich) solution (5 mg/ml in PBS) was stored protected from light at −20° C. until usage. HaCaT keratinocytes, 3000 cells/well, were seeded in 96 well plates and grown in serum free keratinocyte-SFM/BPE-rEGF medium to confluency. Peptides investigated were then added at 60 µM and 120 µM. After incubation over night, 20 µl of the MTT solution was added to each well and the plates incubated for 1 h in $CO_2$ at 37° C. The MTT containing medium was then removed by aspiration. The blue formazan product generated was dissolved by the addition of 100 µl of 100% DMSO per well. The plates were then gently swirled for 10 min at room temperature to dissolve the precipitate. The absorbance was monitored at 550 nm, and results given represent mean values from triplicate measurements.

Fluorescence Microscopy

For study of membrane permeabilization using the impermeant probe FITC, *E. coli* ATCC 25922 bacteria were grown to mid-logarithmic phase in TSB medium. The bacteria were washed and resuspended in either 10 mM Tris, pH 7.4, 10 mM glucose, 0.15 M NaCL, to yield a suspension of $1 \times 10^7$ cfu/ml. 100 µl of the bacterial suspension was incubated with 30 µM of the respective peptides at 30° C. for 30 min. Microorganisms were then immobilized on poly (L-lysine)-coated glass slides by incubation for 45 min at 30° C., followed by addition onto the slides of 200 µl of FITC (6 µg/ml) in the appropriate buffers and incubated for 30 min at 30° C. The slides were washed and bacteria were fixed by incubation, first on ice for 15 min, then room temperature for 45 min in 4% paraformaldehyde. The glass slides were subsequently mounted on slides using Prolong Gold antifade reagent mounting medium (Invitrogen). For fluorescence analysis, bacteria were visualized using a Nikon Eclipse TE300 (Nikon, Melville, N.Y.) inverted fluorescence microscope equipped with a Hamamatsu C4742-95 cooled CCD camera (Hamamatsu, Bridgewater, M J) and a Plan Apochromat ×100 objective (Olympus, Orangeburg, N.Y.). Differential interference contrast (Nomarski) imaging was used for visualization of the microbes themselves.

Liposome Preparation and Leakage Assay

Anionic DOPE/DOPG (75/25 mol/mol) liposomes were investigated regarding peptide-induced membrane disruption. DOPG (1,2-dioleoyl-sn-Glycero-3-phosphoglycerol, monosodium salt), and DOPE (1,2-dioleoyl-sn-Glycero-3-phoshoetanolamine) were from Avanti Polar Lipids (Alabaster, USA) and of >99% purity, while cholesterol (of >99% purity), was from Sigma-Aldrich (St. Louis, USA). The lipid mixtures were dissolved in chloroform, after which solvent was removed by evaporation under vacuum overnight. Subsequently, 10 mM Tris buffer, pH 7.4, was added together with 0.1 M carboxyfluorescein (CF) (Sigma, St. Louis, USA). After hydration, the lipid mixture was subjected to eight freeze-thaw cycles, consisting of freezing in liquid nitrogen and heating to 60° C. Unilamellar liposomes of about Ø140 nm were generated by multiple extrusions through polycarbonate filters (pore size 100 nm) mounted in a LipoFast miniextruder (Avestin, Ottawa, Canada) at 22° C. Untrapped CF was removed by two subsequent gel filtrations (Sephadex G-50, GE Healthcare, Uppsala, Sweden) at 22° C., with Tris buffer as eluent. CF release from the liposomes was determined by monitoring the emitted fluorescence at 520 nm from a liposome dispersion (10 mM lipid in 10 mM Tris, pH 7.4). An absolute leakage scale was obtained by disrupting the liposomes at the end of each experiment through addition of 0.8 mM Triton X-100 (Sigma-Aldrich, St. Louis, USA). A SPEX-fluorolog 1650 0.22-m double spectrometer (SPEX Industries, Edison, USA) was used for the liposome leakage assay. Measurements were performed in triplicate at 37° C.

CD-spectroscopy

The CD spectra of the peptides in solution were measured on a Jasco J-810 Spectropolarimeter (Jasco, U.K.). The measurements were performed at 37° C. in a 10 mm quartz cuvet under stirring and the peptide concentration was 10 µM. The effect on peptide secondary structure of liposomes at a lipid concentration of 100 µM was monitored in the range 200-250 nm. The only peptide conformations observed under the conditions investigated were α-helix and random coil. The fraction of the peptide in α-helical conformation was calculated from the CD signal at 225 nm. 100% α-helix and 100% random coil references were obtained from 0.133 mM (monomer concentration) poly-L-lysine in 0.1 M NaOH and 0.1 M HCl, respectively [26,27] For determination of effects of lipopolysaccharide on peptide structure, the peptide secondary structure was monitored at a peptide concentration of 10 µM, both in Tris buffer and in the presence of *E. coli* lipopolysaccharide (0.02 wt %) (*Escherichia coli* 0111:B4, highly purified, less than 1% protein/RNA, Sigma, UK). To account for instrumental differences between measurements the background value (detected at 250 nm, where no peptide signal is present) was subtracted. Signals from the bulk solution were also corrected for. Measurements were performed in triplicate at 37° C.

LPS Model In vivo

Male C57BL/6 mice (8-10 weeks, 22+/−5 g), were injected intraperitoneally with 18 mg *E. coli* 0111:B4 LPS (Sigma) per kg of body weight. Thirty minutes after LPS injection, 0.5 mg GKY20 or buffer alone was injected intraperitoneally into the mice. Survival and status was followed during seven days. For blood collection and histochemistry, mice were sacrificed 20 h after LPS challenge, and lungs were removed and fixed. These experiments were approved by the Laboratory Animal Ethics Committee of Malmö/Lund.

Cytokine Assay

The cytokines IL-6, IL-10, MCP-1, INF-γ, and TNF-α were measured in plasma from mice subjected to LPS (with or without peptide treatment) using the Cytometric bead array; mouse inflammation kit (Becton Dickinson AB) according to the manufacturer's instructions.

Animal Infection Model

Animals were housed under standard conditions of light and temperature and had free access to standard laboratory chow and water. *P. aeruginosa* 15159 bacteria were grown to logarithmic phase ($OD_{620}$~0.5), harvested, washed in PBS, diluted in the same buffer to $2 \times 10^8$ cfu/ml, and kept on ice until injection. Hundred microliter of the bacterial suspension was injected intraperitoneally (i.p.) into female b16 mice. 30 minutes after the bacterial injection, 0.5 mg GKY20 or buffer alone was injected i.p. into the mice. In order to study bacterial dissemination to target organs spleen, liver and kidney were harvested, placed on ice, homogenized, and colony-forming units determined. The P-value was determined using the Mann-Whitney U-test. Data from three independent experiments were pooled. For SEM, specimens were washed with cacodylate buffer, and dehydrated with an ascending ethanol series from 50% (v/v) to absolute ethanol (10 min per step). The specimens were then subjected to critical-point drying in carbon dioxide, with absolute ethanol as intermediate solvent, mounted on aluminium holders, sputtered with nm palladium/gold, and examined in a JEOL JSM-350 scanning electron microscope. For histological evaluation of lungs derived from the in vivo LPS-models in mice, tissues were embedded as above, sectioned and stained with hematoxylin and eosin by routine procedures (Histocenter, Gothenburg, Sweden).

Calculations

Relative hyrophobic moment (µHrel) was calculated using the web-based algorithm found at see worldwide web at bbc-m.univ.trieste.it/~tossi/HydroMCalc.html.

Results

Previous x-ray crystallographic studies of intact thrombin have shown that the C-terminal region (HVFRLKKWIQKVIDQFGE [SEQ ID NO: 5]) adopts an α-helical conformation in the thrombin molecule. As an isolated peptide, on the other hand, this region adopts a dynamic random coil conformation in aqueous solution [21]. Nevertheless, the peptide GKY25 has the ability to adopt a helical conformation in specific solvent environments, such as the presence of LPS [21]. It is notable that the peptide contains a helix stabilizing N-cap motif of the C-terminal helix. Furthermore, the side chain of H230 (H8 in KYG20) makes a hydrogen bond to the backbone amide three residues downstream (R233 or R10). Of relevance for this peptide region is also the observation that a spacing of i, i+3 or i, i+4 between hydrophobic residues such as L, I, and W is known to stabilise helices with the latter spacing giving the strongest interaction [28]. In order to evaluate minimal antimicrobial epitopes of GKY25, as well as determine the potential hemolytic effects of these shorter fragments, peptides sequentially truncated from either the C- or N-terminus were analyzed in RDA against *E. coli* as well as tested for hemolysis using human erythrocytes. As shown in FIG. 24, bactericidal activities were retained for shorter fragments, as particularly noted for the C- and the simultaneously N- and C-terminally truncated peptides. In general, the presence of salt was slightly inhibitory on peptide activity. It is notable that the short N and C-terminally truncated 12-mer peptide, VFRLKKWIQKVI [SEQ ID NO: 28], containing the central "core", retained good bactericidal potency at high salt conditions (FIG. 24A). In general, peptides having lengths of above 18-20 amino acids displayed hemolytic effects at the concentration tested (60 µM) (FIG. 24 A). The antibacterial analyses were extended to the Gram-negative *Pseudomonas aeruginosa*, the Gram-positive *Staphylococcus aureus*, and the fungus *Candida albicans* (FIG. 24 B). Apart from showing the broad spectrum activity of GKY25 the results illustrate that GKY-derived peptides of shorter length (down to 8-10 amino acid residues) retain their activity at the low salt conditions used. Hence, taken together, the results illustrate that hemolytic and antibacterial effects partly overlap, although there is a tendency that shorter peptide fragments of 15-20 amino acids retain good antimicrobial activity. In order to further delineate some structural prerequisites determining activity, we synthesized 16-mer peptides based on the internal sequence THVFRLKKWIQKVIDQ [SEQ ID NO: 29], ($z_{nef}$=+4), encompassing the critical N and C-cap motifs, but having the cationic R and K-residues sequentially replaced by S. It is notable that among the peptides having one K replaced ($Z_{nef}$=3), the central K residue N-terminal of W appeared to be the most critical for antimicrobial activity, particularly against *S. aureus*.

Introducing one more change in this peptide, again in the central part and C-terminal of Q almost completely abrogated the activity of the peptide (FIG. 25). Thus, the results indicate that the central two K residues adjacent to the evolutionary conserved WI sequence are particularly important for determining the antimicrobial activity of this region of the peptide.

Given the potent anti-endotoxic effects of GKY25, we next studied the length dependence of the anti-inflammatory effect in a macrophage model. As seen in FIG. 26, the results showed that a peptide length of minimum 19-20 amino acids is required for complete inhibition of LPS-mediated signalling. A similar dependence was observed for LTA as well as zymosan mediated NO-induction. The 3D-graphs (FIG. 27) illustrate the relation between the observed antimicrobial activity, ability to block LPS-responses, and the product between (µHrel) and net charge, the latter parameter previously found to correspond well to predicted antimicrobial activity [29]. As seen, the graphs illustrate the partial overlap between antimicrobial and anti-endotoxic activity, but also that given a product value of >1 (µHrel×$z_{net}$=3), only the peptides of length 19-20 amino acids are able to block LPS-effects on macrophages. Taken together, the above results indicate that successive truncations of GKY25 may yield shorter peptides having preserved antimicrobial and immunomodulatory properties.

Next, we analyzed selected peptides corresponding to three major groups, i.e., peptides of 20 amino acids showing "dual" effects (exerting both antimicrobial activity in high salt and anti-inflammatory activity), those only yielding antimicrobial effects in high salt (of 16 amino acids), and those only showing activity in low salt buffers. MIC assays using various *E. coli* and *S. aureus* strains showed that only the 20-mer peptides, and particularly the C-terminally truncated GKYG-FYTHVFRLKKWI (GKY20) [SEQ ID NO: 3], and the N- and C-terminally truncated FYTHVFRLKKWIQKVIDQFG (FYT20) [SEQ ID NO: 7] presented low MICs comparable to the parent GKY25, as well as the benchmark peptide LL-37 (FIG. 28A). It was also noted that the pure FYT20 peptide displayed some turbidity when dissolved at 5 mM, likely illustrating the high hydrophobicity and amphipaticity of this selected peptide region. In order to further explore the effects of these peptides in relevant physiological environments, viable count assays in 0.15 M NaCl and in presence of 20% human plasma were preformed (FIG. 28B). Whereas GKY20 showed similar antimicrobial activities in both environments, the N- and C-terminally truncated FYT20 as well as N-terminally truncated YTH20 were significantly inhibited, particularly in human plasma (FIG. 28B). Anti-endotoxin activity was probed for the truncated variants and compared with activity of the full-length GKY25. In correspondence with the initial screening results, the 20-mer peptides showed anti-inflammatory activities at or below 10 µM, in contrast to the shorter 16 and 12-mer variants. Interestingly, GKY16 still retained some activity at 50 µM (FIG. 29A). At 10 µM, the 20-mer peptide variants also inhibited LTA- and zymosan-induced NO-release from macrophages (FIG. 29B).

The 20-mer peptides all showed less hemolysis than the original GKY25 peptide, as well as LL-37 (FIG. 30A), however, it was noted that the dose of GKY25, required for permeabilization of erythrocytes significantly exceeded the MIC values (FIG. 28A), as well as the concentration required for efficient bacterial killing in the viable count assays (FIG. 28B). Likewise, the 20-mer variants affected viability to a lesser extent than GKY25 as well as LL-37, although the LDH-release was similar. In the presence of serum, on the other hand, the 20-mers displayed no detectable permeabilization with either LDH release or MTT assay. It was noted that both GKY25 and LL-37 showed some permeabilizing activity also in serum at 60 µM (FIG. 30B). Analogously, permeabilization of human skin fibroblasts by the 20-mer peptides was largely absent at 60 µM, in contrast to the findings obtained with GKY25 as well as LL-37 (FIG. 30C). In order to simultaneously explore hemolytic (FIG. 31A) as well as antimicrobial effects (FIG. 31B), of importance for subsequent in vivo studies, the two peptides GKY25 and GKY20 were added to human blood infected by S. aureus or P. aeruginosa. It was observed that the peptides, and particularly GKY20, displayed a significant selectivity, demonstrating almost complete eradication of P. aeruginosa and S. aureus, with little (~5% or less) accompanying hemolysis, at a peptide dose of 120 µM.

Taken together, the combination of hemolysis results and permeabilization studies on HaCat keratinocytes as well as human fibroblasts indicate that the truncated peptides, and particularly GKY20 show reduced toxicity at doses above those needed for antimicrobial as well as anti-inflammatory effects.

FIG. 32A shows that like GKY25, the 20-mer variants permeabilized E. coli cells, as visualized with the impermeant probe FITC. In order to obtain further structural and mechanistic information, we studied GKY25 (GKYGFYTHVFR-LKKWIQKVIDQFGE [SEQ ID NO: 2]), GKY20 (bold in previous sequence), as well as the epitope VFRLKKWIQKVI [SEQ ID NO: 28](VFR12, in italics), derived from an helical segment in GKY25, and previously shown to retain significant antimicrobial effects when compared with GKY20. As demonstrated in FIG. 32B, the peptides showed mostly a random coil conformation i buffer. However, LPS induced a conformational change in all the three peptide variants. In contrast, as seen in the CD-spectrum (FIG. 32B), and depicted in FIG. 32C, anionic liposomes significantly affected helix content only for GKY25. Moreover, GKY25 and GKY20 showed similar membrane disruptive effects on liposomes, and the activity of was significantly higher when compared with VFR12, likely reflecting their increased hydrophobicity and helix-inducing capability in a membrane environment (FIG. 31D).

Taken together, the above studies demonstrated the possibility of maintaining desired antimicrobial and anti-inflammatory effects, while reducing peptide length and attenuating peptide toxicity. The peptide GKY20, meeting the following prerequisites; little inhibition in plasma, reduced toxicity, as well as maintained MIC values and antiinflammatory effects, was selected in order to further investigate the potential therapeutic effectiveness in vivo. We therefore injected this peptide into mice infected with P. aeruginosa. Compared to the controls, treatment with GKY20 yielded significantly lower bacterial numbers in the spleen, liver, and kidney of the animals (FIG. 33A). In a mouse model of so LPS-induced shock, GKY20 displayed a dramatic improvement on survival (FIG. 33B, left panel). The treated animals also showed recovery of weight (FIG. 33B, right panel). Analyses of platelet counts after 12 h showed that GKY20 significantly increased platelets, indicative of reduced consumption in this particular LPS-model (FIG. 33B). Analyses of cytokines 20 hours after LPS injection showed significant reductions of proinflammatory IL-6, IFN-γ, TNF-α, and IL-12p70, whereas an increase in IL-10 was observed (FIG. 33C). Furthermore, a marked reduction of inflammation and vascular leakage in the lungs of the GKY20-treated animals was observed after histochemical evaluation of the lungs (FIG. 33D). Correspondingly, while SEM analyses of the lungs from LPS-treated animals demonstrated pulmonary leakage of protein and red blood cells (FIG. 33E), lungs of GKY20-treated animals showed marked reductions of these LPS-induced effects. The results thus demonstrate the therapeutic potential of GKY20, as well as illustrate the feasibility of the previous in vitro screening process generating an antimicrobial and anti-inflammatory molecule.

Discussion

In this study, we describe a general approach for determining minimal effective epitopes of a given peptide, here exemplified by results on the thrombin-derived peptide GKY25. Sequential truncations of the peptide yielded forms with attenuated toxicity, but retained therapeutic efficiency with respect to both antimicrobial and anti-inflammatory activity. Considering the increasing resistance problems against conventional antibiotics, a number of host defense peptides and peptidomimetics are currently undergoing clinical trials. In most cases, trials are aimed at topical indications and the direct microbicidal effects are utilized. Considering this property of AMPs, various strategies have been employed in order to optimize the therapeutic index including use of combinational library approaches [30], stereoisomers composed of D-amino acids [31] or cyclic D,L-α-peptides [32], and high-throughput based screening assays [33,34] Furthermore, a novel approach for boosting antimicrobial peptides through end-tagging with hydrophobic oligopeptide stretches have recently been demonstrated. The peptides were active ex vivo and in vivo in porcine S. aureus skin infection models, and in P. aeruginosa infected wound models [35,36,37]. Despite the potential of these approaches, naturally occurring peptide epitopes may show some advantages in a therapeutic setting considering low immunogenicity as well as inherent additional biological functions, such as the immunomodulatory activities described here. However, as shown in the present study, a systematic analysis of epitopes with respect to size as well as sequence is required in order to define and select regions with preferred activities. The necessity of this approach is exemplified by the observation that even minor differences in selection of the 20-mer region, result in different activities with respect to inactivation by plasma, observed MIC values, as well as anti-inflammatory activity.

Considering the endotoxin neutralizing activities, the mode of action of HDPs such as the here studied GKY25 may involve binding to LPS and inhibition of subsequent TLR-signaling. However, it is also possible that additional mechanisms exist, involving direct effects on host cells such as macrophages. In relation to this, it is notable that the 12-mer peptide VFR12, while showing a binding and induction of an helical conformation in presence of LPS, was not able to block LPS effects in the macrophage model. As the latter requires a size of at least 19-20 amino acids, additional mechanisms, apart from direct LPS-binding seem likely to mediate the observed anti-endotoxin effects in the macrophage model. Indeed, results show that direct LPS-interactions may not be solely explanatory for the immunomodulatory effects, since hydrophobically tagged peptides with high affinity for LPS [35,36,37] showed little antiinflammatory effects in the macrophage models (data not shown). The possible mechanisms underlying the function of GKY20/ GKY25 remains to be investigated but may include interactions with CD14 or TLRs.

As demonstrated here, peptides derived from natural HDPs, such as exemplified by GKY20, can be interesting since they retain the main properties of the parent molecule. The potential use of natural HDPs may be in situations with excessive endotoxin loads, leading to pathologic inflammation and disease. Several indications where the use of anti-endotoxic peptides may be beneficial are possible. For example, sepsis represents a common, expensive and frequently fatal condition, having a documented worldwide incidence of 1.8 million each year, but this number is confounded by a low diagnostic rate and difficulties in tracking sepsis in many countries. It is estimated that with an incidence of 3 in 1000 the true number of cases each year reaches 18 million, and with a mortality rate of almost 30% it becomes a leading cause of death worldwide. In other cases, such as in chronic leg ulcers, cystic fibrosis, or chronic obstructive lung disease, recurrent colonization and infective episodes lead to a hyper-inflammatory chronic stage. It is possible that attenuation of the excessive TLR-stimulation by immunomodulatory peptides, such as the here described GKY20 peptide, could be employed in targeting various inflammatory and infective diseases.

REFERENCES

1. French G L (2005) Clinical impact and relevance of antibiotic resistance. Adv Drug Deliv Rev 57: 1514-1527.
2. Zasloff M (2002) Antimicrobial peptides of multicellular organisms. Nature 415: 389-395.
3. Marr A K, Gooderham W J, Hancock R E (2006) Antibacterial peptides for therapeutic use: obstacles and realistic outlook. Curr Opin Pharmacol 6: 468-472.
4. Tossi A, Sandri L, Giangaspero A (2000) Amphipathic, alpha-helical antimicrobial peptides. Biopolymers 55: 4-30.
5. Brogden K A (2005) Antimicrobial peptides: pore formers or metabolic inhibitors in bacteria? Nat Rev Microbiol 3: 238-250.
6. Nizet V (2006) Antimicrobial peptide resistance mechanisms of human bacterial pathogens. Curr Issues Mol Biol 8: 11-26.
7. Huang H W (2006) Molecular mechanism of antimicrobial peptides: the origin of cooperativity. Biochim Biophys Acta 1758: 1292-1302.
8. Hancock R E, Sahl H G (2006) Antimicrobial and host-defense peptides as new anti-infective therapeutic strategies. Nat Biotechnol 24: 1551-1557.
9. Zanetti M (2004) Cathelicidins, multifunctional peptides of the innate immunity. J Leukoc Biol 75: 39-48.
10. Elsbach P (2003) What is the real role of antimicrobial polypeptides that can mediate several other inflammatory responses? J Clin Invest 111: 1643-1645.
11. Ganz T (2003) Defensins: antimicrobial peptides of innate immunity. Nat Rev Immunol 3: 710-720.
12. Cole A M, Ganz T, Liese A M, Burdick M D, Liu L, et al. (2001) Cutting edge: IFN-inducible ELR-CXC chemokines display defensin-like antimicrobial activity. J Immunol 167: 623-627.
13. Kowalska K, Carr D B, Lipkowski A W (2002) Direct antimicrobial properties of substance P. Life Sci 71: 747-750.
14. Mor A, Amiche M, Nicolas P (1994) Structure, synthesis, and activity of dermaseptin b, a novel vertebrate defensive peptide from frog skin: relationship with adenoregulin. Biochemistry 33: 6642-6650.
15. Malmsten M, Davoudi M, Walse B, Rydengard V, Pasupuleti M, et al. (2007) Antimicrobial peptides derived from growth factors. Growth Factors 25: 60-70.
16. Nordahl E A, Rydengard V, Nyberg P, Nitsche D P, Morgelin M, et al. (2004) Activation of the complement system generates antibacterial peptides. Proc Natl Acad Sci USA 101: 16879-16884.
17. Pasupuleti M, Walse B, Nordahl E A, Morgelin M, Malmsten M, et al. (2007) Preservation of antimicrobial properties of complement peptide C3a, from invertebrates to humans. J Biol Chem 282: 2520-2528.
18. Frick I M, Akesson P, Herwald H, Morgelin M, Malmsten M, et al. (2006) The contact system—a novel branch of innate immunity generating antibacterial peptides. Embo J 25: 5569-5578.
19. Nordahl E A, Rydengard V, Morgelin M, Schmidtchen A (2005) Domain 5 of high molecular weight kininogen is antibacterial. J Biol Chem 280: 34832-34839.
20. Rydengard V, Andersson Nordahl E, Schmidtchen A (2006) Zinc potentiates the antibacterial effects of histidine-rich peptides against Enterococcus faecalis. Febs J 273: 2399-2406.
21. Papareddy P, Rydengard V, Pasupuleti M, Walse B, Morgelin M, et al. Proteolysis of human thrombin generates novel host defense peptides. PLoS Pathog 6: e1000857.
22. Lehrer R I, Rosenman M, Harvig S S, Jackson R, Eisenhauer P (1991) Ultrasensitive assays for endogenous antimicrobial polypeptides. J Immunol Methods 137: 167-173.
23. Nordahl E A, Rydengard V, Nyberg P, Nitsche D P, Mörgelin M, et al. (2004) Activation of the complement system generates antibacterial peptides. Proc Natl Acad Sci USA 101: 16879-16884.
24. Wiegand I, Hilpert K, Hancock R E (2008) Agar and broth dilution methods to determine the minimal inhibitory concentration (MIC) of antimicrobial substances. Nat Protoc 3: 163-175.
25. Pollock J S, Forstermann U, Mitchell J A, Warner T D, Schmidt H H, et al. (1991) Purification and characterization of particulate endothelium-derived relaxing factor synthase from cultured and native bovine aortic endothelial cells. Proc Natl Acad Sci USA 88: 10480-10484.
26. Greenfield N, Fasman G D (1969) Computed circular dichroism spectra for the evaluation of protein conformation. Biochemistry 8: 4108-4116.
27. Sjogren H, Ulvenlund S (2005) Comparison of the helix-coil transition of a titrating polypeptide in aqueous solutions and at the air-water interface. Biophys Chem 116: 11-21.
28. Luo P, Baldwin R L (2002) Origin of the different strengths of the (i,i+4) and (i,i+3) leucine pair interactions in helices. Biophys Chem 96: 103-108.
29. Pasupuleti M, Walse B, Svensson B, Malmsten M, Schmidtchen A (2008) Rational design of antimicrobial C3a analogues with enhanced effects against Staphylococci using an integrated structure and function-based approach. Biochemistry 47: 9057-9070.
30. Blondelle S E, Lohner K (2000) Combinatorial libraries: a tool to design antimicrobial and antifungal peptide analogues having lytic specificities for structure-activity relationship studies. Biopolymers 55: 74-87.
31. Sajjan U S, Tran L T, Sole N, Rovaldi C, Akiyama A, et al. (2001) P-113D, an antimicrobial peptide active against Pseudomonas aeruginosa, retains activity in the presence of sputum from cystic fibrosis patients. Antimicrob Agents Chemother 45: 3437-3444.
32. Fermandez-Lopez S, Kim H S, Chol E C, Delgado M, Granja J R, et al. (2001) Antibacterial agents based on the cyclic D,L-alpha-peptide architecture. Nature 412: 452-455.
33. Hilpert K, Volkmer-Engert R, Walter T, Hancock R E (2005) High-throughput generation of small antibacterial peptides with improved activity. Nat Biotechnol 23: 1008-1012.

34. Taboureau O, Olsen O H, Nielsen J D, Raventos D, Mygind P H, et al. (2006) Design of novispirin antimicrobial peptides by quantitative structure-activity relationship. Chem Biol Drug Des 68: 48-57.

35. Schmidtchen A, Pasupuleti M, Morgelin M, Davoudi M, Alenfall J, et al. (2009) Boosting antimicrobial peptides by hydrophobic oligopeptide end tags. J Biol Chem 284: 17584-17594.

36. Pasupuleti M, Chalupka A, Morgelin M, Schmidtchen A, Malmsten M (2009) Tryptophan end-tagging of antimicrobial peptides for increased potency against *Pseudomonas aeruginosa*. Biochim Biophys Acta 1790: 800-808.

37. Pasupuleti M, Schmidtchen A, Chalupka A, Ringstad L, Malmsten M (2009) End-tagging of ultra-short antimicrobial peptides by W/F stretches to facilitate bacterial killing. PLoS One 4: e5285.

The invention claimed is:

1. A method for treating inflammation and coagulation of the blood in a patient, the method comprising administering to the patient a therapeutically-effective amount of a polypeptide comprising the amino acid sequence selected from the group consisting of GKYGFYTHVFRLKKWIQKVI; [SEQ ID NO: 3]
and

KYGFYTHVFRLKKWIQKVID, [SEQ ID NO: 4]

wherein the polypeptide has a length of 20 to 25 amino acids.

2. The method according to claim 1, wherein the polypeptide comprises the amino acid sequence of SEQ ID NO: 3

GKYGFYTHVFRLKKWIQKVI. [SEQ ID NO: 3]

3. The method according to claim 1, wherein the polypeptide consists of the amino acid sequence of SEQ ID NOs: 3 or 4.

4. The method according to claim 1, wherein said inflammation and coagulation of the blood in a patient is associated with a condition or indication selected from the following:
   i) Acute systemic inflammatory disease, with or without an infective component, systemic inflammatory response syndrome (SIRS), acute respiratory distress syndrome (ARDS), erysipelas, meningitis, arthritis, appendicitis, pancreatitis, cholecystitis, colitis, cellulitis,;
   ii) Chronic inflammatory diseases, cystic fibrosis, chronic obstructive pulmonary disease (COPD) pulmonary diseases, gastrointestinal disease, chronic skin and stomach ulcerations, epithelial inflammatory, oral ulcerations (aphtous ulcers), genital ulcerations and inflammatory changes, parodontitis, eye inflammations, conjunctivitis and keratitis, external otitis, mediaotitis, genitourinary inflammations;
   iii) Postoperative inflammation, thrombosis, disseminated intravasal coagulation (DIC), postoperative coagulation disorders, coagulative disorders related to contact with foreign material, and vasculitis related inflammatory disease; or
   iv) Excessive contact activation and/or coagulation in relation to stroke.

5. The method according to claim 1, wherein said inflammation and coagulation of the blood in a patient is associated with acute inflammation, acute respiratory distress syndrome (ARDS), chronic obstructive pulmonary disease (COPD), cystic fibrosis, cutaneous and systemic vasculitis, thrombosis and disseminated intravascular coagulation (DIC).

6. The method according to claim 1, wherein the polypeptide comprises the amino acid sequence of SEQ ID NO: 4

KYGFYTHVFRLKKWIQKVID. [SEQ ID NO: 4]

7. The method according to claim 1, wherein the polypeptide has a length of 20, 21, 22, 23, 24 or 25 amino acid residues.

* * * * *

SEQUENCE LISTING

```
<160> NUMBER OF SEQ ID NOS: 98

<210> SEQ ID NO 1
<211> LENGTH: 29
<212> TYPE: PRT
<213> ORGANISM: Artificial Sequence
<220> FEATURE:
<223> OTHER INFORMATION: Thrombin-derived peptide
<220> FEATURE:
<221> NAME/KEY: VARIANT
<222> LOCATION: 1
<223> OTHER INFORMATION: Xaa is any amino acid
<220> FEATURE:
<221> NAME/KEY: VARIANT
<222> LOCATION: 7
<223> OTHER INFORMATION: Xaa is any amino acid
<220> FEATURE:
<221> NAME/KEY: VARIANT
<222> LOCATION: (9)...(10)
<223> OTHER INFORMATION: Xaa is any amino acid
<220> FEATURE:
<221> NAME/KEY: VARIANT
<222> LOCATION: (12)...(14)
<223> OTHER INFORMATION: Xaa is any amino acid
<220> FEATURE:
<221> NAME/KEY: VARIANT
<222> LOCATION: 16
<223> OTHER INFORMATION: Xaa is Ile or Met
<220> FEATURE:
<221> NAME/KEY: VARIANT
<222> LOCATION: (17)...(17)
<223> OTHER INFORMATION: Xaa is any amino acid
<220> FEATURE:
<221> NAME/KEY: VARIANT
<222> LOCATION: (19)...(22)
<223> OTHER INFORMATION: Xaa is any amino acid
<220> FEATURE:
<221> NAME/KEY: VARIANT
<222> LOCATION: (23)...(29)
<223> OTHER INFORMATION: Xaa is any amino acid or absent

<400> SEQUENCE: 1

Xaa Lys Tyr Gly Phe Tyr Xaa His Xaa Xaa Arg Xaa Xaa Xaa Trp Xaa
 1               5                  10                  15

Xaa Lys Xaa Xaa Xaa Xaa Xaa Xaa Xaa Xaa Xaa Xaa Xaa
            20                  25

<210> SEQ ID NO 2
<211> LENGTH: 25
<212> TYPE: PRT
<213> ORGANISM: Artificial Sequence
<220> FEATURE:
<223> OTHER INFORMATION: GKY25 peptide

<400> SEQUENCE: 2

Gly Lys Tyr Gly Phe Tyr Thr His Val Phe Arg Leu Lys Lys Trp Ile
 1               5                  10                  15

Gln Lys Val Ile Asp Gln Phe Gly Glu
            20                  25
```

```
<210> SEQ ID NO 3
<211> LENGTH: 20
<212> TYPE: PRT
<213> ORGANISM: Artificial Sequence
<220> FEATURE:
<223> OTHER INFORMATION: GKY20 peptide

<400> SEQUENCE: 3

Gly Lys Tyr Gly Phe Tyr Thr His Val Phe Arg Leu Lys Lys Trp Ile
1               5                   10                  15

Gln Lys Val Ile
            20

<210> SEQ ID NO 4
<211> LENGTH: 20
<212> TYPE: PRT
<213> ORGANISM: Artificial Sequence
<220> FEATURE:
<223> OTHER INFORMATION: KYG20 peptide

<400> SEQUENCE: 4

Lys Tyr Gly Phe Tyr Thr His Val Phe Arg Leu Lys Lys Trp Ile Gln
1               5                   10                  15

Lys Val Ile Asp
            20

<210> SEQ ID NO 5
<211> LENGTH: 18
<212> TYPE: PRT
<213> ORGANISM: Artificial Sequence
<220> FEATURE:
<223> OTHER INFORMATION: HVF18

<400> SEQUENCE: 5

His Val Phe Arg Leu Lys Lys Trp Ile Gln Lys Val Ile Asp Gln Phe
1               5                   10                  15

Gly Glu

<210> SEQ ID NO 6
<211> LENGTH: 17
<212> TYPE: PRT
<213> ORGANISM: Artificial Sequence
<220> FEATURE:
<223> OTHER INFORMATION: VFR17

<400> SEQUENCE: 6

Val Phe Arg Leu Lys Lys Trp Ile Gln Lys Val Ile Asp Gln Phe Gly
1               5                   10                  15

Glu

<210> SEQ ID NO 7
<211> LENGTH: 20
<212> TYPE: PRT
<213> ORGANISM: Artificial Sequence
<220> FEATURE:
<223> OTHER INFORMATION: FYT20 peptide

<400> SEQUENCE: 7

Phe Tyr Thr His Val Phe Arg Leu Lys Lys Trp Ile Gln Lys Val Ile
1               5                   10                  15

Asp Gln Phe Gly
            20

<210> SEQ ID NO 8
<211> LENGTH: 20
```

```
<212> TYPE: PRT
<213> ORGANISM: Artificial Sequence
<220> FEATURE:
<223> OTHER INFORMATION: Levomeric isoform 1 described by Yount and
      Yeaman
<220> FEATURE:
<221> NAME/KEY: MISC_FEATURE
<222> LOCATION: (2)..(14)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is any amino acid
<220> FEATURE:
<221> NAME/KEY: MISC_FEATURE
<222> LOCATION: (18)..(19)
<223> OTHER INFORMATION: Xaa is any amino acid

<400> SEQUENCE: 8

Cys Xaa Xaa Xaa Xaa Xaa Xaa Xaa Xaa Xaa Xaa Xaa Xaa Cys Xaa
1               5                   10                  15

Gly Xaa Xaa Pro
            20

<210> SEQ ID NO 9
<211> LENGTH: 16
<212> TYPE: PRT
<213> ORGANISM: Artificial Sequence
<220> FEATURE:
<223> OTHER INFORMATION: 16-mer peptide from fraction 30 of RP-HPLC

<400> SEQUENCE: 9

Phe Arg Leu Lys Lys Trp Ile Gln Lys Val Ile Asp Gln Phe Gly Glu
1               5                   10                  15

<210> SEQ ID NO 10
<211> LENGTH: 29
<212> TYPE: PRT
<213> ORGANISM: Artificial Sequence
<220> FEATURE:
<223> OTHER INFORMATION: Pattern sequence found in factor XI and
      kallikrein
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (21)..(21)
<223> OTHER INFORMATION: Xaa is any amino acid
<220> FEATURE:
<221> NAME/KEY: MISC_FEATURE
<222> LOCATION: (23)..(23)
<223> OTHER INFORMATION: Xaa is any amino acid
<220> FEATURE:
<221> NAME/KEY: MISC_FEATURE
<222> LOCATION: (27)..(27)
<223> OTHER INFORMATION: Xaa is any amino acid
<220> FEATURE:
<221> NAME/KEY: MISC_FEATURE
<222> LOCATION: (29)..(29)
<223> OTHER INFORMATION: Xaa is any amino acid

<400> SEQUENCE: 10

Asp Ser Xaa Pro Phe Tyr Gly Phe Ile Val Tyr Thr Xaa Val Cys Ala
1               5                   10                  15

Glu Gln Arg Tyr Xaa Arg Xaa Trp Ile Leu Xaa His Xaa
            20                  25
```

```
<210> SEQ ID NO 11
<211> LENGTH: 12
<212> TYPE: PRT
<213> ORGANISM: Artificial Sequence
<220> FEATURE:
<223> OTHER INFORMATION: Omiganan peptide

<400> SEQUENCE: 11

Ile Leu Arg Trp Pro Trp Trp Pro Trp Arg Arg Lys
1               5                   10

<210> SEQ ID NO 12
<211> LENGTH: 37
<212> TYPE: PRT
<213> ORGANISM: Artificial Sequence
<220> FEATURE:
<223> OTHER INFORMATION: LL-37 peptide

<400> SEQUENCE: 12

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 13
<211> LENGTH: 11
<212> TYPE: PRT
<213> ORGANISM: Artificial Sequence
<220> FEATURE:
<223> OTHER INFORMATION: Possible prothrombin sequence obtained from
      fraction 20 of RP-HPLC

<400> SEQUENCE: 13

Tyr Lys Gly Arg Val Thr Gly Trp Gly Asn Leu
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Possible prothrombin sequence obtained from
      fraction 20 of RP-HPLC

<400> SEQUENCE: 14

Tyr Gly Phe Tyr Thr His Val Phe Arg Leu Lys Lys Trp Ile
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Possible prothrombin sequence obtained from
      fraction 20 of RP-HPLC

<400> SEQUENCE: 15

Thr His Val Phe Arg Leu Lys Lys Trp Ile Gln Lys Val Ile
1               5                   10

<210> SEQ ID NO 16
<211> LENGTH: 20
<212> TYPE: PRT
<213> ORGANISM: Artificial Sequence
<220> FEATURE:
```

<223> OTHER INFORMATION: Possible prothrombin sequence obtained from
      fraction 20 of RP-HPLC

<400> SEQUENCE: 16

Phe Val Met Lys Ser Pro Phe Asn Asn Arg Trp Tyr Gln Met Gly Ile
1               5                   10                  15

Val Ser Trp Gly
            20

<210> SEQ ID NO 17
<211> LENGTH: 23
<212> TYPE: PRT
<213> ORGANISM: Artificial Sequence
<220> FEATURE:
<223> OTHER INFORMATION: Possible prothrombin sequence obtained from
      fraction 20 of RP-HPLC

<400> SEQUENCE: 17

Lys Ser Pro Phe Asn Asn Arg Trp Tyr Gln Met Gly Ile Val Ser Trp
1               5                   10                  15

Gly Glu Gly Cys Asp Arg Asp
            20

<210> SEQ ID NO 18
<211> LENGTH: 36
<212> TYPE: PRT
<213> ORGANISM: Artificial Sequence
<220> FEATURE:
<223> OTHER INFORMATION: Possible prothrombin sequence obtained from
      fraction 20 of RP-HPLC

<400> SEQUENCE: 18

Val Met Lys Ser Pro Phe Asn Asn Arg Trp Tyr Gln Met Gly Ile Val
1               5                   10                  15

Ser Trp Gly Glu Gly Cys Asp Arg Asp Gly Lys Tyr Gly Phe Tyr Thr
            20                  25                  30

His Val Phe Arg
        35

<210> SEQ ID NO 19
<211> LENGTH: 11
<212> TYPE: PRT
<213> ORGANISM: Artificial Sequence
<220> FEATURE:
<223> OTHER INFORMATION: Possible prothrombin sequence obtained from
      fraction 21 of RP-HPLC

<400> SEQUENCE: 19

Tyr Lys Gly Arg Val Thr Gly Trp Gly Asn Leu
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Possible prothrombin sequence obtained from
      fraction 21 of RP-HPLC

<400> SEQUENCE: 20

Lys Tyr Gly Phe Tyr Thr His Val Phe Arg Leu
1               5                   10

<210> SEQ ID NO 21
<211> LENGTH: 16
<212> TYPE: PRT

<213> ORGANISM: Artificial Sequence
<220> FEATURE:
<223> OTHER INFORMATION: Possible prothrombin sequence obtained from fraction 21 of RP-HPLC

<400> SEQUENCE: 21

Phe Asn Asn Arg Trp Tyr Gln Met Gly Ile Val Ser Trp Gly Glu Gly
1 5 10 15

<210> SEQ ID NO 22
<211> LENGTH: 25
<212> TYPE: PRT
<213> ORGANISM: Artificial Sequence
<220> FEATURE:
<223> OTHER INFORMATION: Possible prothrombin sequence obtained from fraction 21 of RP-HPLC

<400> SEQUENCE: 22

Ala Ser Leu Leu Gln Ala Gly Tyr Lys Gly Arg Val Thr Gly Trp Gly
1 5 10 15

Asn Leu Lys Glu Thr Trp Thr Ala Asn
20 25

<210> SEQ ID NO 23
<211> LENGTH: 25
<212> TYPE: PRT
<213> ORGANISM: Artificial Sequence
<220> FEATURE:
<223> OTHER INFORMATION: GKY25(X) peptide

<400> SEQUENCE: 23

Gly Lys Tyr Gly Ile Tyr Thr Lys Val Thr Ala Phe Leu Lys Trp Ile
1 5 10 15

Asp Arg Ser Met Lys Thr Arg Gly Leu
20 25

<210> SEQ ID NO 24
<211> LENGTH: 23
<212> TYPE: PRT
<213> ORGANISM: Artificial Sequence
<220> FEATURE:
<223> OTHER INFORMATION: GKY23 peptide

<400> SEQUENCE: 24

Gly Lys Tyr Gly Ile Tyr Thr Lys Val Ser Arg Tyr Val Asn Trp Ile
1 5 10 15

Lys Glu Lys Thr Lys Leu Thr
20

<210> SEQ ID NO 25
<211> LENGTH: 23
<212> TYPE: PRT
<213> ORGANISM: Artificial Sequence
<220> FEATURE:
<223> OTHER INFORMATION: ERP23 peptide

<400> SEQUENCE: 25

Glu Arg Pro Gly Val Tyr Thr Asn Val Val Glu Tyr Val Asp Trp Ile
1 5 10 15

Leu Glu Lys Thr Gln Ala Val
20

<210> SEQ ID NO 26
<211> LENGTH: 25
<212> TYPE: PRT
<213> ORGANISM: Artificial Sequence

```
<220> FEATURE:
<223> OTHER INFORMATION: EQP25 peptide

<400> SEQUENCE: 26

Glu Gln Pro Gly Val Tyr Thr Lys Val Ala Glu Tyr Met Asp Trp Ile
1               5                   10                  15

Leu Glu Lys Thr Gln Ser Ser Asp Gly
            20                  25

<210> SEQ ID NO 27
<211> LENGTH: 25
<212> TYPE: PRT
<213> ORGANISM: Artificial Sequence
<220> FEATURE:
<223> OTHER INFORMATION: WFF25 peptide

<400> SEQUENCE: 27

Trp Phe Phe Phe Tyr Tyr Leu Ile Ile Gly Gly Gly Val Val Thr His
1               5                   10                  15

Gln Gln Arg Lys Lys Lys Asp Glu
            20                  25

<210> SEQ ID NO 28
<211> LENGTH: 12
<212> TYPE: PRT
<213> ORGANISM: Artificial Sequence
<220> FEATURE:
<223> OTHER INFORMATION: 12-mer thrombin-derived peptide

<400> SEQUENCE: 28

Val Phe Arg Leu Lys Lys Trp Ile Gln Lys Val Ile
1               5                   10

<210> SEQ ID NO 29
<211> LENGTH: 16
<212> TYPE: PRT
<213> ORGANISM: Artificial Sequence
<220> FEATURE:
<223> OTHER INFORMATION: 16-mer thrombin-derived peptides

<400> SEQUENCE: 29

Thr His Val Phe Arg Leu Lys Lys Trp Ile Gln Lys Val Ile Asp Gln
1               5                   10                  15

<210> SEQ ID NO 30
<211> LENGTH: 20
<212> TYPE: PRT
<213> ORGANISM: Artificial Sequence
<220> FEATURE:
<223> OTHER INFORMATION: Proposed gamma-core motif of thrombin

<400> SEQUENCE: 30

Cys Lys Asp Ser Thr Arg Ile Arg Ile Thr Asp Asn Met Phe Cys Ala
1               5                   10                  15

Gly Tyr Lys Pro
            20

<210> SEQ ID NO 31
<211> LENGTH: 579
<212> TYPE: PRT
<213> ORGANISM: Homo sapiens

<400> SEQUENCE: 31

Ala Asn Thr Phe Leu Glu Glu Val Arg Lys Gly Asn Leu Glu Arg Glu
1               5                   10                  15
```

-continued

Cys Val Glu Glu Thr Cys Ser Tyr Glu Glu Ala Phe Glu Ala Leu Glu
        20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
    210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270

Ala Thr Ser Glu Tyr Gln Thr Phe Phe Asn Pro Arg Thr Phe Gly Ser
        275                 280                 285

Gly Glu Ala Asp Cys Gly Leu Arg Pro Leu Phe Glu Lys Lys Ser Leu
    290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
    370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Lys Pro Val Ala Phe Ser
            420                 425                 430

Asp Tyr Ile His Pro Val Cys Leu Pro Asp Arg Glu Thr Ala Ala Ser
        435                 440                 445

```
Leu Leu Gln Ala Gly Tyr Lys Gly Arg Val Thr Gly Trp Gly Asn Leu
    450                 455                 460

Lys Glu Thr Trp Thr Ala Asn Val Gly Lys Gly Gln Pro Ser Val Leu
465                 470                 475                 480

Gln Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
            500                 505                 510

Asp Glu Gly Lys Arg Gly Asp Ala Cys Glu Gly Asp Ser Gly Gly Pro
        515                 520                 525

Phe Val Met Lys Ser Pro Phe Asn Asn Arg Trp Tyr Gln Met Gly Ile
    530                 535                 540

Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 32
<211> LENGTH: 106
<212> TYPE: PRT
<213> ORGANISM: Danio rerio

<400> SEQUENCE: 32

Ala Val Leu Gln Gln Ile His Leu Pro Ile Val Asp Gln Ser Ile Cys
1               5                   10                  15

Arg Asn Ser Thr Ser Val Ile Ile Thr Asp Asn Met Phe Cys Ala Gly
            20                  25                  30

Tyr Gln Pro Asp Asp Ser Lys Arg Gly Asp Ala Cys Glu Gly Asp Ser
        35                  40                  45

Gly Gly Pro Phe Val Met Lys Ser Pro Ser Asp Asn Arg Trp Tyr Gln
    50                  55                  60

Ile Gly Ile Val Ser Trp Gly Glu Gly Cys Asp Arg Asp Gly Lys Tyr
65                  70                  75                  80

Gly Phe Tyr Thr His Leu Phe Arg Met Arg Arg Trp Met Lys Lys Val
                85                  90                  95

Ile Glu Lys Thr Asp Ser Gly Asp Asp Glu
            100                 105

<210> SEQ ID NO 33
<211> LENGTH: 106
<212> TYPE: PRT
<213> ORGANISM: Oncorhynchus mykiss

<400> SEQUENCE: 33

Thr Val Leu Gln Gln Ile His Leu Pro Ile Val Glu Gln Asp Ile Cys
1               5                   10                  15

Arg Asp Ser Thr Ser Ile Arg Ile Thr Asp Asn Met Phe Cys Ala Gly
            20                  25                  30

Phe Lys Pro Glu Glu Gln Lys Thr Gly Asp Ala Cys Glu Gly Asp Ser
        35                  40                  45

Gly Gly Pro Phe Val Met Lys Ser Pro Asp Asp Asn Arg Trp Tyr Gln
    50                  55                  60

Ile Gly Ile Val Ser Trp Gly Glu Gly Cys Asp Arg Asp Gly Lys Tyr
65                  70                  75                  80

Gly Phe Tyr Thr His Leu Phe Arg Met Arg Arg Trp Met Lys Lys Val
```

```
                    85                  90                  95

Ile Asp Lys Thr Gly Gly Asp Asp Asp
            100                 105

<210> SEQ ID NO 34
<211> LENGTH: 101
<212> TYPE: PRT
<213> ORGANISM: Acipenser transmontanus

<400> SEQUENCE: 34

Gln Val Leu Gln Gln Ile His Leu Pro Ile Val Gln Gln Glu Thr Cys
1               5                   10                  15

Arg Asp Ser Thr Lys Ile Arg Val Thr Asp Asn Met Phe Cys Ala Gly
            20                  25                  30

Phe Ser Pro Glu Asp Ser Ile Ser Gly Asp Ser Cys Glu Gly Asp Ser
        35                  40                  45

Gly Gly Pro Phe Val Met Lys Asn Pro Glu Asp Asp Arg Trp Tyr Gln
    50                  55                  60

Ile Gly Ile Val Ser Trp Gly Glu Gly Cys Asp Arg Ser Gly Lys Tyr
65                  70                  75                  80

Gly Phe Tyr Thr His Leu Phe Arg Met Arg Lys Trp Met Leu Lys Thr
                85                  90                  95

Ile Val Asp Thr Glu
            100

<210> SEQ ID NO 35
<211> LENGTH: 103
<212> TYPE: PRT
<213> ORGANISM: Eptatretus stouti

<400> SEQUENCE: 35

Arg Val Leu Gln Leu Ile Asn Leu Pro Ile Val Asp Thr Arg Thr Cys
1               5                   10                  15

His Asp Ser Thr Thr Ile Lys Ile Thr Arg Asn Met Phe Cys Ala Gly
            20                  25                  30

Tyr Ser Pro Glu Asp Met Lys Arg Gly Asp Pro Cys Glu Gly Asp Ser
        35                  40                  45

Gly Gly Pro Phe Val Met Lys Asn Pro Glu Gln Asn Arg Trp Tyr Gln
    50                  55                  60

Val Gly Ile Val Ser Trp Gly Glu Gly Cys Asp Lys Asp Gly Lys Tyr
65                  70                  75                  80

Gly Phe Tyr Thr His Leu Phe Arg Met Leu Arg Trp Leu Lys Lys Ile
                85                  90                  95

Val Asn Arg Glu Gly Ala Arg
            100

<210> SEQ ID NO 36
<211> LENGTH: 101
<212> TYPE: PRT
<213> ORGANISM: Gallus gallus

<400> SEQUENCE: 36

Thr Val Leu Gln Gln Leu Asn Leu Pro Ile Val Asp Gln Asn Thr Cys
1               5                   10                  15

Lys Ala Ser Thr Arg Val Lys Val Thr Asp Asn Met Phe Cys Ala Gly
            20                  25                  30

Tyr Ser Pro Glu Asp Ser Lys Arg Gly Asp Ala Cys Glu Gly Asp Ser
        35                  40                  45
```

```
Gly Gly Pro Phe Val Met Lys Asn Pro Asp Asp Asn Arg Trp Tyr Gln
        50                  55                  60

Val Gly Ile Val Ser Trp Gly Glu Gly Cys Asp Arg Asp Gly Lys Tyr
65                  70                  75                  80

Gly Phe Tyr Thr His Val Phe Arg Leu Lys Lys Trp Met Arg Lys Thr
                85                  90                  95

Ile Glu Lys Gln Gly
            100

<210> SEQ ID NO 37
<211> LENGTH: 102
<212> TYPE: PRT
<213> ORGANISM: Struthio camelus

<400> SEQUENCE: 37

Thr Val Leu Gln Gln Leu Asn Val Pro Ile Val Asp Gln Asp Thr Cys
1               5                   10                  15

Lys Ala Ser Thr Lys Val Lys Val Thr Asp Asn Met Phe Cys Ala Gly
                20                  25                  30

Tyr Ser Pro Glu Asp Ser Lys Arg Gly Asp Ala Cys Glu Gly Asp Ser
            35                  40                  45

Gly Gly Pro Phe Val Met Lys Ser Pro Asp Asp Ser Arg Trp Tyr Gln
        50                  55                  60

Val Gly Ile Val Ser Trp Gly Glu Gly Cys Asp Arg Asp Gly Lys Tyr
65                  70                  75                  80

Gly Phe Tyr Thr His Val Phe Arg Leu Lys Lys Trp Ile Arg Lys Ala
                85                  90                  95

Ile Glu Arg Tyr Met Gln
            100

<210> SEQ ID NO 38
<211> LENGTH: 102
<212> TYPE: PRT
<213> ORGANISM: Gekko gecko

<400> SEQUENCE: 38

Thr Tyr Leu Gln Leu Val Asn Leu Pro Ile Val Asp Arg Asp Thr Cys
1               5                   10                  15

Lys Ala Ser Thr Lys Ile Lys Ile Thr Asp Asn Met Phe Cys Ala Gly
                20                  25                  30

Tyr Ser Pro Glu Asp Ser Lys Arg Gly Asp Ala Cys Glu Gly Asp Ser
            35                  40                  45

Gly Gly Pro Phe Val Met Lys Asn Pro Gln Asp Asn Arg Trp Tyr Gln
        50                  55                  60

Val Gly Ile Val Ser Trp Gly Glu Gly Cys Asp Arg Asp Gly Lys Tyr
65                  70                  75                  80

Gly Phe Tyr Thr His Val Phe Arg Leu Lys Lys Trp Leu Lys Lys Thr
                85                  90                  95

Val Glu Lys His Gly Asn
            100

<210> SEQ ID NO 39
<211> LENGTH: 102
<212> TYPE: PRT
<213> ORGANISM: Xenopus silurana

<400> SEQUENCE: 39

Gln Ala Leu Gln Gln Ile Asn Leu Pro Ile Val Asp Gln Glu Thr Cys
1               5                   10                  15
```

```
Lys Ser Ser Thr Asn Ile Lys Val Thr Asp Asn Met Phe Cys Ala Gly
            20                  25                  30

Tyr Asn Pro Glu Asp Ser Lys Arg Gly Asp Ala Cys Glu Gly Asp Ser
                35                  40                  45

Gly Gly Pro Phe Val Met Lys Asp Pro Asp Thr Gly Arg Trp Val Gln
 50                      55                  60

Leu Gly Ile Val Ser Trp Gly Glu Gly Cys Asp Arg Asp Asn Lys Tyr
 65                  70                  75                  80

Gly Phe Tyr Val His Val His Arg Met Arg Lys Trp Ile Met Lys Thr
                85                  90                  95

Val Glu Lys Phe Gly Ser
            100
```

<210> SEQ ID NO 40
<211> LENGTH: 103
<212> TYPE: PRT
<213> ORGANISM: Xenopus laevis

<400> SEQUENCE: 40

```
Gln Thr Leu Gln Gln Ile Asn Leu Pro Ile Val Asp Gln Glu Thr Cys
 1               5                  10                  15

Lys Ser Ser Thr Lys Ile Lys Ile Thr Asp Asn Met Phe Cys Ala Gly
            20                  25                  30

Tyr Ser Pro Glu Asp Ser Lys Arg Gly Asp Ala Cys Glu Gly Asp Ser
                35                  40                  45

Gly Gly Pro Phe Val Met Lys Asp Pro Asp Thr Gly Arg Trp Val Gln
 50                      55                  60

Leu Gly Ile Val Ser Trp Gly Glu Gly Cys Asp Arg Asp Gly Lys Tyr
 65                  70                  75                  80

Gly Phe Tyr Val His Leu His Arg Leu Arg Lys Trp Leu Met Lys Thr
                85                  90                  95

Ile Glu Lys Phe Gly Ser Ser
            100
```

<210> SEQ ID NO 41
<211> LENGTH: 102
<212> TYPE: PRT
<213> ORGANISM: Cynops pyrrhogaster

<400> SEQUENCE: 41

```
Gln Val Leu Gln Gln Val Asn Leu Pro Ile Val Asp Gln Glu Thr Cys
 1               5                  10                  15

Lys Ala Ser Thr Lys Ile Lys Val Thr Ser Asn Met Phe Cys Ala Gly
            20                  25                  30

Tyr Lys Pro Asp Glu Pro Asn Arg Gly Asp Ala Cys Glu Gly Asp Ser
                35                  40                  45

Gly Gly Pro Phe Val Met Lys Ser Pro Asp Asn Arg Trp Tyr Gln
 50                      55                  60

Val Gly Ile Val Ser Trp Gly Glu Gly Cys Asp Arg Asp Gly Lys Tyr
 65                  70                  75                  80

Gly Phe Tyr Thr His Leu His Arg Met Arg Gln Trp Met Met Lys Ile
                85                  90                  95

Ile Glu Lys Cys Gly Ser
            100
```

<210> SEQ ID NO 42
<211> LENGTH: 102

```
<212> TYPE: PRT
<213> ORGANISM: Homo sapiens

<400> SEQUENCE: 42

Ser Val Leu Gln Val Val Asn Leu Pro Ile Val Glu Arg Pro Val Cys
1               5                   10                  15

Lys Asp Ser Thr Arg Ile Arg Ile Thr Asp Asn Met Phe Cys Ala Gly
            20                  25                  30

Tyr Lys Pro Asp Glu Gly Lys Arg Gly Asp Ala Cys Glu Gly Asp Ser
        35                  40                  45

Gly Gly Pro Phe Val Met Lys Ser Pro Phe Asn Asn Arg Trp Tyr Gln
50                  55                  60

Met Gly Ile Val Ser Trp Gly Glu Gly Cys Asp Arg Asp Gly Lys Tyr
65                  70                  75                  80

Gly Phe Tyr Thr His Val Phe Arg Leu Lys Lys Trp Ile Gln Lys Val
                85                  90                  95

Ile Asp Gln Phe Gly Glu
            100

<210> SEQ ID NO 43
<211> LENGTH: 102
<212> TYPE: PRT
<213> ORGANISM: Macaca mulatta

<400> SEQUENCE: 43

Ser Val Leu Gln Val Val Asn Leu Pro Ile Val Glu Arg Ser Val Cys
1               5                   10                  15

Lys Asp Ser Thr Arg Ile Arg Ile Thr Asp Asn Met Phe Cys Ala Gly
            20                  25                  30

Tyr Lys Pro Gly Glu Gly Lys Arg Gly Asp Ala Cys Glu Gly Asp Ser
        35                  40                  45

Gly Gly Pro Phe Val Met Lys Asn Pro Leu Asn Lys Arg Trp Tyr Gln
50                  55                  60

Met Gly Ile Val Ser Trp Gly Glu Gly Cys Asp Arg Asp Gly Lys Tyr
65                  70                  75                  80

Gly Phe Tyr Thr His Val Phe Arg Leu Lys Lys Trp Ile Gln Lys Val
                85                  90                  95

Ile Asp Gln Phe Gly Asp
            100

<210> SEQ ID NO 44
<211> LENGTH: 102
<212> TYPE: PRT
<213> ORGANISM: Bos taurus

<400> SEQUENCE: 44

Ser Val Leu Gln Val Val Asn Leu Pro Leu Val Glu Arg Pro Val Cys
1               5                   10                  15

Lys Ala Ser Thr Arg Ile Arg Ile Thr Asp Asn Met Phe Cys Ala Gly
            20                  25                  30

Tyr Lys Pro Gly Glu Gly Lys Arg Gly Asp Ala Cys Glu Gly Asp Ser
        35                  40                  45

Gly Gly Pro Phe Val Met Lys Ser Pro Tyr Asn Asn Arg Trp Tyr Gln
50                  55                  60

Met Gly Ile Val Ser Trp Gly Glu Gly Cys Asp Arg Asp Gly Lys Tyr
65                  70                  75                  80

Gly Phe Tyr Thr His Val Phe Arg Leu Lys Lys Trp Ile Gln Lys Val
                85                  90                  95
```

```
Ile Asp Arg Leu Gly Ser
            100

<210> SEQ ID NO 45
<211> LENGTH: 102
<212> TYPE: PRT
<213> ORGANISM: Sus scrofa

<400> SEQUENCE: 45

Ser Val Leu Gln Val Ala Asn Leu Pro Ile Val Glu Arg Leu Val Cys
 1               5                  10                  15

Lys Ala Ser Thr Arg Ile Arg Ile Thr Asp Asn Met Phe Cys Ala Gly
            20                  25                  30

Tyr Lys Pro Asp Glu Gly Lys Arg Gly Asp Ala Cys Glu Gly Asp Ser
        35                  40                  45

Gly Gly Pro Phe Val Met Lys Ser Pro Phe Asn Asn Arg Trp Tyr Gln
    50                  55                  60

Met Gly Ile Val Ser Trp Gly Glu Gly Cys Asp Arg Asp Gly Lys Tyr
65                  70                  75                  80

Gly Phe Tyr Thr His Val Phe Arg Leu Lys Lys Trp Met Gln Lys Val
                85                  90                  95

Ile Asp Arg Phe Gly Gly
            100

<210> SEQ ID NO 46
<211> LENGTH: 101
<212> TYPE: PRT
<213> ORGANISM: Mus musculus

<400> SEQUENCE: 46

Ser Val Leu Gln Val Val Asn Leu Pro Ile Val Glu Arg Pro Val Cys
 1               5                  10                  15

Lys Ala Ser Thr Arg Ile Arg Ile Thr Asp Asn Met Phe Cys Ala Gly
            20                  25                  30

Phe Lys Val Asn Asp Thr Lys Arg Gly Asp Ala Cys Glu Gly Asp Ser
        35                  40                  45

Gly Gly Pro Phe Val Met Lys Ser Pro Phe Asn Asn Arg Trp Tyr Gln
    50                  55                  60

Met Gly Ile Val Ser Trp Gly Glu Gly Cys Asp Arg Lys Gly Lys Tyr
65                  70                  75                  80

Gly Phe Tyr Thr His Val Phe Arg Leu Lys Arg Trp Ile Gln Lys Val
                85                  90                  95

Ile Asp Gln Phe Gly
            100

<210> SEQ ID NO 47
<211> LENGTH: 101
<212> TYPE: PRT
<213> ORGANISM: Rattus norvegicus

<400> SEQUENCE: 47

Ser Val Leu Gln Val Val Asn Leu Pro Ile Val Glu Arg Pro Val Cys
 1               5                  10                  15

Lys Ala Ser Thr Arg Ile Arg Ile Thr Asp Asn Met Phe Cys Ala Gly
            20                  25                  30

Phe Lys Val Asn Asp Thr Lys Arg Gly Asp Ala Cys Glu Gly Asp Ser
        35                  40                  45

Gly Gly Pro Phe Val Met Lys Ser Pro Tyr Asn His Arg Trp Tyr Gln
```

```
                    50                  55                  60
Met Gly Ile Val Ser Trp Gly Glu Gly Cys Asp Arg Asn Gly Lys Tyr
 65                  70                  75                  80

Gly Phe Tyr Thr His Val Phe Arg Leu Lys Arg Trp Ile Gln Lys Val
                    85                  90                  95

Ile Asp Gln His Arg
            100

<210> SEQ ID NO 48
<211> LENGTH: 101
<212> TYPE: PRT
<213> ORGANISM: Oryctolagus cuniculus

<400> SEQUENCE: 48

Ser Val Leu Gln Met Val Asn Leu Pro Ile Val Glu Arg Pro Ile Cys
  1               5                  10                  15

Lys Ala Ser Thr Gly Ile Arg Val Thr Asp Asn Met Phe Cys Ala Gly
                 20                  25                  30

Tyr Lys Pro Glu Glu Gly Lys Arg Gly Asp Ala Cys Glu Gly Asp Ser
             35                  40                  45

Gly Gly Pro Phe Val Met Lys Asn Pro Tyr Asn Asn Arg Trp Tyr Gln
         50                  55                  60

Met Gly Ile Val Ser Trp Gly Glu Gly Cys Asp Arg Asp Gly Lys Tyr
 65                  70                  75                  80

Gly Phe Tyr Thr His Val Phe Arg Leu Lys Lys Trp Ile Arg Lys Met
                    85                  90                  95

Val Asp Arg Phe Gly
            100

<210> SEQ ID NO 49
<211> LENGTH: 102
<212> TYPE: PRT
<213> ORGANISM: Lethenteron japonicum

<400> SEQUENCE: 49

Lys Val Leu Gln Met Ile Asn Leu Pro Ile Val Asp Pro Ser Arg Cys
  1               5                  10                  15

Gln Glu Ser Thr Thr His Arg Ile Thr Ala Asn Met Leu Cys Ala Gly
                 20                  25                  30

Tyr Glu Pro Glu Asp Val Lys Arg Gly Asp Ala Cys Glu Gly Asp Ser
             35                  40                  45

Gly Gly Pro Phe Ile Met Lys Asp Phe Glu Asn Lys Arg Trp Tyr Gln
         50                  55                  60

Met Gly Ile Val Ser Trp Gly Glu Gly Cys Asp Arg Asp Gly Lys Tyr
 65                  70                  75                  80

Gly Ile Tyr Thr His Val Tyr Arg Leu Arg Lys Trp Ile Asn Lys Val
                    85                  90                  95

Ile Gly Glu Pro Asp Thr
            100

<210> SEQ ID NO 50
<211> LENGTH: 24
<212> TYPE: PRT
<213> ORGANISM: Artificial Sequence
<220> FEATURE:
<223> OTHER INFORMATION: PEP petide

<400> SEQUENCE: 50

Gly Lys Tyr Gly Phe Tyr Thr His Val Phe Arg Leu Lys Lys Trp Ile
```

```
Gln Lys Val Ile Asp Gln Phe Gly
            20

<210> SEQ ID NO 51
<211> LENGTH: 23
<212> TYPE: PRT
<213> ORGANISM: Artificial Sequence
<220> FEATURE:
<223> OTHER INFORMATION: PEP petide

<400> SEQUENCE: 51

Gly Lys Tyr Gly Phe Tyr Thr His Val Phe Arg Leu Lys Lys Trp Ile
1               5                   10                  15

Gln Lys Val Ile Asp Gln Phe
            20

<210> SEQ ID NO 52
<211> LENGTH: 22
<212> TYPE: PRT
<213> ORGANISM: Artificial Sequence
<220> FEATURE:
<223> OTHER INFORMATION: PEP petide

<400> SEQUENCE: 52

Gly Lys Tyr Gly Phe Tyr Thr His Val Phe Arg Leu Lys Lys Trp Ile
1               5                   10                  15

Gln Lys Val Ile Asp Gln
            20

<210> SEQ ID NO 53
<211> LENGTH: 21
<212> TYPE: PRT
<213> ORGANISM: Artificial Sequence
<220> FEATURE:
<223> OTHER INFORMATION: PEP petide

<400> SEQUENCE: 53

Gly Lys Tyr Gly Phe Tyr Thr His Val Phe Arg Leu Lys Lys Trp Ile
1               5                   10                  15

Gln Lys Val Ile Asp
            20

<210> SEQ ID NO 54
<211> LENGTH: 19
<212> TYPE: PRT
<213> ORGANISM: Artificial Sequence
<220> FEATURE:
<223> OTHER INFORMATION: PEP petide

<400> SEQUENCE: 54

Gly Lys Tyr Gly Phe Tyr Thr His Val Phe Arg Leu Lys Lys Trp Ile
1               5                   10                  15

Gln Lys Val

<210> SEQ ID NO 55
<211> LENGTH: 18
<212> TYPE: PRT
<213> ORGANISM: Artificial Sequence
<220> FEATURE:
<223> OTHER INFORMATION: PEP petide

<400> SEQUENCE: 55

Gly Lys Tyr Gly Phe Tyr Thr His Val Phe Arg Leu Lys Lys Trp Ile
1               5                   10                  15
```

Gln Lys

<210> SEQ ID NO 56
<211> LENGTH: 17
<212> TYPE: PRT
<213> ORGANISM: Artificial Sequence
<220> FEATURE:
<223> OTHER INFORMATION: PEP peptide

<400> SEQUENCE: 56

Gly Lys Tyr Gly Phe Tyr Thr His Val Phe Arg Leu Lys Lys Trp Ile
1               5                   10                  15

Gln

<210> SEQ ID NO 57
<211> LENGTH: 16
<212> TYPE: PRT
<213> ORGANISM: Artificial Sequence
<220> FEATURE:
<223> OTHER INFORMATION: PEP petide

<400> SEQUENCE: 57

Gly Lys Tyr Gly Phe Tyr Thr His Val Phe Arg Leu Lys Lys Trp Ile
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: PEP petide

<400> SEQUENCE: 58

Gly Lys Tyr Gly Phe Tyr Thr His Val Phe Arg Leu Lys Lys Trp
1               5                   10                  15

<210> SEQ ID NO 59
<211> LENGTH: 14
<212> TYPE: PRT
<213> ORGANISM: Artificial Sequence
<220> FEATURE:
<223> OTHER INFORMATION: PEP petide

<400> SEQUENCE: 59

Gly Lys Tyr Gly Phe Tyr Thr His Val Phe Arg Leu Lys Lys
1               5                   10

<210> SEQ ID NO 60
<211> LENGTH: 13
<212> TYPE: PRT
<213> ORGANISM: Artificial Sequence
<220> FEATURE:
<223> OTHER INFORMATION: PEP peptide

<400> SEQUENCE: 60

Gly Lys Tyr Gly Phe Tyr Thr His Val Phe Arg Leu Lys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: PEP petide

<400> SEQUENCE: 61

Gly Lys Tyr Gly Phe Tyr Thr His Val Phe Arg Leu
1               5                   10

<210> SEQ ID NO 62
<211> LENGTH: 11
<212> TYPE: PRT
<213> ORGANISM: Artificial Sequence
<220> FEATURE:
<223> OTHER INFORMATION: PEP petide

<400> SEQUENCE: 62

Gly Lys Tyr Gly Phe Tyr Thr His Val Phe Arg
1               5                   10

<210> SEQ ID NO 63
<211> LENGTH: 10
<212> TYPE: PRT
<213> ORGANISM: Artificial Sequence
<220> FEATURE:
<223> OTHER INFORMATION: PEP petide

<400> SEQUENCE: 63

Gly Lys Tyr Gly Phe Tyr Thr His Val Phe
1               5                   10

<210> SEQ ID NO 64
<211> LENGTH: 9
<212> TYPE: PRT
<213> ORGANISM: Artificial Sequence
<220> FEATURE:
<223> OTHER INFORMATION: PEP petide

<400> SEQUENCE: 64

Gly Lys Tyr Gly Phe Tyr Thr His Val
1               5

<210> SEQ ID NO 65
<211> LENGTH: 8
<212> TYPE: PRT
<213> ORGANISM: Artificial Sequence
<220> FEATURE:
<223> OTHER INFORMATION: PEP petide

<400> SEQUENCE: 65

Gly Lys Tyr Gly Phe Tyr Thr His
1               5

<210> SEQ ID NO 66
<211> LENGTH: 7
<212> TYPE: PRT
<213> ORGANISM: Artificial Sequence
<220> FEATURE:
<223> OTHER INFORMATION: PEP peptide

<400> SEQUENCE: 66

Gly Lys Tyr Gly Phe Tyr Thr
1               5

<210> SEQ ID NO 67
<211> LENGTH: 6
<212> TYPE: PRT
<213> ORGANISM: Artificial Sequence
<220> FEATURE:
<223> OTHER INFORMATION: PEP petide

<400> SEQUENCE: 67

Gly Lys Tyr Gly Phe Tyr
1               5

```
<210> SEQ ID NO 68
<211> LENGTH: 24
<212> TYPE: PRT
<213> ORGANISM: Artificial Sequence
<220> FEATURE:
<223> OTHER INFORMATION: PEP petide

<400> SEQUENCE: 68

Lys Tyr Gly Phe Tyr Thr His Val Phe Arg Leu Lys Lys Trp Ile Gln
1               5                   10                  15

Lys Val Ile Asp Gln Phe Gly Glu
            20

<210> SEQ ID NO 69
<211> LENGTH: 23
<212> TYPE: PRT
<213> ORGANISM: Artificial Sequence
<220> FEATURE:
<223> OTHER INFORMATION: PEP petide

<400> SEQUENCE: 69

Tyr Gly Phe Tyr Thr His Val Phe Arg Leu Lys Lys Trp Ile Gln Lys
1               5                   10                  15

Val Ile Asp Gln Phe Gly Glu
            20

<210> SEQ ID NO 70
<211> LENGTH: 22
<212> TYPE: PRT
<213> ORGANISM: Artificial Sequence
<220> FEATURE:
<223> OTHER INFORMATION: PEP petide

<400> SEQUENCE: 70

Gly Phe Tyr Thr His Val Phe Arg Leu Lys Lys Trp Ile Gln Lys Val
1               5                   10                  15

Ile Asp Gln Phe Gly Glu
            20

<210> SEQ ID NO 71
<211> LENGTH: 21
<212> TYPE: PRT
<213> ORGANISM: Artificial Sequence
<220> FEATURE:
<223> OTHER INFORMATION: PEP petide

<400> SEQUENCE: 71

Phe Tyr Thr His Val Phe Arg Leu Lys Lys Trp Ile Gln Lys Val Ile
1               5                   10                  15

Asp Gln Phe Gly Glu
            20

<210> SEQ ID NO 72
<211> LENGTH: 20
<212> TYPE: PRT
<213> ORGANISM: Artificial Sequence
<220> FEATURE:
<223> OTHER INFORMATION: PEP petide

<400> SEQUENCE: 72

Tyr Thr His Val Phe Arg Leu Lys Lys Trp Ile Gln Lys Val Ile Asp
1               5                   10                  15

Gln Phe Gly Glu
            20
```

<210> SEQ ID NO 73
<211> LENGTH: 19
<212> TYPE: PRT
<213> ORGANISM: Artificial Sequence
<220> FEATURE:
<223> OTHER INFORMATION: PEP petide

<400> SEQUENCE: 73

Thr His Val Phe Arg Leu Lys Lys Trp Ile Gln Lys Val Ile Asp Gln
1               5                   10                  15

Phe Gly Glu

<210> SEQ ID NO 74
<211> LENGTH: 15
<212> TYPE: PRT
<213> ORGANISM: Artificial Sequence
<220> FEATURE:
<223> OTHER INFORMATION: PEP petide

<400> SEQUENCE: 74

Arg Leu Lys Lys Trp Ile Gln Lys Val Ile Asp Gln Phe Gly Glu
1               5                   10                  15

<210> SEQ ID NO 75
<211> LENGTH: 14
<212> TYPE: PRT
<213> ORGANISM: Artificial Sequence
<220> FEATURE:
<223> OTHER INFORMATION: PEP petide

<400> SEQUENCE: 75

Leu Lys Lys Trp Ile Gln Lys Val Ile Asp Gln Phe Gly Glu
1               5                   10

<210> SEQ ID NO 76
<211> LENGTH: 13
<212> TYPE: PRT
<213> ORGANISM: Artificial Sequence
<220> FEATURE:
<223> OTHER INFORMATION: PEP petide

<400> SEQUENCE: 76

Lys Lys Trp Ile Gln Lys Val Ile Asp Gln Phe Gly Glu
1               5                   10

<210> SEQ ID NO 77
<211> LENGTH: 12
<212> TYPE: PRT
<213> ORGANISM: Artificial Sequence
<220> FEATURE:
<223> OTHER INFORMATION: PEP petide

<400> SEQUENCE: 77

Lys Trp Ile Gln Lys Val Ile Asp Gln Phe Gly Glu
1               5                   10

<210> SEQ ID NO 78
<211> LENGTH: 11
<212> TYPE: PRT
<213> ORGANISM: Artificial Sequence
<220> FEATURE:
<223> OTHER INFORMATION: PEP petide

<400> SEQUENCE: 78

Trp Ile Gln Lys Val Ile Asp Gln Phe Gly Glu
1               5                   10

-continued

```
<210> SEQ ID NO 79
<211> LENGTH: 10
<212> TYPE: PRT
<213> ORGANISM: Artificial Sequence
<220> FEATURE:
<223> OTHER INFORMATION: PEP petide

<400> SEQUENCE: 79

Ile Gln Lys Val Ile Asp Gln Phe Gly Glu
1               5                   10

<210> SEQ ID NO 80
<211> LENGTH: 9
<212> TYPE: PRT
<213> ORGANISM: Artificial Sequence
<220> FEATURE:
<223> OTHER INFORMATION: PEP petide

<400> SEQUENCE: 80

Gln Lys Val Ile Asp Gln Phe Gly Glu
1               5

<210> SEQ ID NO 81
<211> LENGTH: 8
<212> TYPE: PRT
<213> ORGANISM: Artificial Sequence
<220> FEATURE:
<223> OTHER INFORMATION: PEP petide

<400> SEQUENCE: 81

Lys Val Ile Asp Gln Phe Gly Glu
1               5

<210> SEQ ID NO 82
<211> LENGTH: 7
<212> TYPE: PRT
<213> ORGANISM: Artificial Sequence
<220> FEATURE:
<223> OTHER INFORMATION: PEP petide

<400> SEQUENCE: 82

Val Ile Asp Gln Phe Gly Glu
1               5

<210> SEQ ID NO 83
<211> LENGTH: 6
<212> TYPE: PRT
<213> ORGANISM: Artificial Sequence
<220> FEATURE:
<223> OTHER INFORMATION: PEP petide

<400> SEQUENCE: 83

Ile Asp Gln Phe Gly Glu
1               5

<210> SEQ ID NO 84
<211> LENGTH: 18
<212> TYPE: PRT
<213> ORGANISM: Artificial Sequence
<220> FEATURE:
<223> OTHER INFORMATION: PEP petide

<400> SEQUENCE: 84

Tyr Thr His Val Phe Arg Leu Lys Lys Trp Ile Gln Lys Val Ile Asp
1               5                   10                  15

Gln Phe
```

```
<210> SEQ ID NO 85
<211> LENGTH: 14
<212> TYPE: PRT
<213> ORGANISM: Artificial Sequence
<220> FEATURE:
<223> OTHER INFORMATION: PEP petide

<400> SEQUENCE: 85

His Val Phe Arg Leu Lys Lys Trp Ile Gln Lys Val Ile Asp
1               5                   10

<210> SEQ ID NO 86
<211> LENGTH: 12
<212> TYPE: PRT
<213> ORGANISM: Artificial Sequence
<220> FEATURE:
<223> OTHER INFORMATION: PEP petide

<400> SEQUENCE: 86

Val Phe Arg Leu Lys Lys Trp Ile Gln Lys Val Ile
1               5                   10

<210> SEQ ID NO 87
<211> LENGTH: 10
<212> TYPE: PRT
<213> ORGANISM: Artificial Sequence
<220> FEATURE:
<223> OTHER INFORMATION: PEP petide

<400> SEQUENCE: 87

Phe Arg Leu Lys Lys Trp Ile Gln Lys Val
1               5                   10

<210> SEQ ID NO 88
<211> LENGTH: 8
<212> TYPE: PRT
<213> ORGANISM: Artificial Sequence
<220> FEATURE:
<223> OTHER INFORMATION: PEP petide

<400> SEQUENCE: 88

Arg Leu Lys Lys Trp Ile Gln Lys
1               5

<210> SEQ ID NO 89
<211> LENGTH: 6
<212> TYPE: PRT
<213> ORGANISM: Artificial Sequence
<220> FEATURE:
<223> OTHER INFORMATION: PEP petide

<400> SEQUENCE: 89

Leu Lys Lys Trp Ile Gln
1               5

<210> SEQ ID NO 90
<211> LENGTH: 16
<212> TYPE: PRT
<213> ORGANISM: Artificial sequence
<220> FEATURE:
<223> OTHER INFORMATION: K-S variant peptide

<400> SEQUENCE: 90

Thr His Val Phe Ser Leu Lys Lys Trp Ile Gln Lys Val Ile Asp Gln
1               5                   10                  15
```

```
<210> SEQ ID NO 91
<211> LENGTH: 16
<212> TYPE: PRT
<213> ORGANISM: Artificial Sequence
<220> FEATURE:
<223> OTHER INFORMATION: K-S variant peptide

<400> SEQUENCE: 91

Thr His Val Phe Arg Leu Ser Lys Trp Ile Gln Lys Val Ile Asp Gln
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: K-S variant peptide

<400> SEQUENCE: 92

Thr His Val Phe Arg Leu Lys Ser Trp Ile Gln Lys Val Ile Asp Gln
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: K-S variant peptide

<400> SEQUENCE: 93

Thr His Val Phe Arg Leu Lys Lys Trp Ile Gln Ser Val Ile Asp Gln
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: K-S variant peptide

<400> SEQUENCE: 94

Thr His Val Phe Ser Leu Ser Lys Trp Ile Gln Lys Val Ile Asp Gln
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: K-S variant peptide

<400> SEQUENCE: 95

Thr His Val Phe Arg Leu Lys Ser Trp Ile Gln Ser Val Ile Asp Gln
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: K-S variant peptide

<400> SEQUENCE: 96

Thr His Val Phe Ser Leu Lys Lys Trp Ile Gln Ser Val Ile Asp Gln
1               5                   10                  15

<210> SEQ ID NO 97
<211> LENGTH: 16
```

-continued

```
<212> TYPE: PRT
<213> ORGANISM: Artificial Sequence
<220> FEATURE:
<223> OTHER INFORMATION: K-S variant peptide

<400> SEQUENCE: 97

Thr His Val Phe Arg Leu Ser Ser Trp Ile Gln Lys Val Ile Asp Gln
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: K-S variant peptide

<400> SEQUENCE: 98

Thr His Val Phe Ser Leu Ser Ser Trp Ile Gln Lys Ser Ile Asp Gln
1               5                   10                  15
```